(12) United States Patent
Hariton et al.

(10) Patent No.: US 11,337,803 B2
(45) Date of Patent: May 24, 2022

(54) PROSTHETIC VALVE WITH INNER AND OUTER FRAMES CONNECTED AT A LOCATION OF TISSUE ANCHOR PORTION

(71) Applicant: CARDIOVALVE LTD., Or Yehuda (IL)

(72) Inventors: Ilia Hariton, Zichron Yaackov (IL); Meni Iamberger, Kfar Saba (IL); Aviram Baum, Tel Aviv (IL); Boaz Harari, Ganey Tikva (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 16/135,505

(22) Filed: Sep. 19, 2018

(65) Prior Publication Data

US 2019/0083243 A1    Mar. 21, 2019

Related U.S. Application Data

(60) Provisional application No. 62/560,384, filed on Sep. 19, 2017.

(51) Int. Cl.
*A61F 2/24*    (2006.01)

(52) U.S. Cl.
CPC ........... *A61F 2/2427* (2013.01); *A61F 2/243* (2013.01); *A61F 2/2436* (2013.01);
(Continued)

(58) Field of Classification Search
CPC .. A61F 2/2418; A61F 2/852; A61F 2220/008; A61F 2220/0041; A61F 2220/0016
See application file for complete search history.

(56) References Cited

U.S. PATENT DOCUMENTS

| 3,874,388 A | 4/1975 | King et al. |
| 4,222,126 A | 9/1980 | Boretos et al. |

(Continued)

FOREIGN PATENT DOCUMENTS

| CA | 2822801 A1 | 8/2006 |
| CN | 103974674 A | 8/2014 |

(Continued)

OTHER PUBLICATIONS

International Search Report dated Dec. 5. 2011, by the United States Patent and Trademark Office in PCT/IL2011/000582 (3 pages).
(Continued)

*Primary Examiner* — Brian E Pellegrino
(74) *Attorney, Agent, or Firm* — Sughrue Mion, PLLC

(57) ABSTRACT

A prosthetic heart valve, which may include an expandable annular outer frame having a tubular portion and at least one tissue anchor portion configured to extend from the tubular portion, may be provided. The at least one tissue anchor portion may have a plurality of attachment locations. The prosthetic heart valve may also include an expandable inner frame configured at least partially within the expandable annular outer frame. The expandable inner frame may be connected to the expandable annular outer frame solely at one or more of the plurality of attachment locations of the at least one tissue anchor portion.

17 Claims, 21 Drawing Sheets

(52) U.S. Cl.
CPC .......... *A61F 2/2445* (2013.01); *A61F 2/2454* (2013.01); *A61F 2/2463* (2013.01); *A61F 2/246* (2013.01); *A61F 2/2409* (2013.01); *A61F 2/2418* (2013.01); *A61F 2/2466* (2013.01); *A61F 2210/0014* (2013.01); *A61F 2220/0008* (2013.01); *A61F 2250/007* (2013.01)

(56) References Cited

U.S. PATENT DOCUMENTS

| | | | |
|---|---|---|---|
| 4,340,091 A | 7/1982 | Skelton et al. | |
| 5,201,757 A | 4/1993 | Heyn et al. | |
| 5,713,948 A | 2/1998 | Uflacker | |
| 5,716,417 A | 2/1998 | Girard et al. | |
| 5,741,297 A | 4/1998 | Simon | |
| 5,776,140 A | 7/1998 | Cottone | |
| 5,957,949 A | 9/1999 | Leonhardt et al. | |
| 5,961,549 A | 10/1999 | Nguyen et al. | |
| 6,010,530 A | 1/2000 | Goicoechea | |
| 6,126,686 A | 10/2000 | Badylak et al. | |
| 6,165,183 A | 12/2000 | Kuehn et al. | |
| 6,254,609 B1 | 7/2001 | Vrba et al. | |
| 6,312,465 B1 | 11/2001 | Griffin et al. | |
| 6,346,074 B1 | 2/2002 | Roth | |
| 6,402,780 B2 | 6/2002 | Williamson, IV et al. | |
| 6,458,153 B1 | 10/2002 | Bailey et al. | |
| 6,669,724 B2 | 12/2003 | Park et al. | |
| 6,733,525 B2 | 5/2004 | Yang et al. | |
| 6,752,813 B2 | 6/2004 | Goldfarb et al. | |
| 6,755,857 B2 | 6/2004 | Peterson et al. | |
| 6,926,715 B1 | 8/2005 | Hauck et al. | |
| 6,939,370 B2 | 9/2005 | Hartley et al. | |
| 7,074,236 B2 | 7/2006 | Rabkin et al. | |
| 7,201,772 B2 | 4/2007 | Schwammenthal et al. | |
| 7,226,467 B2 | 6/2007 | Lucatero et al. | |
| 7,261,686 B2 | 8/2007 | Couvillon, Jr. | |
| 7,288,097 B2 | 10/2007 | Séguin | |
| 7,442,204 B2 | 10/2008 | Schwammenthal et al. | |
| 7,556,632 B2 | 7/2009 | Zadno | |
| 7,563,267 B2 | 7/2009 | Goldfarb et al. | |
| 7,563,273 B2 | 7/2009 | Goldfarb et al. | |
| 7,608,091 B2 | 10/2009 | Goldfarb et al. | |
| 7,635,329 B2 | 12/2009 | Goldfarb et al. | |
| 7,655,015 B2 | 2/2010 | Goldfarb et al. | |
| 7,736,388 B2 | 6/2010 | Goldfarb et al. | |
| 7,753,949 B2 | 7/2010 | Lamphere et al. | |
| 7,811,296 B2 | 10/2010 | Goldfarb et al. | |
| 7,837,727 B2 | 11/2010 | Goetz et al. | |
| 7,959,672 B2 | 6/2011 | Salahieh et al. | |
| 8,052,592 B2 | 11/2011 | Goldfarb et al. | |
| 8,057,493 B2 | 11/2011 | Goldfarb et al. | |
| 8,070,802 B2 | 12/2011 | Lamphere et al. | |
| D652,927 S | 1/2012 | Braido et al. | |
| D653,341 S | 1/2012 | Braido et al. | |
| 8,109,996 B2 | 2/2012 | Stacchino et al. | |
| D660,433 S | 5/2012 | Braido et al. | |
| D660,967 S | 5/2012 | Braido et al. | |
| 8,216,256 B2 | 7/2012 | Raschdorf, Jr. et al. | |
| 8,313,525 B2 | 11/2012 | Tuval et al. | |
| 8,403,983 B2 | 3/2013 | Quadri et al. | |
| 8,414,644 B2 | 4/2013 | Quadri et al. | |
| 8,449,599 B2 | 5/2013 | Chau et al. | |
| 8,562,672 B2 | 10/2013 | Bonhoeffer et al. | |
| 8,568,475 B2 | 10/2013 | Nguyen et al. | |
| 8,579,964 B2 | 11/2013 | Lane et al. | |
| 8,585,755 B2 | 11/2013 | Chau et al. | |
| 8,628,571 B1 | 1/2014 | Hacohen et al. | |
| 8,652,203 B2 | 2/2014 | Quadri et al. | |
| 8,657,872 B2 | 2/2014 | Seguin | |
| 8,728,155 B2 | 5/2014 | Montorfano et al. | |
| 8,747,460 B2 | 6/2014 | Tuval et al. | |
| 8,784,481 B2 | 7/2014 | Alkhatib et al. | |
| 8,852,272 B2 | 10/2014 | Gross et al. | |
| 8,870,948 B1 | 10/2014 | Erzberger et al. | |
| 8,870,950 B2 | 10/2014 | Hacohen | |
| 8,961,595 B2 | 2/2015 | Alkhatib | |
| 8,986,375 B2 | 3/2015 | Garde et al. | |
| 8,992,604 B2 | 3/2015 | Gross et al. | |
| 8,998,982 B2 | 4/2015 | Richter et al. | |
| 9,017,399 B2 | 4/2015 | Gross et al. | |
| D730,520 S | 5/2015 | Braido et al. | |
| D730,521 S | 5/2015 | Braido et al. | |
| 9,023,100 B2 | 5/2015 | Quadri et al. | |
| D732,666 S | 6/2015 | Nguyen et al. | |
| 9,050,188 B2 | 6/2015 | Schweich, Jr. et al. | |
| 9,060,858 B2 | 6/2015 | Thornton et al. | |
| 9,072,603 B2 | 7/2015 | Tuval et al. | |
| 9,095,434 B2 | 8/2015 | Rowe | |
| 9,119,719 B2 | 9/2015 | Zipory et al. | |
| 9,125,740 B2 | 9/2015 | Morriss et al. | |
| 9,132,009 B2 | 9/2015 | Hacohen et al. | |
| 9,173,659 B2 | 11/2015 | Bodewadt et al. | |
| 9,180,009 B2 | 11/2015 | Majkrzak et al. | |
| 9,232,995 B2 | 1/2016 | Kovalsky et al. | |
| 9,241,790 B2 | 1/2016 | Lane et al. | |
| 9,241,791 B2 | 1/2016 | Braido et al. | |
| 9,241,792 B2 | 1/2016 | Benichou et al. | |
| 9,248,014 B2 | 2/2016 | Lane et al. | |
| 9,277,994 B2 | 3/2016 | Miller et al. | |
| 9,295,551 B2 | 3/2016 | Straubinger et al. | |
| 9,295,552 B2 | 3/2016 | McLean et al. | |
| 9,320,591 B2 | 4/2016 | Bolduc | |
| D755,384 S | 5/2016 | Pesce et al. | |
| 9,345,573 B2 | 5/2016 | Nyuli et al. | |
| 9,358,107 B2 | 6/2016 | Nguyen et al. | |
| 9,387,078 B2 | 7/2016 | Gross et al. | |
| 9,393,110 B2 | 7/2016 | Levi et al. | |
| 9,439,757 B2 | 9/2016 | Wallace et al. | |
| 9,445,893 B2 | 9/2016 | Vaturi | |
| 9,463,102 B2 | 10/2016 | Kelly | |
| 9,492,273 B2 | 11/2016 | Wallace et al. | |
| 9,532,870 B2 | 1/2017 | Cooper et al. | |
| 9,554,897 B2 | 1/2017 | Lane et al. | |
| 9,554,899 B2 | 1/2017 | Granada et al. | |
| 9,561,103 B2 | 2/2017 | Granada et al. | |
| 9,565,152 B2 | 2/2017 | Schweich, Jr. et al. | |
| 9,572,665 B2 | 2/2017 | Lane et al. | |
| 9,597,182 B2 | 3/2017 | Straubinger et al. | |
| 9,629,716 B2 | 4/2017 | Seguin | |
| 9,662,203 B2 | 5/2017 | Sheahan et al. | |
| 9,681,952 B2 | 6/2017 | Hacohen et al. | |
| 9,717,591 B2 | 8/2017 | Chau et al. | |
| 9,763,657 B2 | 9/2017 | Hacohen et al. | |
| 9,770,256 B2 | 9/2017 | Cohen et al. | |
| D800,908 S | 10/2017 | Hariton et al. | |
| 9,788,941 B2 | 10/2017 | Hacohen | |
| 9,895,226 B1 | 2/2018 | Harari et al. | |
| 9,974,651 B2 | 5/2018 | Hariton et al. | |
| 10,010,414 B2 | 7/2018 | Cooper et al. | |
| 10,076,415 B1 | 9/2018 | Metchik et al. | |
| 10,105,222 B1 | 10/2018 | Metchik et al. | |
| 10,111,751 B1 | 10/2018 | Metchik et al. | |
| 10,123,873 B1 | 11/2018 | Metchik et al. | |
| 10,130,475 B1 | 11/2018 | Metchik et al. | |
| 10,136,993 B1 | 11/2018 | Metchik et al. | |
| 10,143,552 B2 | 12/2018 | Wallace et al. | |
| 10,149,761 B2 | 12/2018 | Granada et al. | |
| 10,154,906 B2 | 12/2018 | Granada et al. | |
| 10,159,570 B1 | 12/2018 | Metchik et al. | |
| 10,182,908 B2 | 1/2019 | Tubishevitz et al. | |
| 10,226,341 B2 | 3/2019 | Gross et al. | |
| 10,231,837 B1 | 3/2019 | Metchik et al. | |
| 10,238,493 B1 | 3/2019 | Metchik et al. | |
| 10,245,143 B2 | 4/2019 | Gross et al. | |
| 10,245,144 B1 | 4/2019 | Metchik et al. | |
| 10,299,927 B2 | 5/2019 | McLean et al. | |
| 10,321,995 B1 | 6/2019 | Christianson et al. | |
| 10,322,020 B2 | 6/2019 | Lam et al. | |
| 10,327,895 B2 | 6/2019 | Lozonschi et al. | |
| 10,335,278 B2 | 7/2019 | McLean et al. | |
| 10,357,360 B2 | 7/2019 | Hariton et al. | |
| 10,376,361 B2 | 8/2019 | Gross et al. | |
| 10,390,952 B2 | 8/2019 | Hariton et al. | |

(56) References Cited

U.S. PATENT DOCUMENTS

| | | |
|---|---|---|
| 10,426,610 B2 | 10/2019 | Hariton et al. |
| 10,463,487 B2 | 11/2019 | Hariton et al. |
| 10,463,488 B2 | 11/2019 | Hariton et al. |
| 10,507,105 B2 | 12/2019 | Hariton et al. |
| 10,507,108 B2 | 12/2019 | Delgado et al. |
| 10,507,109 B2 | 12/2019 | Metchik et al. |
| 10,512,456 B2 | 12/2019 | Hacohen et al. |
| 10,517,719 B2 | 12/2019 | Miller et al. |
| 10,524,792 B2 | 1/2020 | Hernandez et al. |
| 10,524,903 B2 | 1/2020 | Hariton et al. |
| 10,531,872 B2 | 1/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,610,358 B2 | 4/2020 | Vidlund et al. |
| 10,646,342 B1 | 5/2020 | Marr et al. |
| 10,667,908 B2 | 6/2020 | Hariton et al. |
| 10,682,227 B2 | 6/2020 | Hariton et al. |
| 10,695,177 B2 | 6/2020 | Hariton et al. |
| 10,702,385 B2 | 7/2020 | Hacohen |
| 10,722,360 B2 | 7/2020 | Hariton et al. |
| 10,758,342 B2 | 9/2020 | Chau et al. |
| 10,758,344 B2 | 9/2020 | Hariton et al. |
| 10,799,345 B2 | 10/2020 | Hariton et al. |
| 10,813,760 B2 | 10/2020 | Metchik et al. |
| 10,820,998 B2 | 11/2020 | Marr et al. |
| 10,842,627 B2 | 11/2020 | Delgado et al. |
| 10,849,748 B2 | 12/2020 | Hariton et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,864,078 B2 | 12/2020 | Hariton et al. |
| 10,874,514 B2 | 12/2020 | Dixon et al. |
| 10,881,511 B2 | 1/2021 | Hariton et al. |
| 10,888,422 B2 | 1/2021 | Hariton et al. |
| 10,888,644 B2 | 1/2021 | Ratz et al. |
| 10,905,548 B2 | 2/2021 | Hariton et al. |
| 10,905,549 B2 | 2/2021 | Hariton et al. |
| 10,905,552 B2 | 2/2021 | Dixon et al. |
| 10,905,554 B2 | 2/2021 | Cao |
| 10,918,483 B2 | 2/2021 | Metchik et al. |
| 10,925,595 B2 | 2/2021 | Hacohen et al. |
| 10,945,844 B2 | 3/2021 | McCann et al. |
| 10,973,636 B2 | 4/2021 | Hariton et al. |
| 10,993,809 B2 | 5/2021 | McCann et al. |
| 11,083,582 B2 | 8/2021 | McCann et al. |
| 11,147,672 B2 | 10/2021 | McCann et al. |
| 2001/0005787 A1 | 6/2001 | Oz et al. |
| 2001/0021872 A1 | 9/2001 | Bailey et al. |
| 2002/0013571 A1 | 1/2002 | Goldfarb et al. |
| 2002/0032481 A1 | 3/2002 | Gabbay |
| 2003/0050694 A1 | 3/2003 | Yang et al. |
| 2003/0074059 A1 | 4/2003 | Nguyen et al. |
| 2004/0030382 A1 | 2/2004 | St. Goar et al. |
| 2004/0186558 A1 | 9/2004 | Pavcnik et al. |
| 2004/0210304 A1 | 10/2004 | Seguin et al. |
| 2004/0236354 A1 | 11/2004 | Seguin |
| 2004/0249433 A1 | 12/2004 | Freitag |
| 2005/0027348 A1 | 2/2005 | Case et al. |
| 2005/0080474 A1 | 4/2005 | Andreas et al. |
| 2005/0085900 A1 | 4/2005 | Case et al. |
| 2005/0137681 A1 | 6/2005 | Shoemaker et al. |
| 2005/0137691 A1 | 6/2005 | Salahieh et al. |
| 2005/0137692 A1 | 6/2005 | Haug et al. |
| 2005/0137697 A1 | 6/2005 | Salahieh et al. |
| 2005/0203618 A1 | 9/2005 | Sharkawy et al. |
| 2005/0240200 A1 | 10/2005 | Bergheim |
| 2005/0256566 A1 | 11/2005 | Gabbay |
| 2006/0004469 A1 | 1/2006 | Sokel |
| 2006/0020275 A1 | 1/2006 | Goldfarb et al. |
| 2006/0020327 A1 | 1/2006 | Lashinski et al. |
| 2006/0030863 A1 | 2/2006 | Fields et al. |
| 2006/0052867 A1 | 3/2006 | Revuelta et al. |
| 2006/0184203 A1 | 8/2006 | Martin et al. |
| 2006/0195183 A1 | 8/2006 | Navia et al. |
| 2006/0216404 A1 | 9/2006 | Seyler et al. |
| 2006/0229708 A1 | 10/2006 | Powell et al. |
| 2006/0259137 A1 | 11/2006 | Artof et al. |
| 2006/0282150 A1 | 12/2006 | Olson et al. |
| 2007/0016286 A1 | 1/2007 | Herrmann et al. |
| 2007/0038293 A1 | 2/2007 | St. Goar et al. |
| 2007/0056346 A1 | 3/2007 | Spenser et al. |
| 2007/0007851 A1 | 4/2007 | Ryan |
| 2007/0197858 A1 | 8/2007 | Goldfarb et al. |
| 2007/0198077 A1 | 8/2007 | Cully et al. |
| 2007/0213810 A1 | 9/2007 | Newhauser et al. |
| 2007/0219630 A1 | 9/2007 | Chu |
| 2007/0239273 A1 | 10/2007 | Allen |
| 2007/0244546 A1 | 10/2007 | Francis |
| 2008/0065011 A1 | 3/2008 | Marchand et al. |
| 2008/0071361 A1 | 3/2008 | Tuval et al. |
| 2008/0071369 A1 | 3/2008 | Tuval et al. |
| 2008/0082166 A1 | 4/2008 | Styrc et al. |
| 2008/0132989 A1 | 6/2008 | Snow et al. |
| 2008/0147182 A1 | 6/2008 | Righini et al. |
| 2008/0200980 A1 | 8/2008 | Robin et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2009/0005863 A1 | 1/2009 | Goetz et al. |
| 2009/0125098 A1 | 5/2009 | Chuter |
| 2009/0157175 A1 | 6/2009 | Benichou |
| 2009/0259306 A1 | 10/2009 | Rowe |
| 2009/0281619 A1 | 11/2009 | Le et al. |
| 2010/0022823 A1 | 1/2010 | Goldfarb et al. |
| 2010/0023120 A1 | 1/2010 | Holecek et al. |
| 2010/0049313 A1 | 2/2010 | Alon et al. |
| 2010/0312333 A1 | 2/2010 | Navia et al. |
| 2010/0100167 A1 | 4/2010 | Bortlein et al. |
| 2010/0161036 A1 | 6/2010 | Pintor et al. |
| 2010/0256737 A1 | 10/2010 | Pollock et al. |
| 2010/0331971 A1 | 12/2010 | Keranen et al. |
| 2011/0004227 A1 | 1/2011 | Goldfarb et al. |
| 2011/0004299 A1 | 1/2011 | Navia et al. |
| 2011/0029072 A1 | 2/2011 | Gabbay |
| 2011/0066233 A1 | 3/2011 | Thornton et al. |
| 2011/0137397 A1 | 6/2011 | Chau et al. |
| 2011/0144742 A1 | 6/2011 | Madrid et al. |
| 2011/0208283 A1 | 8/2011 | Rust |
| 2011/0224785 A1 | 9/2011 | Hacohen |
| 2011/0245911 A1 | 10/2011 | Quill et al. |
| 2011/0264196 A1 | 10/2011 | Savage et al. |
| 2011/0282439 A1 | 11/2011 | Thill et al. |
| 2011/0306916 A1 | 12/2011 | Nitzan et al. |
| 2011/0307049 A1 | 12/2011 | Kao |
| 2011/0313515 A1 | 12/2011 | Quadri et al. |
| 2011/0319989 A1 | 12/2011 | Lane et al. |
| 2012/0016468 A1 | 1/2012 | Robin et al. |
| 2012/0022629 A1 | 1/2012 | Perera et al. |
| 2012/0022639 A1 | 1/2012 | Hacohen et al. |
| 2012/0059458 A1 | 3/2012 | Buchbinder |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0089223 A1 | 4/2012 | Nguyen et al. |
| 2012/0101571 A1 | 4/2012 | Thambar et al. |
| 2012/0165930 A1 | 6/2012 | Gifford, III et al. |
| 2012/0296418 A1 | 11/2012 | Bonyuet et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2013/0018458 A1 | 1/2013 | Yohanan et al. |
| 2013/0046373 A1 | 2/2013 | Cartledge et al. |
| 2013/0066342 A1 | 3/2013 | Dell et al. |
| 2013/0144381 A1 | 6/2013 | Quadri et al. |
| 2013/0178930 A1 | 7/2013 | Straubinger et al. |
| 2013/0190861 A1 | 7/2013 | Chau et al. |
| 2013/0231735 A1 | 9/2013 | Deem et al. |
| 2013/0253643 A1 | 9/2013 | Rolando et al. |
| 2013/0261738 A1 | 10/2013 | Clague et al. |
| 2013/0274870 A1 | 10/2013 | Lombardi et al. |
| 2013/0282059 A1 | 10/2013 | Ketal et al. |
| 2013/0289711 A1 | 10/2013 | Liddy et al. |

(56) References Cited

U.S. PATENT DOCUMENTS

| | | |
|---|---|---|
| 2013/0289740 A1 | 10/2013 | Liddy et al. |
| 2013/0304200 A1 | 11/2013 | McLean et al. |
| 2014/0000112 A1 | 1/2014 | Braido et al. |
| 2014/0018915 A1 | 1/2014 | Biadillah et al. |
| 2014/0067050 A1 | 3/2014 | Costello et al. |
| 2014/0142688 A1 | 5/2014 | Duffy et al. |
| 2014/0172077 A1 | 6/2014 | Bruchman et al. |
| 2014/0172082 A1 | 6/2014 | Bruchman et al. |
| 2014/0194981 A1 | 7/2014 | Menk et al. |
| 2014/0207231 A1 | 7/2014 | Hacohen et al. |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257467 A1 | 9/2014 | Lane et al. |
| 2014/0277409 A1 | 9/2014 | Bortlein et al. |
| 2014/0277411 A1 | 9/2014 | Bortlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296969 A1 | 10/2014 | Tegels et al. |
| 2014/0324164 A1 | 10/2014 | Gross et al. |
| 2014/0343670 A1 | 11/2014 | Bakis et al. |
| 2014/0358222 A1 | 12/2014 | Gorman, III et al. |
| 2014/0358224 A1 | 12/2014 | Tegels et al. |
| 2015/0018944 A1 | 1/2015 | O'Connell et al. |
| 2015/0032205 A1 | 1/2015 | Matheny |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0196390 A1 | 7/2015 | Ma et al. |
| 2015/0196393 A1 | 7/2015 | Vidlund et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0250588 A1 | 9/2015 | Yang et al. |
| 2015/0272730 A1 | 10/2015 | Melnick et al. |
| 2015/0272734 A1 | 10/2015 | Sheps et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2015/0359631 A1 | 12/2015 | Sheahan et al. |
| 2016/0030169 A1 | 2/2016 | Shahriari |
| 2016/0030171 A1 | 2/2016 | Quijano et al. |
| 2016/0089482 A1 | 3/2016 | Siegenthaler |
| 2016/0100939 A1 | 4/2016 | Amstrong et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0158497 A1 | 6/2016 | Tran et al. |
| 2016/0175095 A1 | 6/2016 | Dienno et al. |
| 2016/0184098 A1 | 6/2016 | Vaturi |
| 2016/0262885 A1 | 9/2016 | Sandstrom et al. |
| 2016/0270911 A1 | 9/2016 | Ganesan et al. |
| 2016/0310268 A1 | 10/2016 | Oba et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0331525 A1 | 11/2016 | Straubinger et al. |
| 2016/0331526 A1 | 11/2016 | Schweich, Jr. et al. |
| 2016/0338706 A1 | 11/2016 | Rowe |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer et al. |
| 2017/0056166 A1 | 3/2017 | Ratz et al. |
| 2017/0056171 A1 | 3/2017 | Cooper et al. |
| 2017/0065411 A1 | 3/2017 | Grundeman et al. |
| 2017/0128205 A1 | 5/2017 | Tamir et al. |
| 2017/0135816 A1* | 5/2017 | Lashinski ............ A61F 2/2418 623/2.17 |
| 2017/0189174 A1 | 7/2017 | Braido et al. |
| 2017/0209264 A1 | 7/2017 | Chau et al. |
| 2017/0224323 A1 | 8/2017 | Rowe et al. |
| 2017/0231757 A1 | 8/2017 | Gassler |
| 2017/0231759 A1 | 8/2017 | Geist et al. |
| 2017/0231766 A1 | 8/2017 | Hariton et al. |
| 2017/0239048 A1 | 8/2017 | Goldfarb et al. |
| 2017/0325948 A1* | 11/2017 | Wallace ............... A61F 2/2418 623/2.18 |
| 2017/0333183 A1 | 11/2017 | Backus |
| 2017/0333187 A1 | 11/2017 | Hariton et al. |
| 2017/0367823 A1 | 12/2017 | Hariton et al. |
| 2018/0000580 A1 | 1/2018 | Wallace et al. |
| 2018/0021129 A1 | 1/2018 | Peterson et al. |
| 2018/0028215 A1 | 2/2018 | Cohen |
| 2018/0049873 A1 | 2/2018 | Manash et al. |
| 2018/0055630 A1 | 3/2018 | Patel et al. |
| 2018/0098850 A1 | 4/2018 | Rafiee et al. |
| 2018/0116843 A1 | 5/2018 | Schreck et al. |
| 2018/0125644 A1 | 5/2018 | Conklin |
| 2018/0153689 A1 | 6/2018 | Maimon et al. |
| 2018/0206983 A1 | 7/2018 | Noe et al. |
| 2018/0214263 A1 | 8/2018 | Rolando et al. |
| 2018/0250126 A1 | 9/2018 | O'Connor et al. |
| 2018/0250130 A1 | 9/2018 | Hariton et al. |
| 2018/0250147 A1 | 9/2018 | Syed |
| 2018/0256323 A1 | 9/2018 | Hariton et al. |
| 2018/0256325 A1 | 9/2018 | Hariton et al. |
| 2018/0271654 A1 | 9/2018 | Hariton et al. |
| 2018/0271655 A1 | 9/2018 | Hariton et al. |
| 2018/0289479 A1 | 10/2018 | Hariton et al. |
| 2018/0296336 A1 | 10/2018 | Cooper et al. |
| 2018/0338829 A1 | 11/2018 | Hariton et al. |
| 2018/0338830 A1 | 11/2018 | Hariton et al. |
| 2018/0338831 A1 | 11/2018 | Hariton et al. |
| 2018/0344457 A1 | 12/2018 | Gross et al. |
| 2018/0353294 A1 | 12/2018 | Calomeni et al. |
| 2018/0360457 A1 | 12/2018 | Ellis et al. |
| 2019/0015093 A1 | 1/2019 | Hacohen et al. |
| 2019/0053896 A1 | 2/2019 | Adamek-Bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0083242 A1 | 3/2019 | Hariton et al. |
| 2019/0083243 A1 | 3/2019 | Hariton et al. |
| 2019/0083246 A1 | 3/2019 | Hariton et al. |
| 2019/0083247 A1 | 3/2019 | Hariton et al. |
| 2019/0105153 A1 | 4/2019 | Barash et al. |
| 2019/0117391 A1 | 4/2019 | Humair |
| 2019/0175339 A1 | 6/2019 | Vidlund |
| 2019/0183639 A1 | 6/2019 | Moore |
| 2019/0192295 A1 | 6/2019 | Spence et al. |
| 2019/0328519 A1 | 10/2019 | Hariton et al. |
| 2019/0336280 A1 | 11/2019 | Naor et al. |
| 2019/0343627 A1 | 11/2019 | Hariton et al. |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2019/0388223 A1 | 12/2019 | Hariton et al. |
| 2020/0000449 A1 | 1/2020 | Goldfarb et al. |
| 2020/0000579 A1 | 1/2020 | Manash et al. |
| 2020/0015964 A1 | 1/2020 | Noe et al. |
| 2020/0030098 A1 | 1/2020 | Delgado et al. |
| 2020/0046497 A1 | 2/2020 | Hariton et al. |
| 2020/0054335 A1 | 2/2020 | Hernandez et al. |
| 2020/0054451 A1 | 2/2020 | Hariton et al. |
| 2020/0060818 A1 | 2/2020 | Geist et al. |
| 2020/0069424 A1 | 3/2020 | Hariton et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0129294 A1 | 4/2020 | Hariton et al. |

(56) References Cited

U.S. PATENT DOCUMENTS

| | | |
|---|---|---|
| 2020/0138567 A1 | 5/2020 | Marr et al. |
| 2020/0163761 A1 | 5/2020 | Hariton et al. |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0246140 A1 | 8/2020 | Hariton et al. |
| 2020/0253600 A1 | 8/2020 | Darabian |
| 2020/0261094 A1 | 8/2020 | Goldfarb et al. |
| 2020/0315786 A1 | 10/2020 | Metchik et al. |
| 2020/0337842 A1 | 10/2020 | Metchik et al. |
| 2021/0085455 A1 | 3/2021 | Bateman et al. |
| 2021/0093449 A1 | 4/2021 | Hariton et al. |
| 2021/0113331 A1 | 4/2021 | Quadri et al. |

FOREIGN PATENT DOCUMENTS

| | | |
|---|---|---|
| EP | 1264582 A2 | 12/2002 |
| EP | 1637092 A2 | 3/2006 |
| EP | 2349124 B1 | 10/2018 |
| EP | 3583922 A1 | 12/2019 |
| EP | 3270825 B1 | 4/2020 |
| EP | 2485795 B1 | 9/2020 |
| WO | WO 2003/020179 A1 | 3/2003 |
| WO | WO 2004/028399 A2 | 4/2004 |
| WO | WO 2006/007389 A1 | 1/2006 |
| WO | WO 2006/086434 A1 | 8/2006 |
| WO | WO 2006/116558 A2 | 11/2006 |
| WO | WO 2006/128193 A2 | 11/2006 |
| WO | WO 2007/047488 A2 | 4/2007 |
| WO | WO 2008/029296 A2 | 3/2008 |
| WO | WO 2009/091509 A1 | 7/2009 |
| WO | WO 2010/006627 A1 | 1/2010 |
| WO | WO 2010/027485 A1 | 3/2010 |
| WO | WO 2010/045297 A2 | 4/2010 |
| WO | WO 2010/057262 A1 | 5/2010 |
| WO | WO 2011/069048 A2 | 6/2011 |
| WO | WO 2011/144351 A2 | 11/2011 |
| WO | WO 2012/011108 A2 | 1/2012 |
| WO | WO 2012/036740 A2 | 3/2012 |
| WO | WO 2012/048035 A2 | 4/2012 |
| WO | WO 2013/059747 A1 | 4/2013 |
| WO | WO 2013/072496 A1 | 5/2013 |
| WO | WO 2013/078497 A1 | 6/2013 |
| WO | WO 2013/114214 A2 | 8/2013 |
| WO | WO 2013/175468 A2 | 11/2013 |
| WO | WO 2014/115149 A2 | 7/2014 |
| WO | WO 2014/144937 A2 | 9/2014 |
| WO | WO 2014/164364 A1 | 10/2014 |
| WO | WO 2016/016899 A1 | 2/2016 |
| WO | WO 2016/098104 A2 | 6/2016 |
| WO | WO 2016/125160 A1 | 8/2016 |
| WO | WO 2016/150806 A1 | 9/2016 |
| WO | WO 2018/025260 A1 | 2/2018 |
| WO | WO 2018/025263 A2 | 2/2018 |
| WO | WO 2018/029680 A1 | 2/2018 |
| WO | WO 2018/039631 A1 | 3/2018 |
| WO | WO 2018/112429 A1 | 6/2018 |
| WO | WO 2018/118717 A1 | 6/2018 |
| WO | WO 2018/131042 A1 | 7/2018 |
| WO | WO 2018/131043 A1 | 7/2018 |
| WO | WO 2019/027507 A1 | 2/2019 |
| WO | WO 2019/195860 A2 | 10/2019 |
| WO | WO 2020/167677 A1 | 8/2020 |

OTHER PUBLICATIONS

International Search Report dated Mar. 27, 2018, by the European Patent Office in PCT/IL2017/050849 (5 pages).
International Search Report dated May 30, 2016, by the European Patent Office in PCT/IL2016/050125 (6 pages).
International Search Report dated Nov. 24, 2017, by the European Patent Office in PCT/IL2017/050873 (5 pages).
International Search Report dated Oct. 27, 2015, by the European Patent Office in PCT/IL2015/050792 (3 pages).
International Search Report dated Sep. 4, 2014, by the European Patent Office in PCT/IL2014/050087 (6 pages).
Written Opinion of the International Searching Authority issued by the United States Patent and Trademark Office in PCT/IL2011/000582 (12 pages).
Written Opinion of the International Searching Authority issued by the European Patent Office in PCT/IL2017/050649 (10 pages).
Written Opinion of the International Searching Authority issued by the European Patent Office in PCT/IL2016/050125 (7 pages).
Written Opinion of the International Searching Authority issued by the European Patent Office in PCT/IL2014/050087 (10 pages).
Written Opinion of the International Searching Authority issued by the European Patent Office in Written PCT/IL2015/050792 (5 pages).
Written Opinion of the International Searching Authority issued by the European Patent Office in PCT/IL2017/050873 (12 pages).
Batista, Randas J. V. et al., Partial Left Ventriculectomy to Treat End-Stage Heart Disease, 64 Annals Thoracic Surgery 634-38 (1997) (5 pages).
Beall, Jr., Arthur C. et al., Clinical Experience with a Dacron Velour-Covered Teflon-Disc Mitral-Valve Prosthesis, 5 Annals Thoracic Surgery 402-10 (1968) (9 pages).
Fucci, Carlo et al., Improved Results with Mitral Valve Repair Using New Surgical Techniques, 9 Eur. J. Cardiothoracic Surgery 621-27 (1995) (7 pages).
Maisano, Francesco et al., The Edge-To-Edge Technique: A Simplified Method to Correct Mitral Insufficiency, 13 Eur. J. Cardiothoracic Surgery 240-46 (1998) (7 pages).
Stone, Gregg W. et al., Clinical Trial Design Principles and Endpoint Definitions for Transcatheter Mitral Valve Repair and Replacement: Part 1: Clinical Trial Design Principles, 66 J. Am. C. Cardiology 278-307 (2015) (30 pages).
Sündermann, Simon H. et al., Feasibility of the Engager™ aortic transcatheter valve system using a flexible over-the-wire design, 42 European Journal of Cardio-Thoracic Surgery, Jun. 27, 2012, at e48 (5 pages).
Symetis S.A., Clinical Investigation Plan for Acurate Neo™ TA Delivery System, Protocol Jan. 2015, ver. 2, ClinicalTrials.gov Identifier NCT02950428, Sep. 8, 2015 (76 pages).
Tchetche, Didier et al., New-generation TAVI devices: description and specifications, 10 EuroIntervention (Supplement), Sep. 2014, at U90 (11 pages).
Poirier, Nancy et al., A Novel Repair for Patients with Atrioventricular Septal Defect Requiring Reoperation for Left Atrioventricular Valve Regurgitation, 18 Eur. J. Cardiothoracic Surgery 54-61 (2000) (8 pages).
Ando, Tomo et al., Iatrogenic Ventricular Septal Defect Following Transcatheter Aortic Valve Replacement: A Systematic Review, 25 Heart, Lung, and Circulation 968-74 (2016) (7 pages).
Urina, Marina et al., Transseptal Transcatheter Mitral Valve Replacement Using Balloon-Expandable Transcatheter Heart Valves, JACC: Cardiovascular Interventions 1905-19 (2017) (15 pages).
*Edwards Lifesciences Corp. v. Cardiovalve Ltd.*, IPR2021-00383, Exhibit 1014: Transcript of proceedings held May 20, 2021 (filed May 26, 2021) (21 pages).
*Edwards Lifesciences Corp. v. Cardiovalve Ltd.*, IPR2021-00383, Paper 12: Petitioners' Authorized Reply to Patent Owner's Preliminary Response (filed May 27, 2021) (9 pages).
*Edwards Lifesciences Corp. v. Cardiovalve Ltd.*, IPR2021-00383, Exhibit 1015: Facilitate, Meriam-Webster.com, https://www.meriamwebster.com/dictionary/facilitate (filed May 27, 2021) (5 pages).
*Edwards Lifesciences Corp. v. Cardiovalve Ltd.*, IPR2021-00383, Paper 13: Patent Owner's Authorized Surreply to Petitioner's Reply to Patent Owner's Preliminary Response (filed Jun. 4, 2021) (8 pages).
*Edwards Lifesciences Corp. v. Cardiovalve Ltd.*, IPR2021-00383, Paper 16: Institution Decision (filed Jul. 20, 2021) (51 pages).
*Edwards Lifesciences Corp. v. Cardiovalve Ltd.*, IPR2021-00383, Exhibit 2009: Percutaneous Mitral Leaflet Repair: MitraClip Therapy for Mitral Regurgitation (Aug. 17, 2012) (8 pages).

(56) References Cited

OTHER PUBLICATIONS

*Edwards Lifesciences Corp.* v. *Cardiovalve Ltd.*, IPR2021-00383, Exhibit 2010: Deposition of Dr. Ivan Vesely, Ph.D. (Sep. 27, 2021) (170 pages).
*Edwards Lifesciences Corp.* v. *Cardiovalve Ltd.*, IPR2021-00383, Exhibit 2014: Second Declaration of Dr. Michael Sacks (Oct. 13, 2021) (28 pages).
*Edwards Lifesciences Corp.* v. *Cardiovalve Ltd.*, IPR2021-00383, Patent Owner's Contingent Motion to Amend Under 37 C.F.R. § 42.121 (Oct. 13, 2021) (35 pages).
*Edwards Lifesciences Corp.* v. *Cardiovalve Ltd.*, IPR2021-00383, Patent Owner's Response Pursuant to 37 C.F.R. § 42.120 (Oct. 13, 2021) (75 pages).
*Edwards Lifesciences Corp.* v. *Cardiovalve Ltd.*, IPR2021-00383, Paper 10: Decision Granting Institution of Inter Partes Review (Dec. 10, 2021) (42 pages).
*Edwards Lifesciences Corp.* v. *Cardiovalve Ltd.*, IPR2021-00383, Petitioners' Opposition to Patent Owner's Contingent Motion to Amend (Jan. 5, 2022) (32 pages).
*Edwards Lifesciences Corp.* v. *Cardiovalve Ltd.*, IPR2021-00383, Petitioners' Reply to Patent Owner's Response (Jan. 5, 2022) (41 pages).
Fann, James I. et al., Beating Heart Catheter-Based Edge-to-Edge Mitral Valve Procedure in a Porcine Model: Efficacy and Healing Response, 110 Circulation, Aug. 2004, at 988 (6 pages).
Feldman, Ted et al., Percutaneous Mitral Repair With the MitraClip System: Safety and Midterm Durability in the Initial Everest Cohort, 54 J. Am. Coll. Cardiology, Aug. 2009, at 686 (9 pages).
Feldman, Ted et al., Percutaneous Mitral Valve Repair Using the Edge-to-Edge Technique: Six-Month Results of the Everest Phase I Clinical Trial, 46 J. Am. Coll. Cardiology, Dec. 2005, at 3134 (7 pages).
Maisano, Francesco et al., The Evolution From Surgery to Percutaneous Mitral Valve Interventions: The Role of the Edge-to-Edge Technique, 58 J. Am. Coll. Cardiology, Nov. 2011, at 2174 (9 pages).

\* cited by examiner

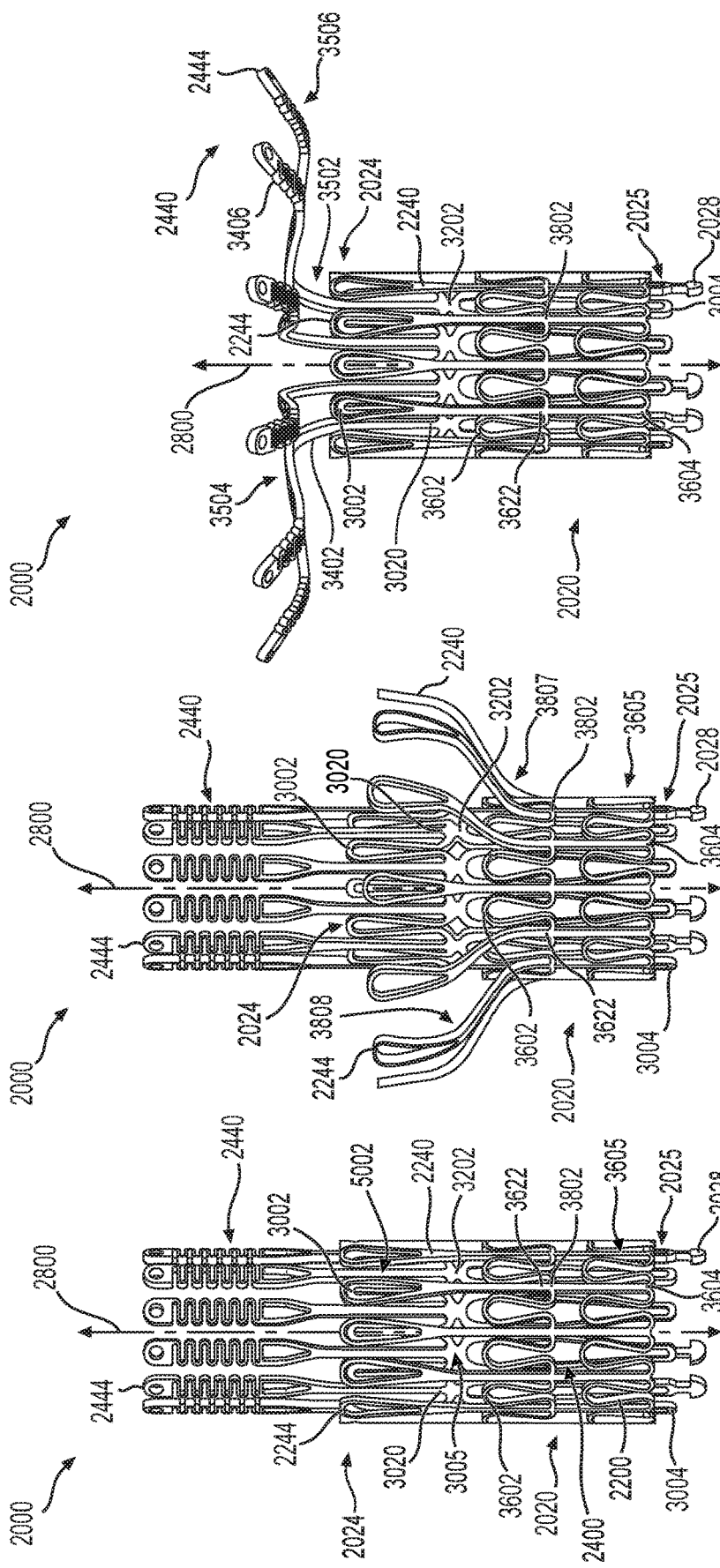

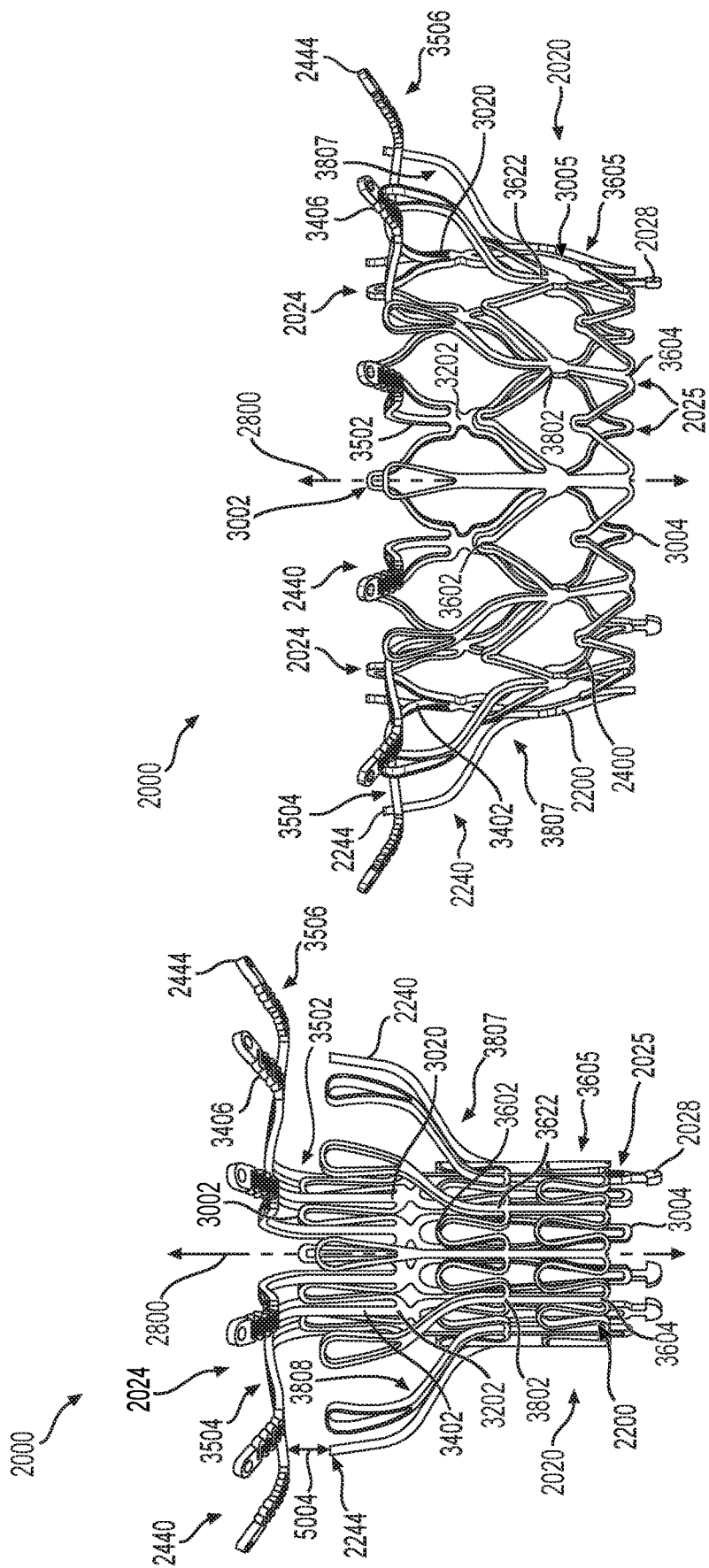

PROSTHETIC VALVE WITH INNER AND OUTER FRAMES CONNECTED AT A LOCATION OF TISSUE ANCHOR PORTION

CROSS-REFERENCE TO RELATED APPLICATION

This application claims priority from U.S. Provisional Patent Application No. 62/560,384, filed Sep. 19, 2017, which is hereby incorporated by reference in its entirety.

TECHNICAL FIELD

This disclosure relates generally to prosthetic valves and delivery systems for prosthetic valves. More specifically, this disclosure relates to prosthetic heart valves and methods thereof.

BACKGROUND

The native heart valves (the tricuspid valve, pulmonary valve, mitral valve, and aortic valve) play an important role in regulating flow of blood through the cardiovascular system. However, the native heart valves may become damaged or impaired due to, for example, cardiovascular diseases, infections, or congenital malformations, thus limiting the ability of the native heart valves to regulate blood flow. This deficiency may result in reduced cardiovascular function or even death.

To treat these conditions, prosthetic heart valves may be implanted at or near the site of a damaged or impaired native valve. A prosthetic heart valve may assist or replace the functionality of an impaired native valve, leading to better regulation of blood flow and improved cardiovascular function. However, many existing prosthetic heart valves require implantation via an open heart procedure, which is highly-invasive and may cause life-threatening complications. Other prosthetic valves may be collapsed within a prosthetic valve delivery system and advanced into the heart, at which point the prosthetic valve may be removed from the delivery system and expanded at the native valve site. However, many of these prosthetic valves are large in size and therefore difficult to deliver into the heart without causing damage to healthy tissue along the implantation route. In addition, once these prosthetic valves are situated within the heart, they may be difficult to securely implant at the native valve site due to their complex structure and the limited maneuverability of existing prosthetic valve delivery systems within the heart. Moreover, many prosthetic valves are so large that they may protrude several centimeters into surrounding heart chambers once they are implanted, impairing cardiac filling and causing injury to the anatomy within the heart.

Thus, there remains a need for prosthetic heart valves that are smaller in size but that are still configured to assist or replace the functionality of a diseased or damaged native heart valve. In addition, there remains a need for prosthetic heart valves that are more easily maneuvered into the heart and securely implanted at the site of a native heart valve. Moreover, there remains a need for improved prosthetic heart valve delivery systems that are configured to securely implant a prosthetic heart valve at an implantation site. The present disclosure provides prosthetic heart valves with a reduced axial length such that the prosthetic heart valves may be more easily delivered into the heart and may exhibit less protrusion into the chambers of the heart. The present disclosure also provides improved prosthetic heart valve delivery systems and methods of implanting prosthetic heart valves, such that prosthetic heart valves may be securely anchored at the implantation site.

SUMMARY

The present disclosure discloses prosthetic valves for implantation within a native mitral valve and methods for implanting prosthetic valves within a native mitral valve. Particular examples of the disclosure may pertain to a prosthetic valve including an outer frame and an inner frame connected together solely at attachment locations of one or more tissue anchors to the outer frame.

According to an exemplary embodiment of the present disclosure, a prosthetic heart valve is provided. The prosthetic heart valve includes an expandable annular outer frame having a tubular portion and at least one tissue anchor portion configured to extend from the tubular portion. The at least one tissue anchor portion includes a plurality of attachment locations. The prosthetic heart valve additionally includes an expandable inner frame configured at least partially within the expandable annular outer frame. The expandable inner frame is connected to the expandable annular outer frame solely at one or more of the plurality of attachment locations of the at least one tissue anchor portion.

The at least one tissue anchor portion extends from the tubular portion at one or more of the plurality of attachment locations. The plurality of attachment locations are substantially aligned in a common lateral plane. The expandable inner frame and expandable annular outer frame are connected by at least one connector configured to extend radially outward beyond the plurality of attachment locations. The at least one tissue anchor portion includes one or more ventricular anchoring legs configured to extend radially outward from the expandable annular outer frame. Radially external to the plurality of attachment locations, no connection is made between the one or more ventricular anchoring legs. Each of the one or more ventricular anchoring legs is associated with a single attachment location. The tubular portion of the expandable annular outer frame includes atrial and ventricular ends. The attachment locations are positioned away from the atrial and ventricular ends of the tubular portion. The outer frame tubular portion is formed at least partially of struts intersecting at junctions, including a plurality of atrial junctions at an atrial end of the tubular portion, a plurality of ventricular junctions at a ventricular end of the tubular portion, and a plurality of intermediate junctions between the atrial junctions and ventricular junctions. One or more of the attachment locations is situated within at least one intermediate junction. Each attachment location is situated within a junction at which at least three struts intersect. At least one of the at least three struts extends between the attachment location and a ventricular junction. One or more of the attachment locations is angularly offset from the plurality of atrial junctions of the outer frame tubular portion. The expandable inner frame is formed at least partially of struts intersecting at junctions. The expandable inner frame is connected to the outer frame at one or more junctions of the expandable inner frame. At least four struts intersect at the one or more junctions of the expandable inner frame. The prosthetic heart valve additionally includes a plurality of atrial anchoring arms configured to extend from the expandable inner frame. One or more of the attachment locations is angularly offset from the atrial anchoring arms. The expandable inner frame has a greater axial length than the expandable annular outer frame. The expandable inner frame additionally includes at least one delivery post extending from a ventricular end of the expandable inner frame. The at least one delivery post is angularly offset from one or more of the attachment locations. The prosthetic heart valve is configured for expansion from a radially-contracted configuration to a radially-expanded configuration. A distance between a particular attachment location and a ventricular end of the annular outer frame is constant between the radially-contracted configuration and the radially-expanded configuration.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIGS. 5A-5E illustrate structural changes in the exemplary frame of FIG. 2A during transitioning of the frame between a radially-contracted configuration and a radially-expanded configuration, consistent with various embodiments of the present disclosure.

DETAILED DESCRIPTION

Figure 1A:
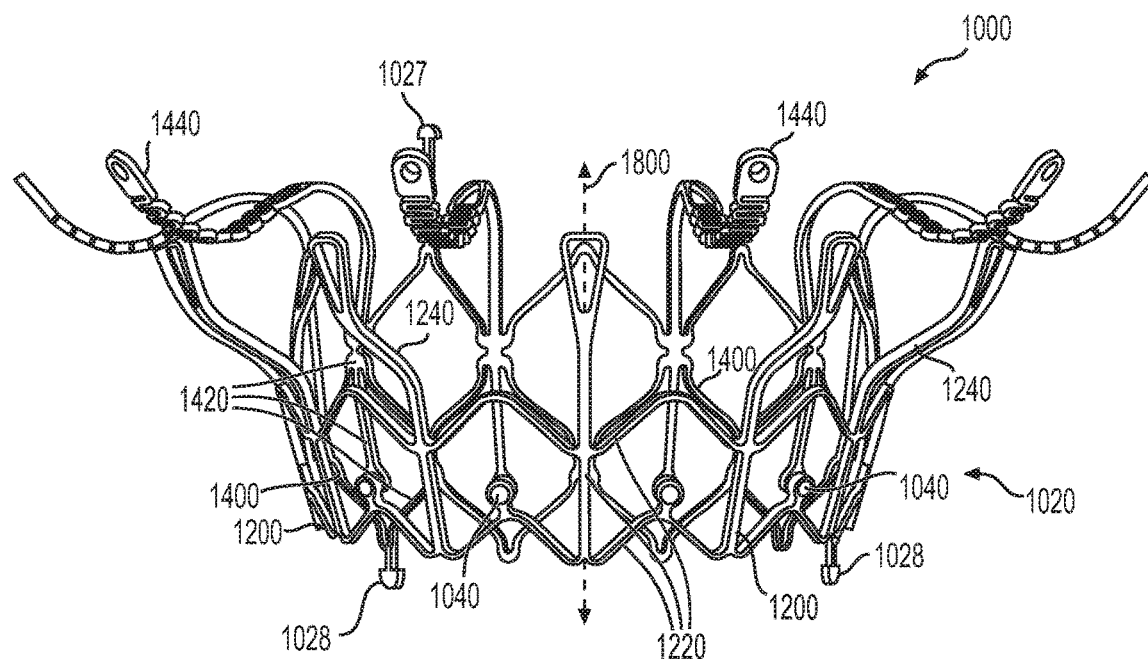
FIG. 1A illustrates a front elevation view of an exemplary frame for a prosthetic valve, consistent with various embodiments of the present disclosure.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used in the present disclosure and in the appended claims, the singular forms "a," "an," and "the" include plural references unless the context clearly dictates otherwise.

In some embodiments of the present disclosure, an "atrial direction" may refer to a direction extending towards an atrium of the heart. For example, from a location within the left ventricle or the mitral valve, an atrial direction may refer to a direction extending towards the left atrium. Additionally, from a location within an atrium (e.g., the left atrium), an atrial direction may refer to a direction extending away from an adjacent atrioventricular valve (e.g., the mitral valve) and further into the atrium. For example, in FIGS. 10G and 10H, an atrial direction may refer to a direction extending upwards from prosthetic valve 6000 towards atrium 9010. In some exemplary embodiments, an atrial direction need not necessarily be parallel to a longitudinal axis of a prosthetic valve (e.g., longitudinal axis 2800 illustrated in FIG. 2A), so long as the direction is angled towards an atrium. The atrial direction may be parallel to a longitudinal axis of a prosthetic valve in some cases. In some embodiments, a "non-ventricular direction" may refer to a direction that does not extend towards a ventricle of the heart. A "non-ventricular direction" may extend in an atrial direction, or it may extend laterally in a direction perpendicular to a ventricular direction.

In some exemplary embodiments of the present disclosure, a "ventricular direction" may refer to a direction extending towards a ventricle of the heart. From a location within the left atrium or the mitral valve, a ventricular direction may refer to a direction extending towards the left ventricle. Additionally, from a location within a ventricle (e.g., the left ventricle), a ventricular direction may refer to a direction extending away from an adjacent atrioventricular valve (e.g., the mitral valve) and further into the ventricle. For example, in FIGS. 10G and 10H, a ventricular direction may refer to a direction extending downwards from prosthetic valve 6000 towards ventricle 9020. In some exemplary embodiments, a ventricular direction need not necessarily be parallel to a longitudinal axis of a prosthetic valve (e.g., longitudinal axis 2800 illustrated in FIG. 2A), so long as the direction is angled towards a ventricle. The ventricular direction may be parallel to a longitudinal axis of a prosthetic valve in some cases. In some embodiments, a "non-atrial direction" may refer to a direction that does not extend towards an atrium of the heart. A non-atrial direction may extend in a ventricular direction, or it may extend laterally in a direction perpendicular to an atrial direction.

Exemplary embodiments generally relate to prosthetic valves for implantation within a native valve and methods for implanting prosthetic valves within a native valve. In addition, exemplary embodiments generally relate to systems and methods for implantation of prosthetic valves by prosthetic valve delivery systems. While the present disclosure provides examples relating to prosthetic heart valves, and in particular prosthetic mitral valves, as well as delivery systems for prosthetic heart valves, it should be noted that aspects of the disclosure in their broadest sense are not limited to a prosthetic heart valve. Rather, the foregoing principles may be applied to other prosthetic valves as well. In various embodiments in accordance with the present disclosure, the term prosthetic valve refers generally to an implantable valve configured to restore and/or replace the functionality of a native valve, such as a diseased or otherwise impaired native heart valve.

An exemplary prosthetic valve may include a prosthetic valve configured to render a native valve structure non-functional, and may thus replace the function of the native valve. For example, an exemplary prosthetic valve may have a size and shape similar to the valve being replaced and may include a number of leaflet-like structures to regulate fluid flow and prevent backflow of blood through the valve. Additionally, or alternatively, an exemplary prosthetic valve may also include a prosthetic valve configured to leave the native valve structure intact and functional. An exemplary prosthetic valve may include a mitral valve, tricuspid valve, aortic valve, or pulmonary valve, as well as a valve outside of the heart, such as a venous valve, lymph node valve, ileocecal valve, or any other structure configured to control and/or regulate fluid flow in the body. An exemplary prosthetic valve may additionally or alternatively be configured to replace a failed bioprosthesis, such as a failed heart valve prosthesis.

Figure 1B:
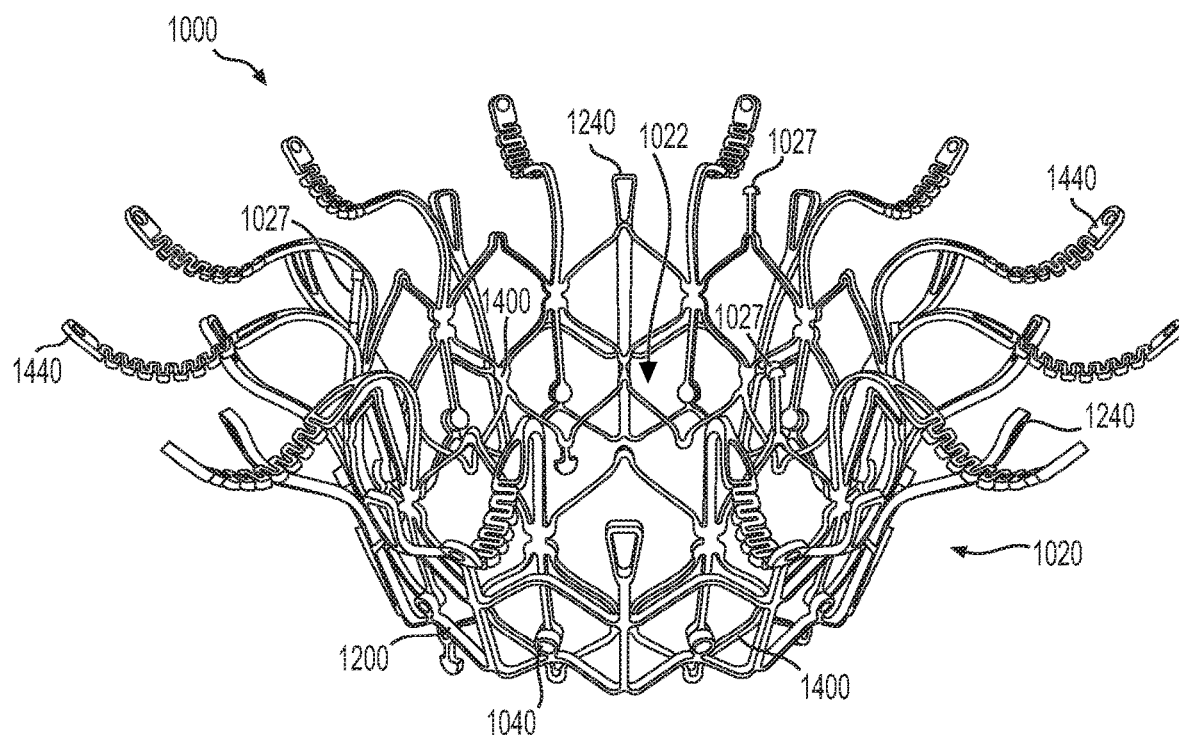
FIG. 1B illustrates a perspective view of the exemplary frame of FIG. 1A, consistent with various embodiments of the present disclosure.

FIG. 1A illustrates a front elevation view of an exemplary frame 1000 for a prosthetic valve. FIG. 1B illustrates a perspective view of frame 1000. Frame 1000 may be constructed of a shape memory material such as nickel titanium alloy (Nitinol) and may be configured to support other components of the prosthetic valve, such as prosthetic leaflets and protective cover layers. Frame 1000 may include an annular outer frame 1200 and an inner frame 1400 situated at least partially within the outer frame 1200. Annular outer frame 1200 and inner frame 1400 may be secured together by pins, screws, welding, soldering, adhesive, magnets, and/or any other suitable mechanism. For example, FIGS. 1A and 1B depict annular outer frame 1200 and inner frame 1400 connected by a plurality of connector pins 1040.

Annular outer frame 1200 may include an outer frame tubular portion 1220, which may be formed of a plurality of struts intersecting at junctions to form a wire mesh, stent-like, or cage-like structure of the outer frame tubular portion 1220. Annular outer frame 1200 may also include at least one ventricular anchoring leg 1240, which may be configured to extend radially outward from the outer frame tubular portion and which may contact, or otherwise engage, tissue within or near the native valve to anchor the prosthetic valve within the native valve. In some embodiments, exemplary valve frame 1000 may include twelve ventricular anchoring legs 1240, which may be configured to engage ventricular tissue of a native atrioventricular valve.

Inner frame 1400 may include an inner frame tubular portion 1420, which may be formed of a plurality of struts intersecting at junctions to form a wire mesh, stent-like, or cage-like structure of the inner frame tubular portion 1420. Inner frame 1400 may also include at least one atrial anchoring arm 1440, which may be configured to extend radially outward from the inner frame tubular portion and which may contact, or otherwise engage, tissue within or near the native valve to anchor the prosthetic valve within the native valve. In some embodiments, exemplary valve frame 1000 may include twelve atrial anchoring arms 1440, which may be configured to engage atrial tissue of a native atrioventricular valve.

Outer frame tubular portion 1220 and inner frame tubular portion 1420 may together form an annular valve body 1020 of the prosthetic valve, which may have at least one opening and from which the ventricular anchoring legs 1240 and atrial anchoring arms 1440 may extend. Annular valve body 1020 may include an axial lumen 1022 extending through the annular valve body 1020 along a longitudinal axis 1800 of the prosthetic valve. In some embodiments, annular valve body 1020 may be configured to receive a flow control device, such as one or more prosthetic leaflets, within axial lumen 1022. Optionally, annular valve body 1020 may include one or more atrial end delivery posts 1027 along an atrial end (i.e., top end) of the annular valve body and/or one or more ventricular end delivery posts 1028 along a ventricular end (i.e., bottom end) of the annular valve body. Delivery posts 1027 and 1028 may be configured to removably engage a delivery device of the prosthetic valve, for example, to assist with placement of frame 1000 within or near a native valve.

Figure 2A:
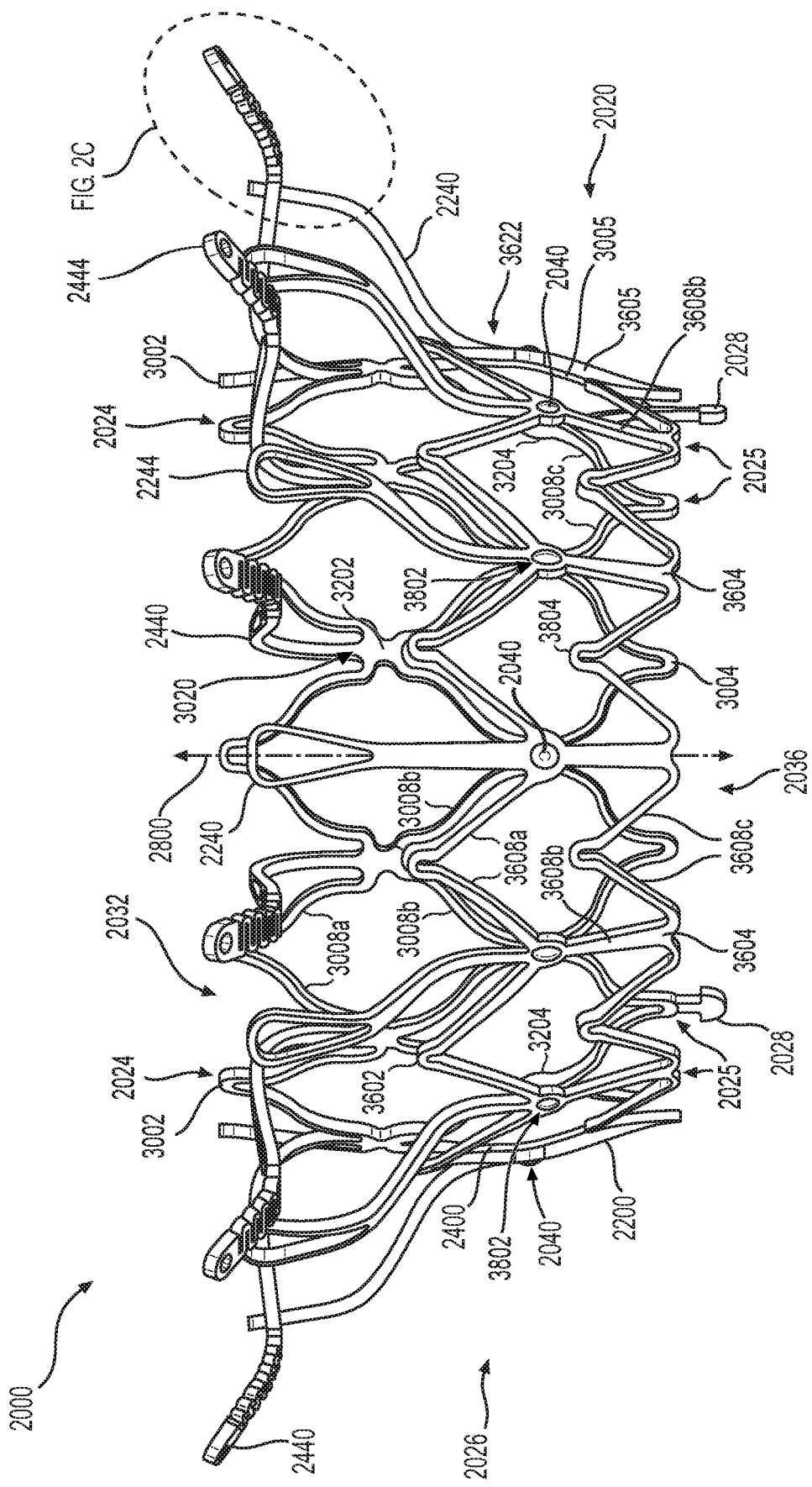
FIG. 2A illustrates a front elevation view of another exemplary frame for a prosthetic valve, consistent with various embodiments of the present disclosure.
Figure 2B:
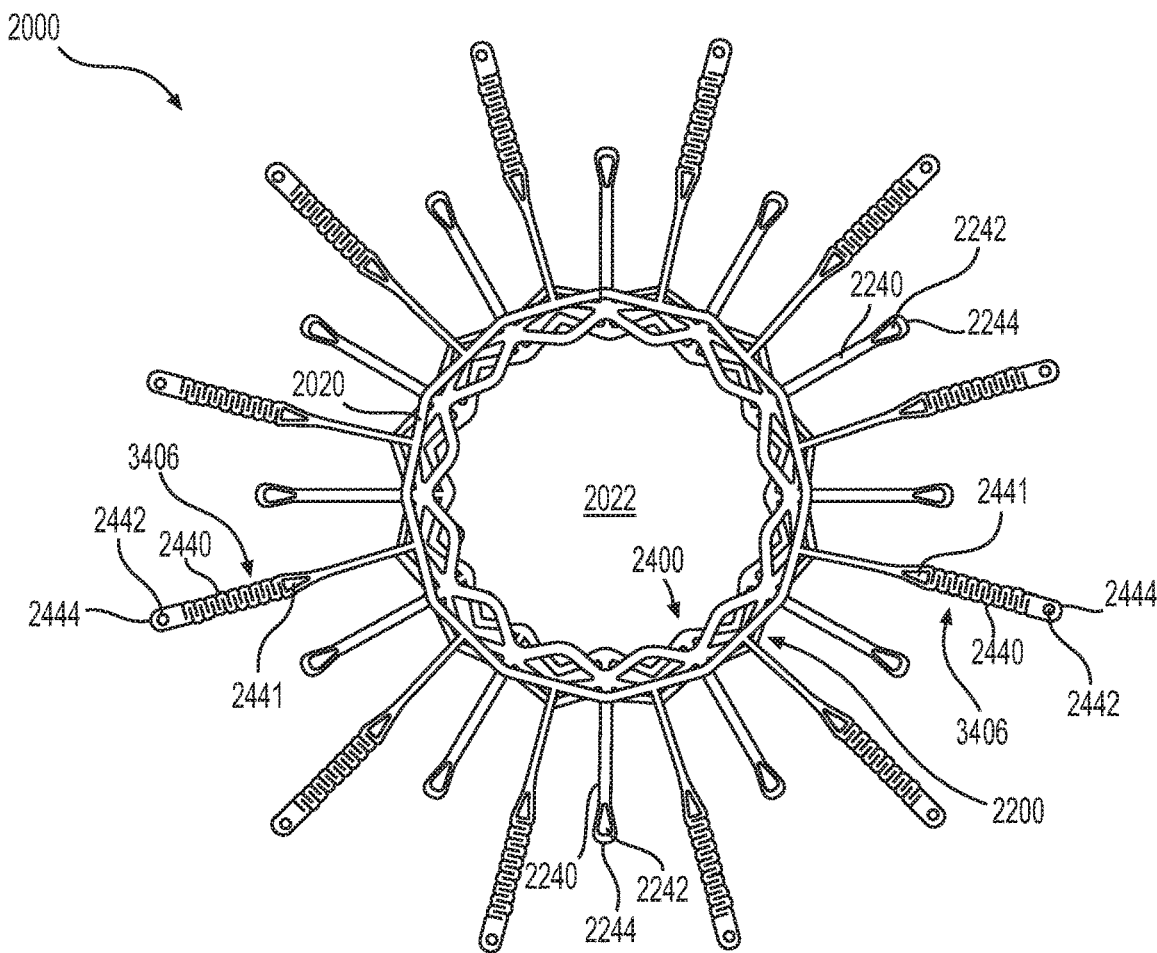
FIG. 2B illustrates a top plan view of the exemplary frame of FIG. 2A, consistent with various embodiments of the present disclosure.

FIG. 2A illustrates a front view of another exemplary frame 2000 for a prosthetic valve. FIG. 2B illustrates a top plan view of the frame 2000. Frame 2000 may include an annular outer frame 2200 and an inner frame 2400 situated at least partially within the annular outer frame 2200. Annular outer frame 2200 and inner frame 2400 may be secured together by pins, screws, welding, soldering, adhesive, magnets, and/or any other suitable mechanism. For example, FIGS. 2A and 2B depict annular outer frame 2200 and inner frame 2400 connected by a plurality of connector pins 2040.

Annular outer frame 2200 may include an outer frame tubular portion 3605, which may be formed of a plurality of struts intersecting at junctions to form a wire mesh, stent-like, or cage-like structure of the outer frame tubular portion 3605. For example, as illustrated in FIG. 2A, annular outer frame 2200 may include outer frame atrial circumferential struts 3608a, outer frame leg base struts 3608b, and outer frame ventricular circumferential struts 3608c intersecting at atrial end outer frame junctions 3602, leg attachment junctions 3802, outer frame junctions 3804, and ventricular end outer frame junctions 3604 to form outer frame tubular portion 3605. Annular outer frame 2200 may also include at least one ventricular anchoring leg 2240, which may extend from leg attachment junction 3802 of the outer frame tubular portion 3605 and which may be configured to engage ventricular tissue of a native valve to anchor the prosthetic valve in the native valve. The at least one ventricular anchoring leg 2240 may include a proximal leg end 3622, which may be the end of the leg connected to the outer frame tubular portion, and a distal leg end 2244, which may be situated radially outward from the outer frame tubular portion. As shown in FIG. 2B, the at least one ventricular anchoring leg 2240 may include at least one opening 2242.

Inner frame 2400 may include an inner frame tubular portion 3005, which may be formed of a plurality of struts intersecting at junctions to form a wire mesh, stent-like, or cage-like structure of the inner frame tubular portion 3005. For example, as illustrated in FIG. 2A, inner frame 2400 may include inner frame atrial struts 3008a, inner frame intermediate struts 3008b, and inner frame ventricular struts 3008c intersecting at atrial end inner frame junctions 3002, arm attachment junctions 3202, inner frame strut junctions 3204, and ventricular end inner frame junctions 3004 to form inner frame tubular portion 3005. Inner frame 2400 may also include at least one atrial anchoring arm 2440, which may extend from arm attachment junction 3202 of the inner frame tubular portion 3005 and which may be configured to engage atrial tissue of a native valve to anchor the prosthetic valve in the native valve. The at least one atrial anchoring arm 2440 may include a proximal arm end 3020, which may be the end of the arm connected to the inner frame tubular portion, and a distal arm end 2444, which may be situated radially outward from the inner frame tubular portion. As shown in FIG. 2B, the at least one atrial anchoring arm 2440 may include a proximal arm opening 2441 and a distal arm opening 2442.

Outer frame tubular portion 3605 and inner frame tubular portion 3005 may together form an annular valve body 2020 of the prosthetic valve, which may have at least one opening and from which the ventricular anchoring legs 2240 and atrial anchoring arms 2440 may extend. Annular valve body 2020 may include an axial lumen 2022 extending through the annular valve body 2020 along a longitudinal axis 2800 of the prosthetic valve. Annular valve body 2020 may have an atrial end 2024, a ventricular end 2025 opposite the atrial end, and an intermediate portion 2026 extending between the atrial and ventricular ends. In some embodiments, the atrial end may refer to the portion of the annular valve body configured to be situated at a location within the atrium that is furthest from an adjacent ventricle, when the prosthetic valve is implanted in a native valve. Similarly, the ventricular end may refer to the portion of the annular valve body configured to be situated at a location within the ventricle that is furthest from an adjacent atrium, when the prosthetic valve is implanted in a native valve. The intermediate portion 2026 may extend between the atrial end 2024 and ventricular end 2025. In some embodiments, annular valve body 2020 may include one or more ventricular end delivery posts 1028 along the ventricular end 2025 of the annular valve body. Axial lumen 2022 may include an inlet opening 2032 at the atrial end of the annular valve body, as well as an outlet opening 2036 at the ventricular end of the annular valve body.

Figure 2C:
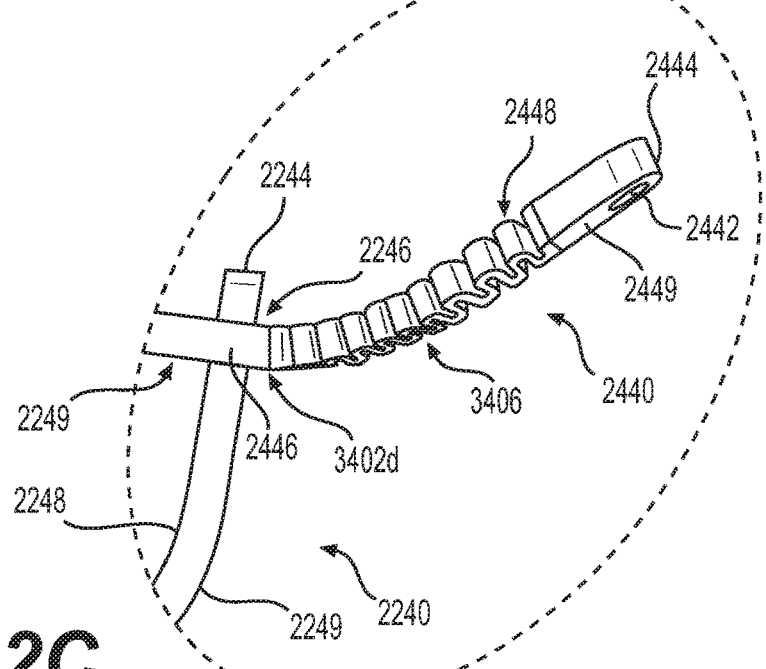
FIG. 2C illustrates an enlarged view of an atrial anchoring arm and a ventricular anchoring leg of the exemplary frame of FIG. 2A, consistent with various embodiments of the present disclosure.

FIG. 2C illustrates an enlarged view of an atrial anchoring arm 2440 and a ventricular anchoring leg 2240 of frame 2000. Ventricular anchoring leg 2240 may include an inner, atrially-facing leg surface 2248 and an outer, ventricularly-facing leg surface 2249. Atrial anchoring arm 2440 may include an atrially-facing arm surface 2448 and a ventricularly-facing arm surface 2449. In some embodiments, atrial anchoring arm 2440 may include an arm portion 2446 configured to be arranged in a common lateral plane with leg portion 2246 of the ventricular anchoring leg 2240. That is, leg portion 2246 and arm portion 2446 may be positioned at the same axial position along longitudinal axis 2800.

Figure 2D:
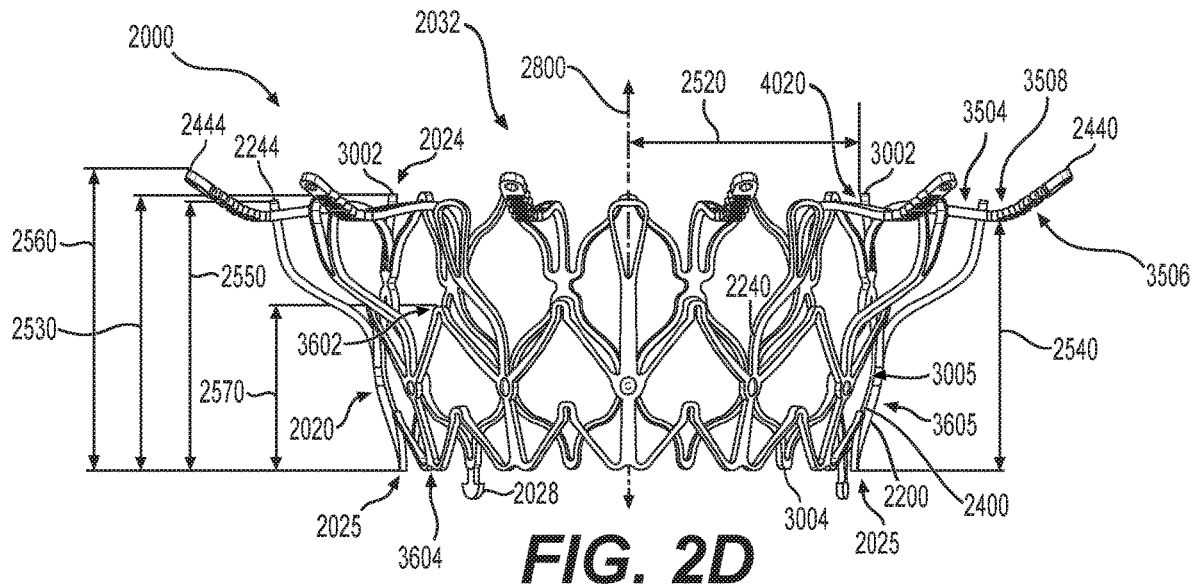
FIG. 2D illustrates another front elevation view of the exemplary frame of FIG. 2A, consistent with various embodiments of the present disclosure.

FIG. 2D illustrates another front elevation view of frame 2000. The exemplary prosthetic valve, as well as frame 2000, may have an axial height 2560, which may extend between terminal arm ends 2444 and ventricular end 2025 of the annular valve body. Inner frame tubular portion 3005 may have an axial height 2530, which may extend between atrial end inner frame junctions 3002 and ventricular end inner frame junctions 3004. Annular outer frame 2200 may have an axial height 2550, which may extend between terminal leg ends 2244 and ventricular end 2025 of the annular valve body. Outer frame tubular portion 3605 may have an axial height 2570, which may extend between atrial end outer frame junctions 3602 and ventricular end outer frame junctions 3604. In some embodiments, frame 2000 may have a ventricular device protrusion distance 2540, which may represent the distance over which the prosthetic valve protrudes into a left ventricle when the prosthetic valve is implanted in a native mitral valve. Annular valve body 2020 may include a valve inlet radius 2520, which may be the radius of atrial inlet opening 2032.

Figure 2E:
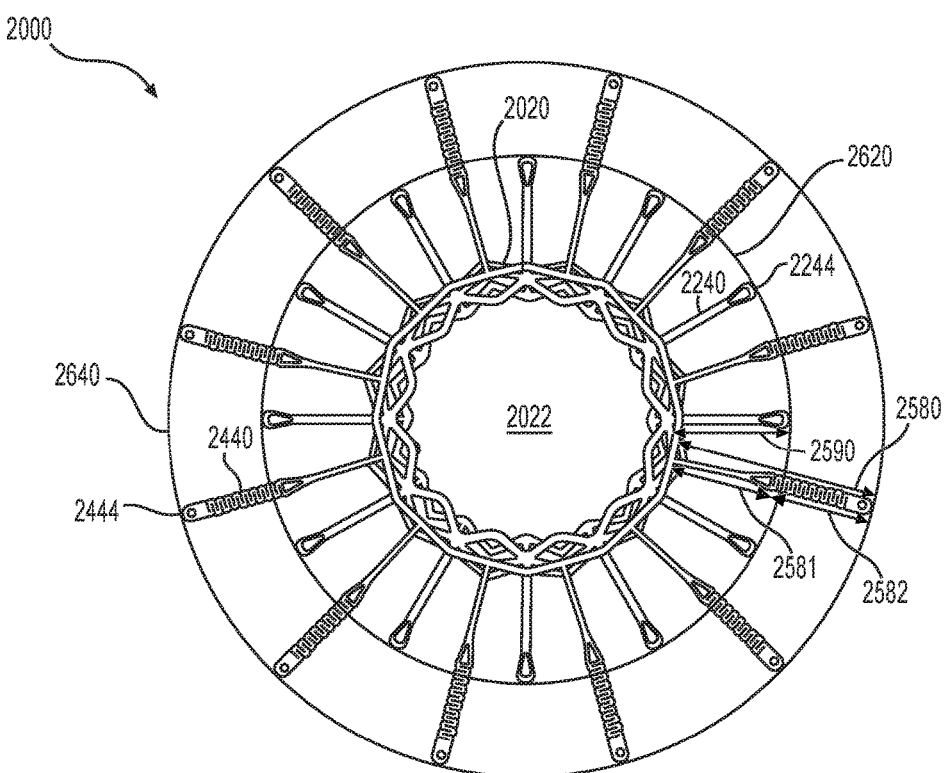
FIG. 2E illustrates another top plan view of the exemplary frame of FIG. 2A, consistent with various embodiments of the present disclosure.

FIG. 2E illustrates another top plan view of frame 2000. The atrial anchoring arms 2440 may have a length 2580, and the ventricular anchoring legs 2240 may have a length 2590. The terminal arm ends 2444 may define an atrial anchoring arm circumference 2640. The terminal leg ends 2244 may define a ventricular anchoring leg circumference 2620, which may be concentric with atrial anchoring arm circumference 2640. Inflexible portions 3402 of the atrial anchoring arms (illustrated in FIG. 3B) may have a length 2581. Serpentine structures 3406 of the atrial anchoring arms (illustrated in FIG. 3B) may have a length 2582.

Figure 3A:
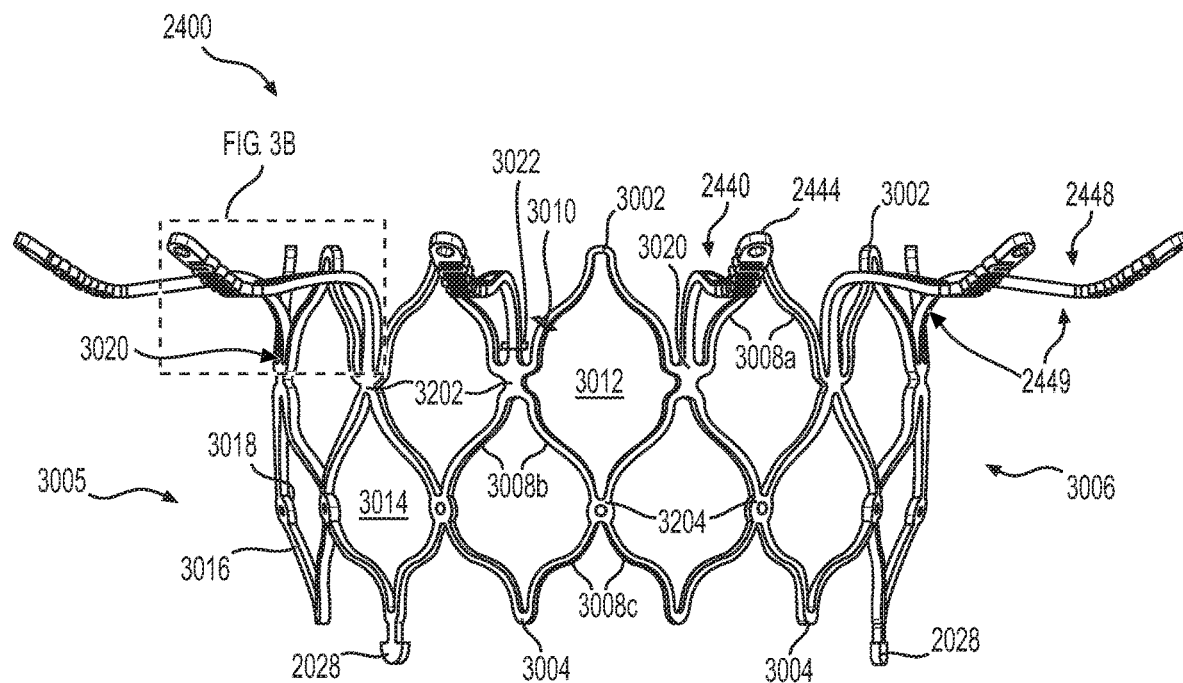
FIG. 3A illustrates a front elevation view of an inner frame of the exemplary frame of FIG. 2A, consistent with various embodiments of the present disclosure.

FIG. 3A illustrates a front elevation view of inner frame 2400. The atrial end inner frame junctions 3002 and ventricular end inner frame junctions 3004 may form the atrial end and ventricular end, respectively, of inner frame 2400. Inner frame intermediate portion 3006 may extend between atrial end inner frame junctions 3002 and ventricular end inner frame junctions 3004. Inner frame tubular portion 3005 may have a radially inner surface 3018 and a radially outer surface 3016. Inner frame atrial struts 3008a and inner frame intermediate struts 3008b may intersect at atrial end inner frame junctions 3002, arm attachment junctions 3202, and strut junctions 3204 to form a first, atrial row of closed cells 3012. Inner frame intermediate struts 3008b and inner frame ventricular struts 3008c may intersect at arm attachment junctions 3202, strut junctions 3204, and ventricular end inner frame junctions 3004 to form a second, ventricular row of closed cells 3014. At least one inner frame atrial strut 3008a may have a cross-sectional area 3010. At least one atrial anchoring arm 2440 may have a cross-sectional area 3022.

Figure 3B:
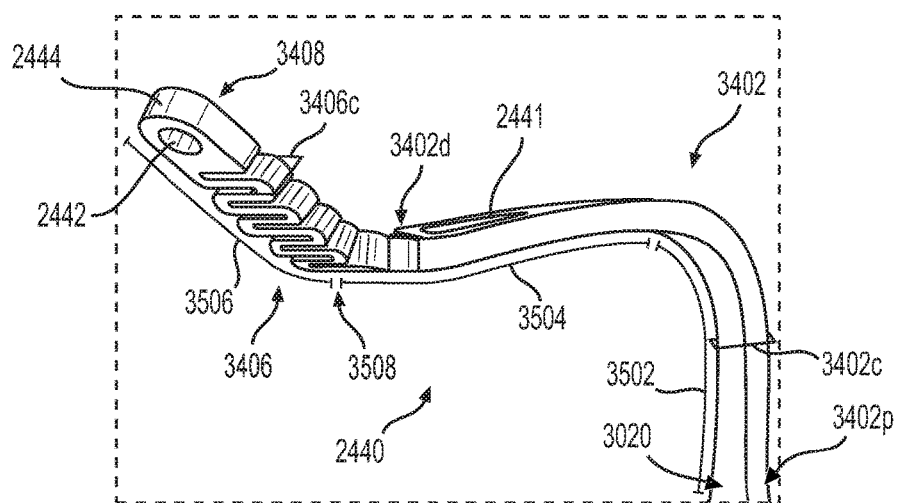
FIG. 3B illustrates an enlarged view of an atrial anchoring arm of the exemplary inner frame of FIG. 3A, consistent with various embodiments of the present disclosure.

FIG. 3B illustrates an enlarged view of an atrial anchoring arm 2440 of inner frame 2400. Atrial anchoring arm 2440 may include a proximal arm portion 3502 configured to extend in an atrial direction, intermediate arm portion 3504 configured to extend in a ventricular direction, and distal arm portion 3506 configured to extend in an atrial direction. Arm transition portion 3508 may represent the transition between intermediate arm portion 3504 and distal arm portion 3506. Atrial anchoring arm 2440 may also include an inflexible portion 3402 extending to proximal arm end 3020, as well as a serpentine structure 3406, which may be situated radially external to the inflexible portion 3402. Inflexible portion 3402 may have a proximal end 3402p, a distal end 3402d, and a cross-sectional area 3402c. Serpentine structure 3406 may have a cross-sectional area 3406c. In some embodiments, atrial anchoring arm 2440 may include a terminal arm region 3408 situated radially external to serpentine structure 3406. Distal arm opening 2442 may be situated within terminal arm region 3408.

Figure 3C:
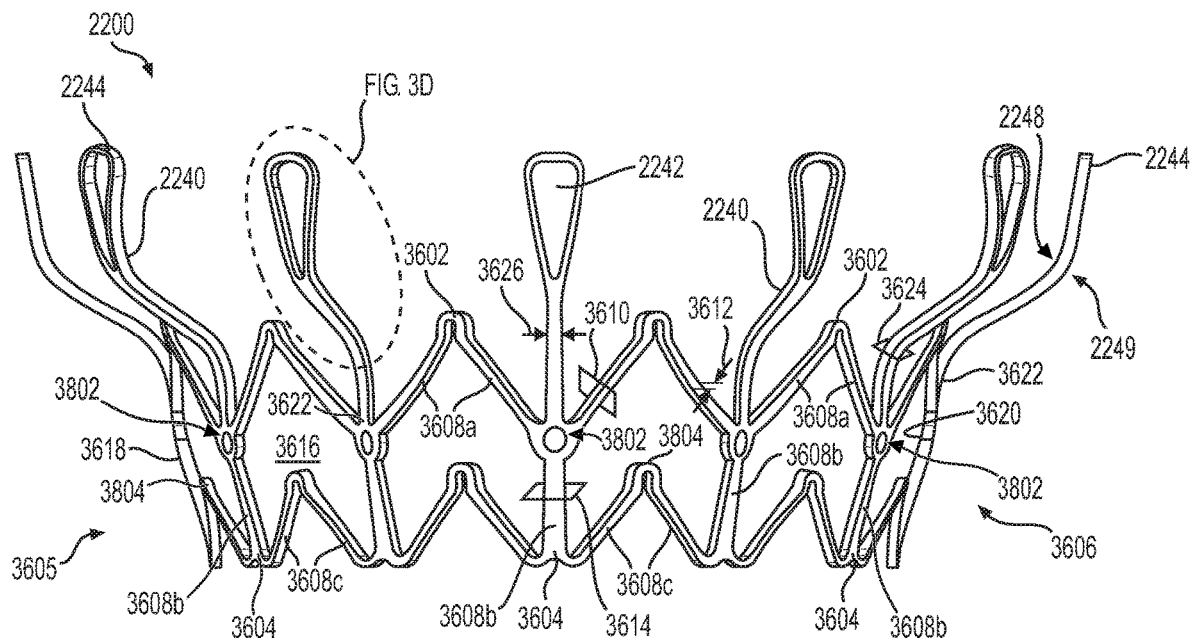
FIG. 3C illustrates a front elevation view of an outer frame of the exemplary frame of FIG. 2A, consistent with various embodiments of the present disclosure.

FIG. 3C illustrates a front elevation view of outer frame 2200. The atrial end outer frame junctions 3602 and ventricular end outer frame junctions 3604 may form the atrial end and ventricular end, respectively, of annular outer frame 2200. Outer frame intermediate portion 3606 may extend between atrial end outer frame junctions 3602 and ventricular end outer frame junctions 3604. Outer frame tubular portion 3605 may have a radially outer surface 3618 and a radially inner surface 3620. The outer frame atrial circumferential struts 3608a, outer frame leg base struts 3608b, and outer frame ventricular circumferential struts 3608c may intersect at the atrial end outer frame junctions 3602, leg attachment junctions 3802, outer frame junctions 3804, and ventricular end outer frame junctions 3604 to form closed cells 3616. At least one outer frame atrial circumferential strut 3608a may have a cross-sectional area 3610 and a width 3612. At least one outer frame leg base strut 3608b may have a cross-sectional area 3614. At least one ventricular anchoring leg may have a cross-sectional area 3624 and a radially outer surface width 3626.

Figure 3D:
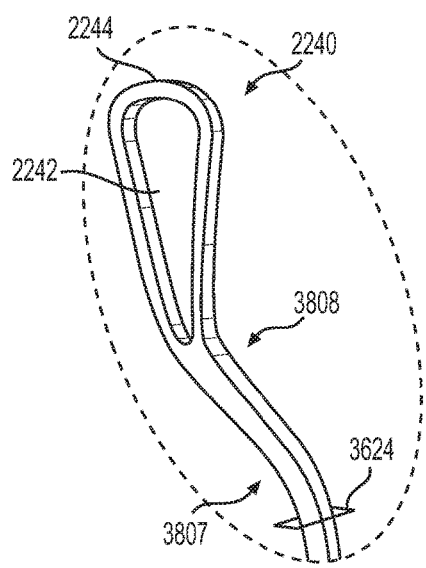
FIG. 3D illustrates an enlarged view of a ventricular anchoring leg of the exemplary outer frame of FIG. 3C, consistent with various embodiments of the present disclosure.

FIG. 3D illustrates an enlarged view of a portion of a ventricular anchoring leg 2240 of annular outer frame 2200. Ventricular anchoring leg 2240 may include a first, proximal curved portion 3807 and a second, distal curved portion 3808. In some embodiments, proximal curved portion 3807 may face radially outward. Additionally, or alternatively, distal curved portion 3808 may face radially inwards.

Figure 4B:
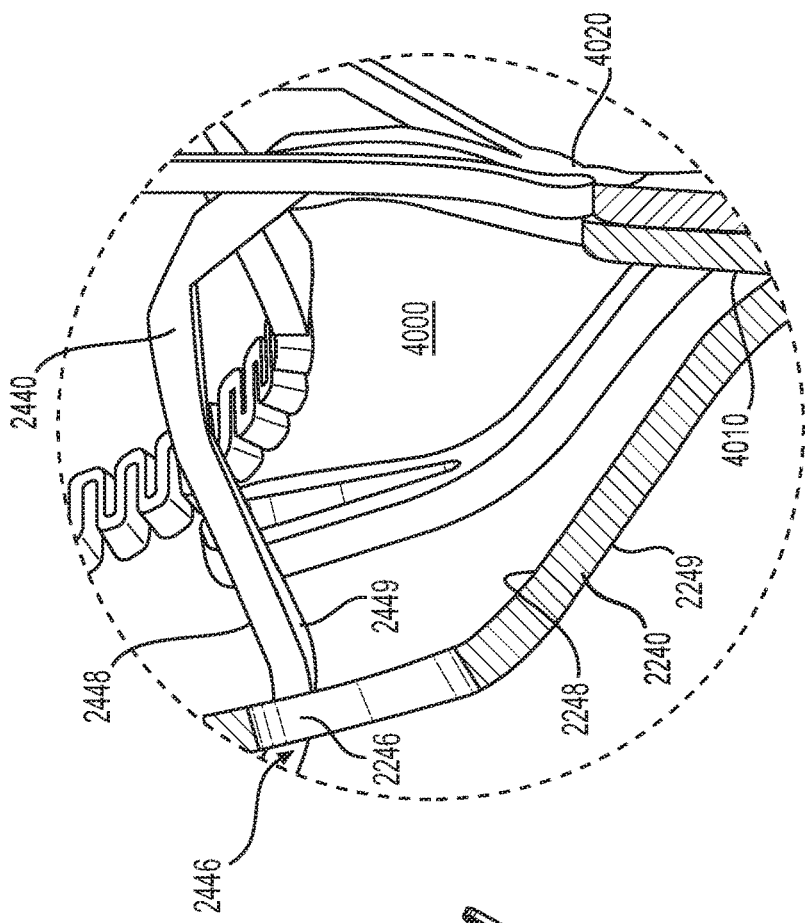
FIG. 4B illustrates an enlarged view of a volume between an atrial anchoring arm and a ventricular anchoring leg of the exemplary frame of FIG. 4A, consistent with various embodiments of the present disclosure.
Figure 4A:
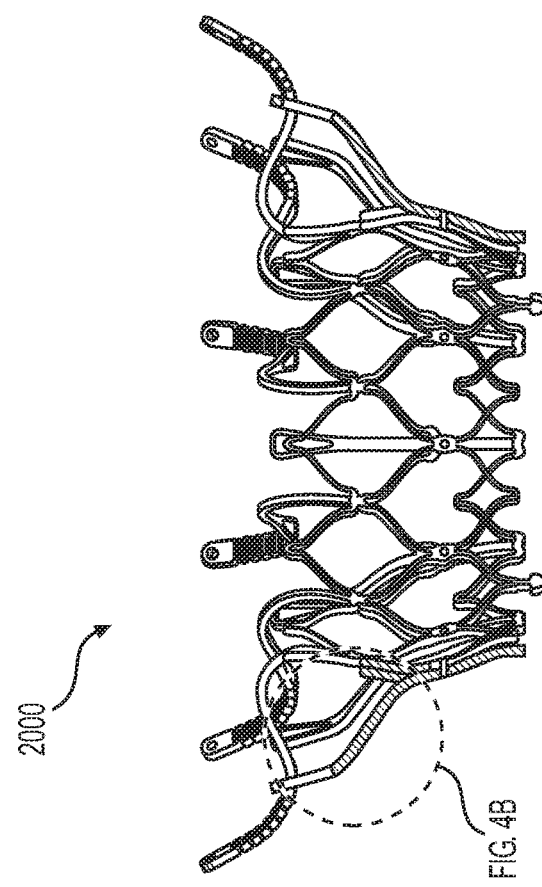
FIG. 4A illustrates a cross-sectional view of the exemplary frame of FIG. 2A, consistent with various embodiments of the present disclosure.

FIG. 4A illustrates a cross-sectional view of frame 2000, and FIG. 4B illustrates an enlarged view of a portion of FIG. 4A depicting a volume 4000 formed between the atrial anchoring arms 2440 and ventricular anchoring legs 2240. FIG. 4B also depicts an outer surface 4010 and inner surface 4020 of annular valve body 2020. In some embodiments, volume 4000 may be bounded by the ventricularly-facing surfaces 2449 of atrial anchoring arms 2440, by the inner, atrially-facing surfaces 2248 of ventricular anchoring legs 2240, and by the outer surface 4010 of the annular valve body 2020.

FIG. 5A illustrates a configuration of the exemplary prosthetic valve in which annular valve body 2020, atrial anchoring arms 2440, and ventricular anchoring legs 2240 are arranged in a radially-contracted configuration. In some embodiments, the configuration illustrated in FIG. 5A may constitute a radially-contracted configuration of the prosthetic valve.

FIG. 5B illustrates a configuration of the exemplary prosthetic valve in which annular valve body 2020 and atrial anchoring arms 2440 are arranged in a radially-contracted configuration. In the configuration of FIG. 5B, the ventricular anchoring legs 2240 may deflect radially outward away from annular valve body 2020, into a radially-expanded configuration of the ventricular anchoring legs 2240.

FIG. 5C illustrates a configuration of the exemplary prosthetic valve in which annular valve body 2020 and ventricular anchoring legs 2240 are arranged in a radially-contracted configuration. In the configuration of FIG. 5C, the atrial anchoring arms 2440 may deflect radially outward away from annular valve body 2020, into a radially-expanded configuration of the atrial anchoring arms 2440.

FIG. 5D illustrates a configuration of the exemplary prosthetic valve in which the atrial anchoring arms 2440 and ventricular anchoring legs 2240 may deflect radially outward away from annular valve body 2020 into their respective radially-expanded configurations, while annular valve body 2020 remains in a radially-contracted configuration. In the configuration of FIG. 5D, an axial distance 5004 may be formed between the atrial anchoring arms 2440 and the terminal ends 2244 of the ventricular anchoring legs 2240.

FIG. 5E illustrates a configuration of the exemplary prosthetic valve in which annular valve body 2020, atrial anchoring arms 2440, and ventricular anchoring legs 2240 are arranged in a radially-expanded configuration. In some embodiments, the configuration illustrated in FIG. 5E may constitute a radially-expanded configuration of the prosthetic valve.

Figure 6A:
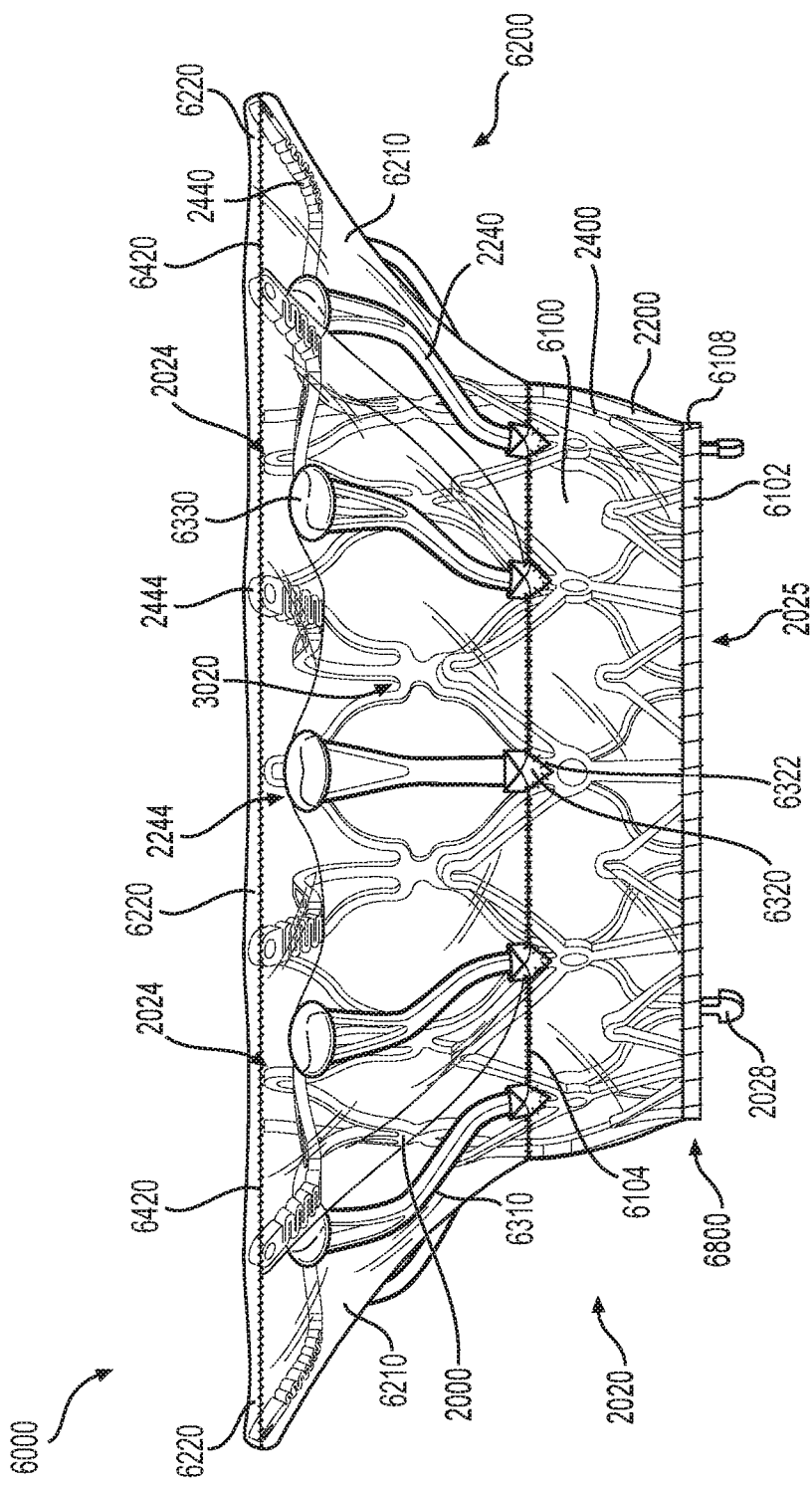
FIG. 6A illustrates a front elevation view of an exemplary prosthetic valve, consistent with various embodiments of the present disclosure.

FIG. 6A illustrates a front elevation view of prosthetic valve 6000. In some embodiments, prosthetic valve 6000 may be assembled upon frame 2000. Prosthetic valve 6000 may be configured for implantation within or near a native valve structure and may be configured to restore and/or replace the functionality of a native valve, such as a diseased or otherwise impaired native valve. Prosthetic valve 6000 may include valve frame 2000, including annular valve body 2020, the atrial anchoring arms 2440, and the ventricular anchoring legs 2240. Prosthetic valve 6000 may also include a skirt layer 6100 configured around an external surface of a portion of the annular valve body. Prosthetic valve 6000 may additionally include a first cuff sheet 6210, which may be connected to skirt layer 6100 via stitching 6104, as well as a second cuff sheet 6220, which may be connected to first cuff sheet 6210 via stitching 6420. In some embodiments, the first cuff sheet 6210 and second cuff sheet 6220 by extend around the terminal ends 2444 of the atrial anchoring arms 2440. Skirt layer 6100, first cuff sheet 6210, and second cuff sheet 6220 may be constructed of fluid-impermeable material and may accordingly be configured to prevent passage of blood or other fluids through portions of the prosthetic valve 6000 outside of the axial lumen 2022.

In some embodiments, prosthetic valve 6000 may additionally include a protective sleeve 6102 wrapped around the rim 6800 of the ventricular outlet opening of annular valve body 2020; protective sleeve 6102 may be secured to annular valve body 2020 by stitching 6108. Additionally, or alternatively, prosthetic valve 6000 may include at least one liner 6310 extending around an external surface of the ventricular anchoring legs 2240, with at least one protective layer 6330 positioned around the distal leg ends 2244 and at least one protective covering 6320 wrapped around the proximal leg ends 3622. In some embodiments, the at least one protective covering 6320 may be secured to the skirt layer 6100 via stitching 6322.

Figure 6B:
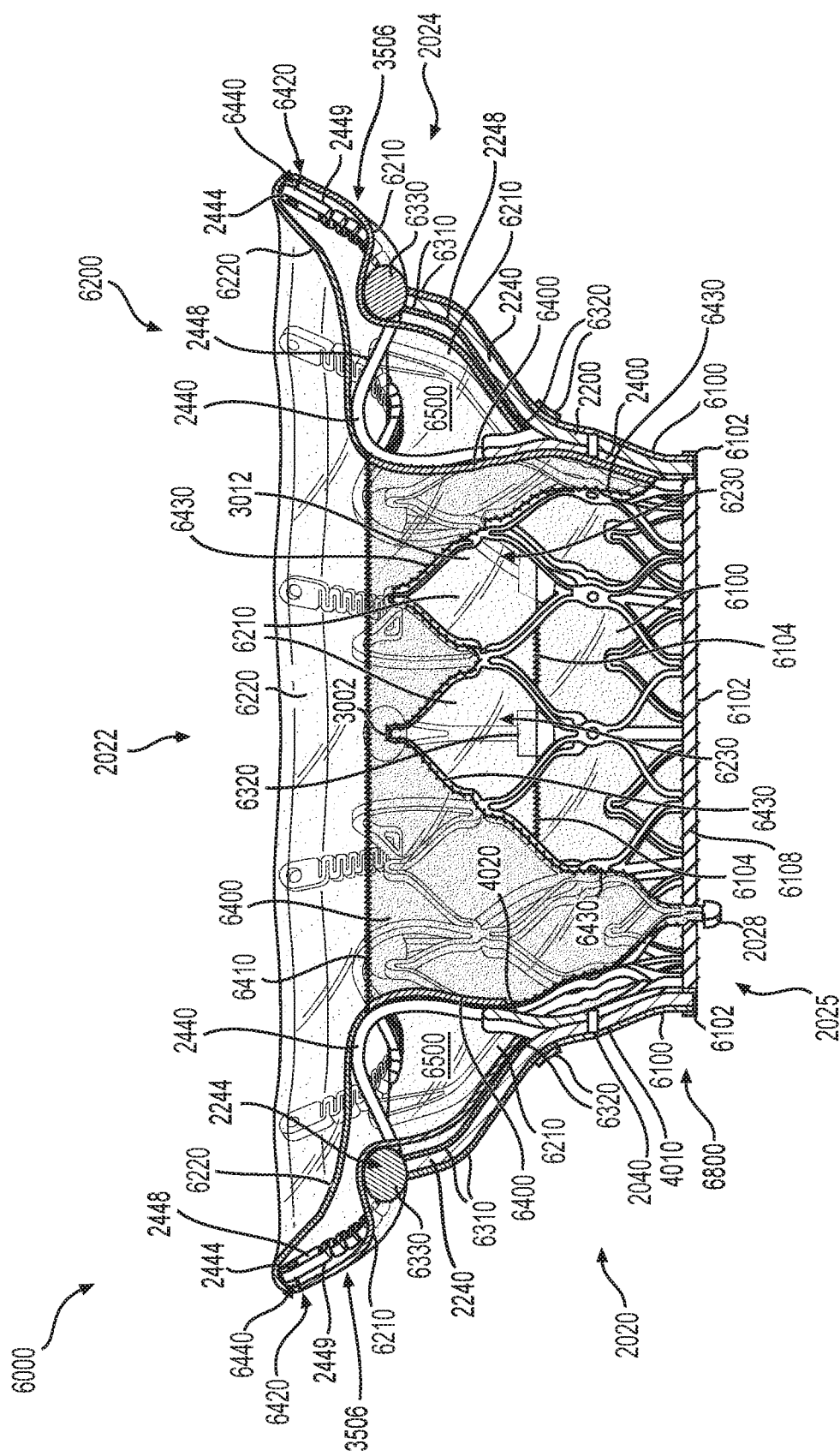
FIG. 6B illustrates a cross-sectional view of the exemplary prosthetic valve of FIG. 6A without leaflets, consistent with various embodiments of the present disclosure.

FIG. 6B illustrates a cross-sectional view of prosthetic valve 6000, without prosthetic leaflets situated within the axial lumen 2022. As illustrated in FIG. 6B, prosthetic valve 6000 may additionally include a liner 6400 covering at least a portion of the inner surface 4020 of the annular valve body 2020. Liner 6400 may be secured to the annular valve body 2020 via stitching 6430 and to the second cuff sheet 6220 via stitching 6410. First cuff sheet 6210, second cuff sheet 6220, and inner liner 6400 may together form an inflatable cuff 6200 having an interior volume 6500. In some embodiments, inflatable cuff 6200 may be secured to atrial anchoring arm 2440 via connector 6440. Blood may enter the cuff 6200 through openings 6230, causing the cuff 6200 to inflate radially outwards and axially in an atrial direction. In some embodiments, cuff 6200 may inflate radially outwards and press against tissue of the native valve. This engagement between the cuff and tissue of the native valve may form a barrier to flow of blood and other fluids around the outer circumference of the prosthetic valve 6000.

Figure 6C:
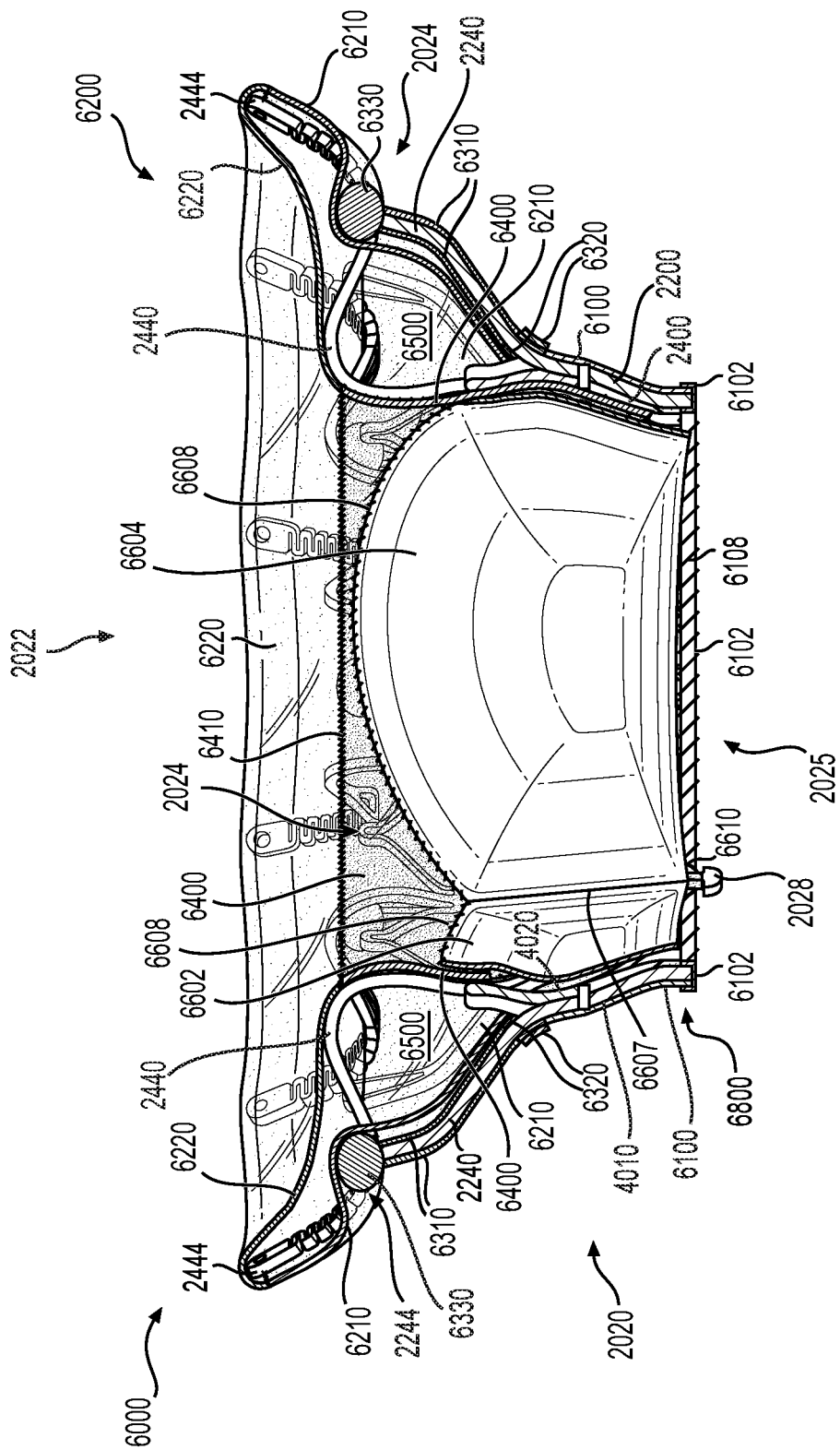
FIG. 6C illustrates a cross-sectional view of the exemplary prosthetic valve of FIG. 6A with leaflets, consistent with various embodiments of the present disclosure.

FIG. 6c illustrates a cross-sectional view of prosthetic valve 6000 with prosthetic leaflets 6602 and 6604 situated within the axial lumen 2022. In some embodiments, prosthetic valve 6000 may also include a third prosthetic leaflet 6606, which may not be visible in the view of FIG. 6C. The leaflets 6602, 6604, and 6606 may be secured to inner liner 6400 via stitching 6608 and may include a connector 6610 wrapping around the ventricular end delivery posts 2028 to secure the leaflets 6602, 6604, and 6606 to the valve frame 2000.

Figure 6D:
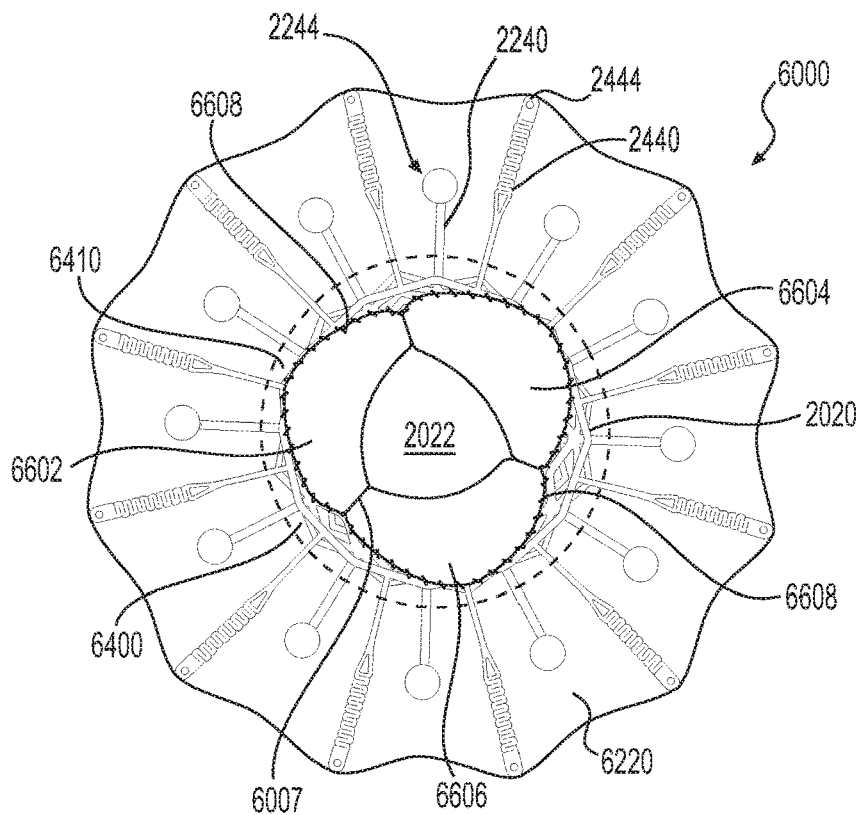
FIG. 6D illustrates a top plan view of the exemplary prosthetic valve of FIG. 6A with uninflated leaflets, consistent with various embodiments of the present disclosure.
Figure 6E:
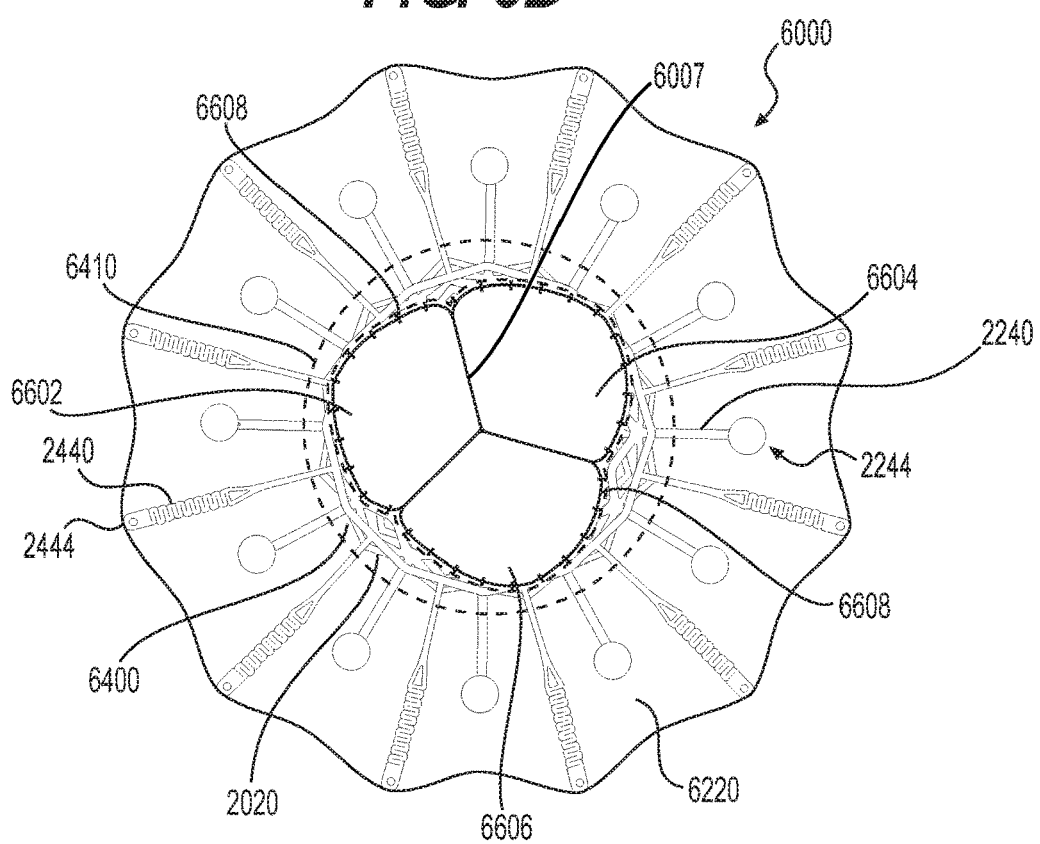
FIG. 6E illustrates a top plan view of the exemplary prosthetic valve of FIG. 6A with inflated leaflets, consistent with various embodiments of the present disclosure.

FIG. 6D illustrates a top plan view of prosthetic valve 6000, with leaflets 6602, 6604, and 6606 arranged in an open, uninflated configuration. In the open configuration, a space may be formed in the middle of the leaflets, permitting fluid to pass through the axial lumen 2022 of the prosthetic valve 6000. FIG. 6E illustrates a top plan view of prosthetic valve 6000, with leaflets 6602, 6604, and 6606 arranged in a closed, coapted configuration. In the closed configuration, the leaflets may press together such that the opening between them is closed. For example, the point of contact 6007 between two adjacent leaflets may extend to the center of the axial lumen; as a result, the leaflets may block fluid passage through the axial lumen 2022 of the prosthetic valve 6000.

Figure 7A:
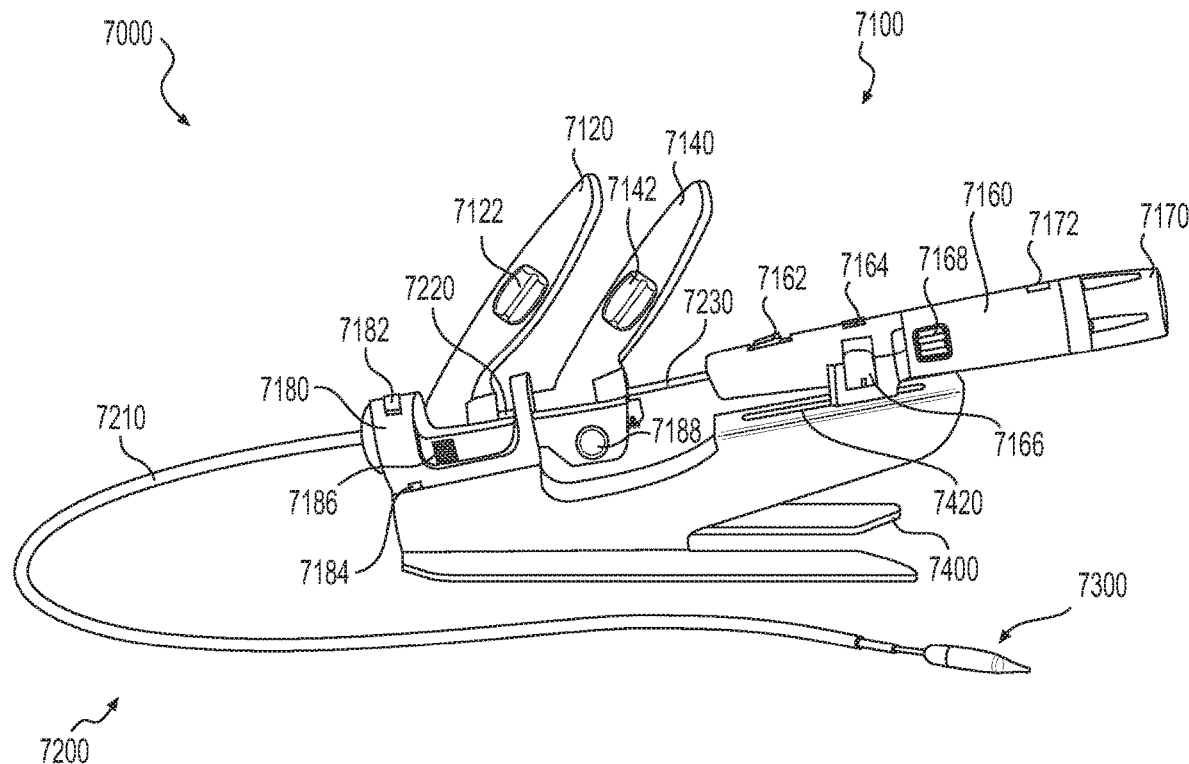
FIG. 7A illustrates an exemplary prosthetic valve delivery system, consistent with various embodiments of the present disclosure.

FIG. 7A illustrates a prosthetic valve delivery system 7000. Delivery system 7000 may be configured to deliver an implant prosthetic valve 6000 within a native valve, such as a native mitral valve. Prosthetic valve delivery system 7000 may include a control handle assembly 7100, a telescoping catheter assembly 7200, a delivery capsule 7300 configured to retain a prosthetic valve (e.g. valve 6000), and, optionally, a stand 7400.

Control handle assembly 7100 may include an outer sheath control handle 7120 having a steering knob 7122 configured to steer an outer sheath 7210 of the telescoping catheter assembly 7200. Control handle assembly 7100 may also include a guide catheter control handle 7140 having a steering knob 7142 configured to steer a guide catheter 7220 of the telescoping catheter assembly 7200.

Control handle assembly 7100 may also include an implant catheter control handle 7160 having a steering knob 7168 configured to steer an implant catheter 8100 of the telescoping catheter assembly 7200. Implant catheter control handle 7160 may also include a proximal capsule portion slider 7162, a distal capsule portion knob 7170, and a distal capsule portion knob lock 7172 configured to control release of the prosthetic valve 6000 from within delivery capsule 7300. Implant catheter control handle 7160 may also include a slide lock 7166 configured to lock the implant catheter control handle 7160 at a position within track 7420 of stand 7400.

Control handle assembly 7100 may also include a cradle 7180, which may be secured to stand 7400 via a locking mechanism that can be released by actuated of release button 7184. Cradle 7180 may include a rotation knob 7182 configured to control rotation of the outer sheath 7210 and guide catheter 7220. Cradle 7180 may also include a rotation knob 7186 configured to control rotation of the implant catheter 8100. Cradle 7180 may also include a knob 7188 configured to control relative axial movement between outer sheath control handle 7120 (which may be secured to outer sheath 7210) and guide catheter control handle 7140 (which may be secured to guide catheter 7220).

Figure 7B:
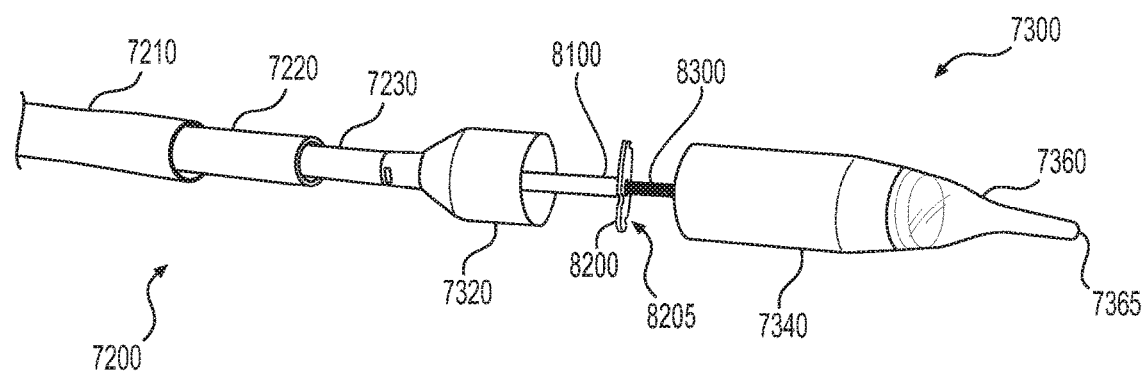
FIG. 7B illustrates an enlarged view of a delivery capsule of the exemplary prosthetic valve delivery system of FIG. 7A, consistent with various embodiments of the present disclosure.

FIG. 7B illustrates an enlarged view of delivery capsule 7300 of prosthetic valve delivery system 7000. Delivery capsule 7300 may include a proximal capsule portion 7320 and a distal capsule portion 7340 with a nose cone 7360 secured to the distal capsule portion 7340. A nose cone distal tip 7365 may form the distal end of the delivery capsule 7300. The telescoping catheter assembly 7200 may include a capsule shaft 7230 secured to, and configured to control movement of, the proximal capsule portion 7320 (e.g., due to connection 8400 between the capsule shaft 7230 and proximal capsule portion 7320, as illustrated in FIG. 8C). Implant catheter 8100 may extend within proximal capsule portion 7320 and may have a valve anchor disc 8200 connected to the distal end of the implant catheter 8100. A torque shaft 8300 may extend from the implant catheter 8100 and may be connected to distal capsule portion 7340; accordingly, torque shaft 8300 may be configured to control axial movement of the distal capsule portion 7340 relative to the implant catheter 8100 and valve anchor disc 8200. The proximal capsule portion 7320 and a distal capsule portion 7340 may be configured to retain prosthetic valve 6000, with the prosthetic valve 6000 secured against axial movement by valve anchor disc 8200. Control handle assembly 7100 may be configured to control movement of the proximal capsule portion 7320 and a distal capsule portion 7340, and thus may also control release of the prosthetic valve 6000 from within the delivery capsule 7300.

Figure 7D:
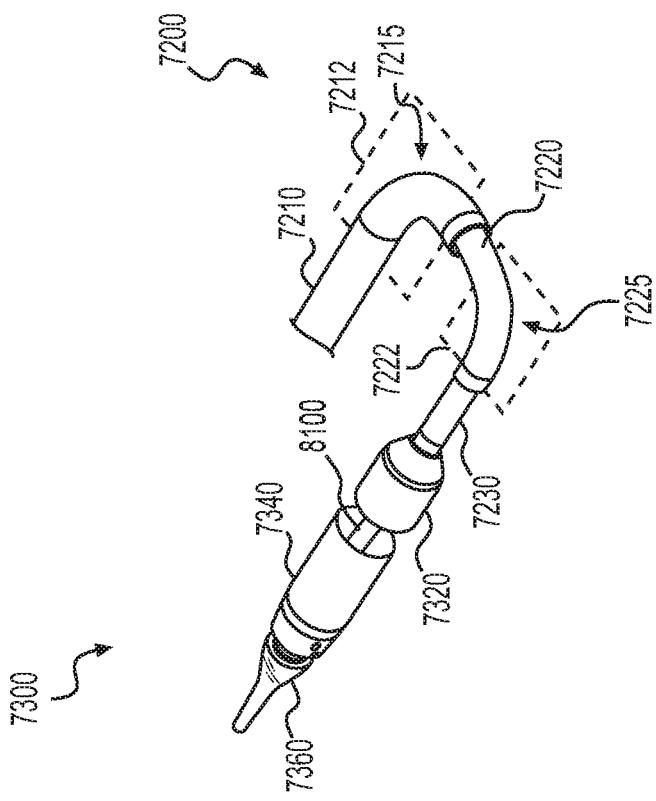
FIG. 7D illustrates another exemplary configuration of the telescoping catheter assembly and delivery capsule of FIG. 7C, consistent with various embodiments of the present disclosure.
Figure 7C:
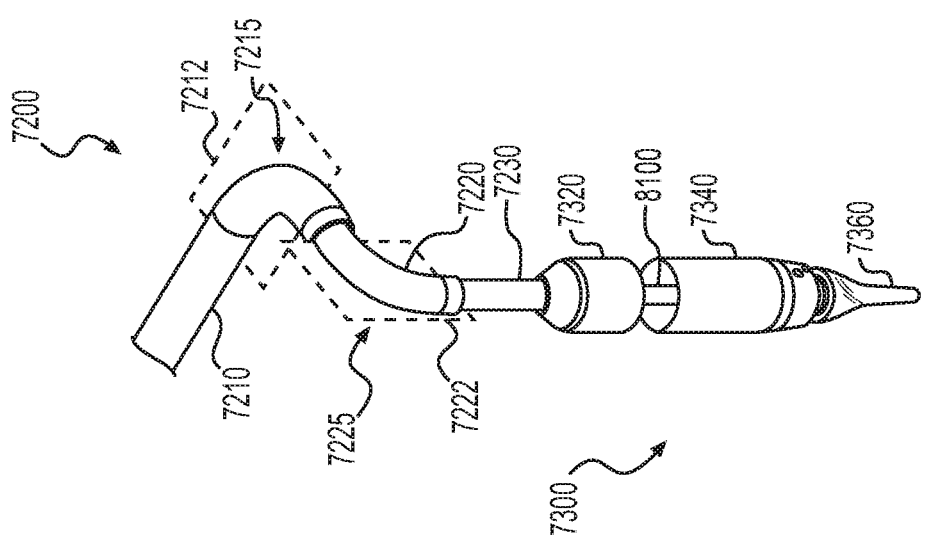
FIG. 7C illustrates an exemplary configuration of a telescoping catheter assembly and the delivery capsule of the exemplary prosthetic valve delivery system of FIG. 7A, consistent with various embodiments of the present disclosure.

FIGS. 7C and 7D illustrate exemplary configurations of the telescoping catheter assembly 7200. Outer sheath 7210 and guide catheter 7220 may include respective bending portions 7215 and 7225, at which the outer sheath 7210 and guide catheter 7220 may be configured to bend within their respective steering planes 7212 and 7222. In some embodiments, bending of the outer sheath 7210 within the first steering plane 7212 may be controlled by the outer sheath steering knob 7122 of the control handle assembly 7100. Additionally, or alternatively, bending of the guide catheter 7220 within the second steering plane 7222 may be controlled by the guide catheter steering knob 7142 of the control handle assembly 7100. In some embodiments, under control of the control handle assembly 7100, the outer sheath 7210, guide catheter 7220, and implant catheter 8100 may be steered so as to correctly position the delivery capsule 7300 within a native valve for implantation of the prosthetic valve.

Figure 8A:
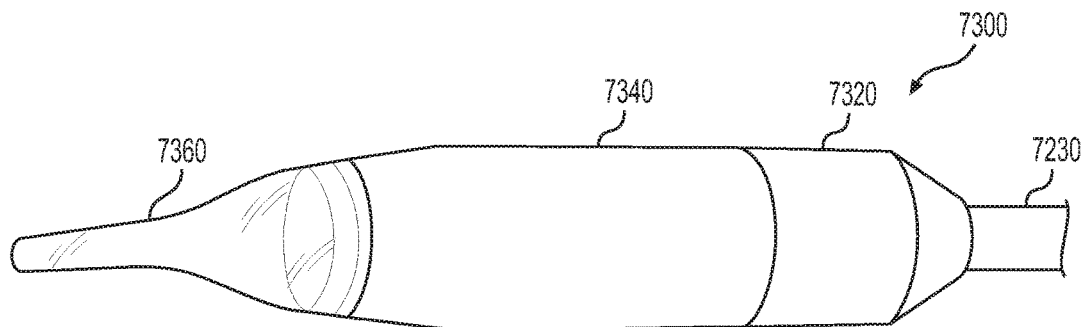
FIG. 8A illustrates another enlarged view of the exemplary delivery capsule of the prosthetic valve delivery system of FIG. 7A in a closed configuration, consistent with various embodiments of the present disclosure.
Figure 8B:
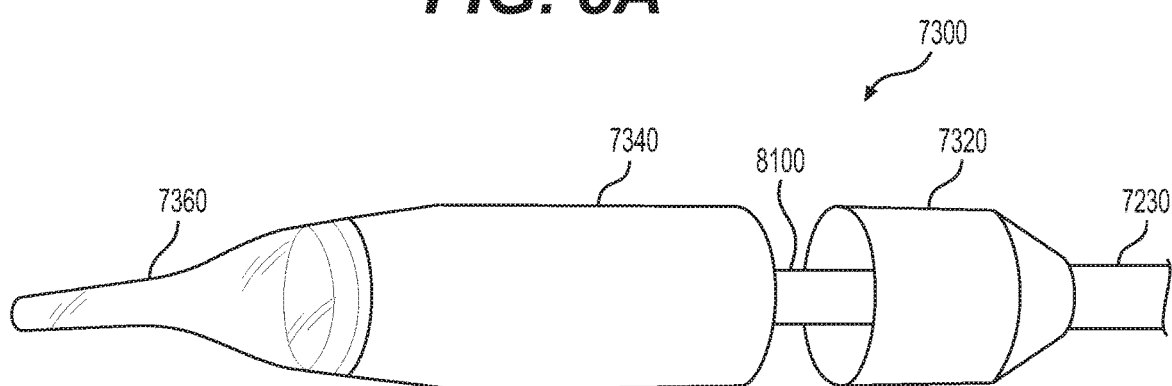
FIG. 8B illustrates the exemplary delivery capsule of FIG. 8A in an open configuration, consistent with various embodiments of the present disclosure.
Figure 8C:
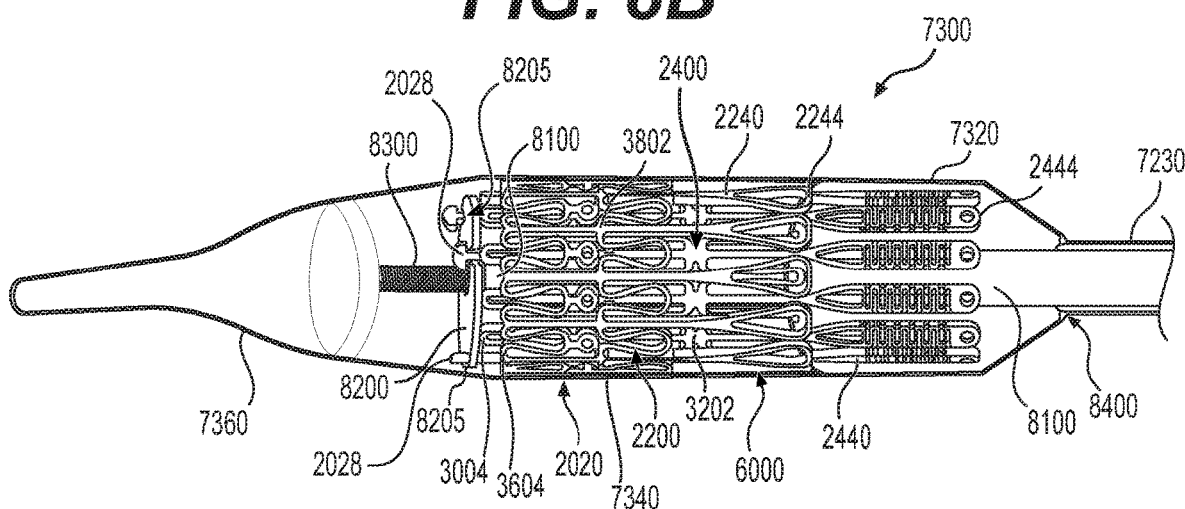
FIG. 8C illustrates an interior view of the exemplary delivery capsule of FIG. 8A in the closed configuration, consistent with various embodiments of the present disclosure.

FIG. 8A illustrates an enlarged view of delivery capsule 7300 in a closed configuration, while FIG. 8B illustrates an enlarged view of delivery capsule 7300 in an open configuration. In the closed configuration of FIG. 8A, the distal capsule portion 7340 and proximal capsule portion 7320 may be brought together to form an enclosed compartment in which prosthetic valve 6000 may be retained. In the open configuration of FIG. 8B, the distal capsule portion 7340 and proximal capsule portion 7320 may be drawn apart. In some embodiments, the delivery capsule 7300 may be configured such that the distal capsule portion 7340 and proximal capsule portion 7320 are moved apart from each other, the prosthetic valve 6000 may be sequentially deployed from within the delivery capsule and implanted within a native valve.

FIG. 8C illustrates an interior view of delivery capsule 7300 with prosthetic valve 6000 retained within the delivery capsule. Although only the valve frame 2000 of the prosthetic valve 6000 is illustrated in FIG. 8C, one of ordinary skill will understand that the entire prosthetic valve 6000 depicted in FIGS. 6A-6E may be retained within delivery capsule 7300 in the configuration illustrated in FIG. 8C.

In the embodiment illustrated in FIG. 8C, at least a portion of the annular valve body 2020 and ventricular anchoring legs 2240 of the prosthetic valve 6000 may be retained within the distal capsule portion. Additionally, or alternatively, at least a portion of atrial anchoring arms 2440 may be retained within proximal capsule portion 7320. In some embodiments, valve anchor disc 8200 may include a number of recesses 8205 configured to receive and retain the ventricular end delivery posts 2028 of the prosthetic valve 6000. For example, the valve anchor disc 8200 may include at least the same number of recesses 8205 as there are delivery posts 2028 of the prosthetic valve 6000. In some embodiments, the delivery posts 2028 may be retained within the recesses 8205 so long as the annular valve body 2020 remains in a radially-contracted configuration; the engagement between the valve anchor disc 8200 and delivery posts 2028 may secure the prosthetic valve 6000 against axial movement. Upon radial expansion of the annular valve body 2020, the delivery posts 2028 may slide or expand out of the recesses 8205, freeing the prosthetic valve 6000 from engagement with the valve anchor disc 8200.

Figure 9:
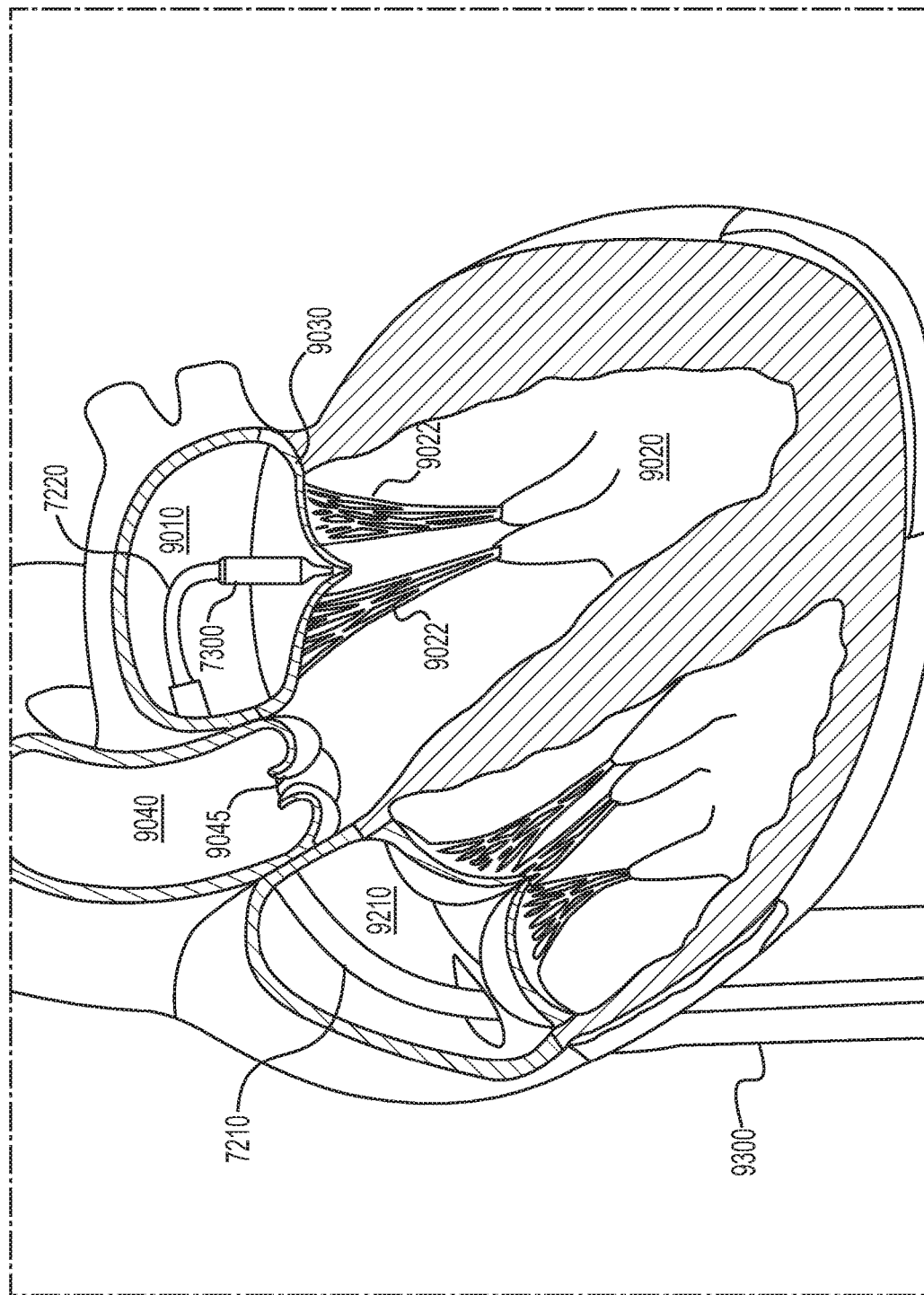
FIG. 9 illustrates advancement of the exemplary prosthetic valve delivery system of FIG. 7A into the left atrium, consistent with various embodiments of the present disclosure.

FIG. 9 illustrates one exemplary advancement route of the delivery capsule 7300 to the left atrium. In the example illustrated in FIG. 9, the delivery capsule 7300 may be steered through the vena cava into the right atrium 9210 and may pierce the interatrial septum and enter the left atrium 9010. Alternatively, the delivery capsule may be delivered to the heart by other routes. FIG. 9 also depicts the left ventricle 9020, the mitral valve 9030, the chordae tendineae 9022, the aortic valve 9045, and the aorta 9040.

Figure 10A:
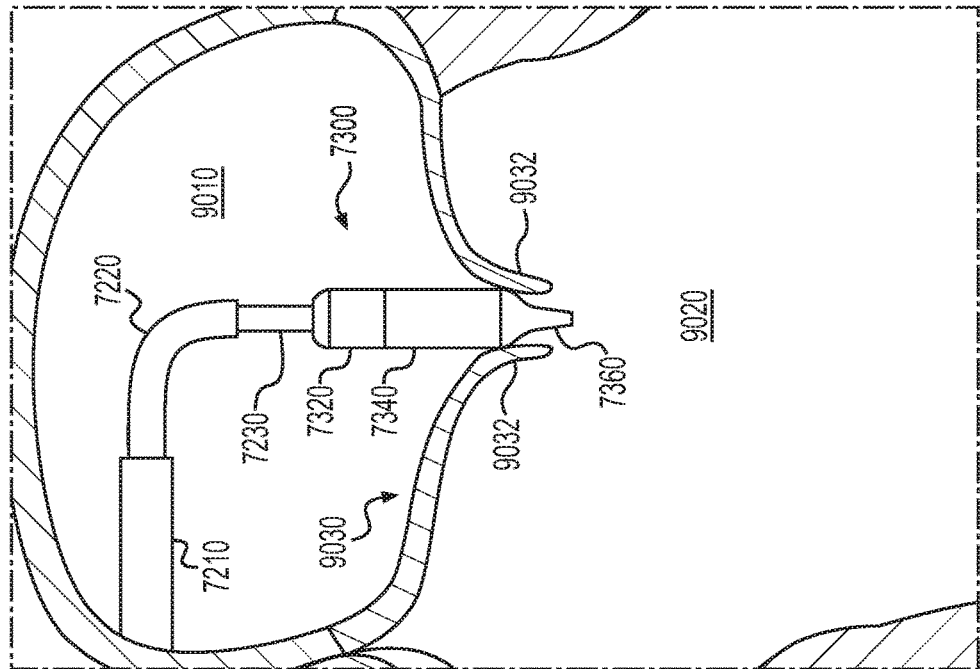
FIGS. 10A-10H depict implantation of the prosthetic valve of FIGS. 6A-6E within a native mitral valve by the exemplary prosthetic valve delivery system of FIG. 7A, consistent with various embodiments of the present disclosure.
Figure 10B:
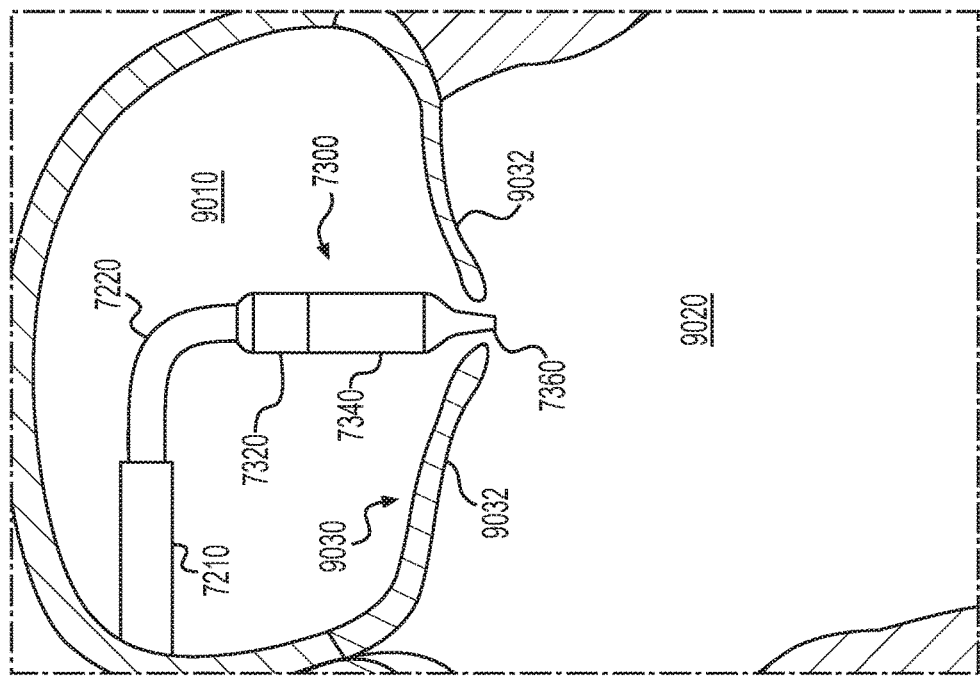
Figure 10D:
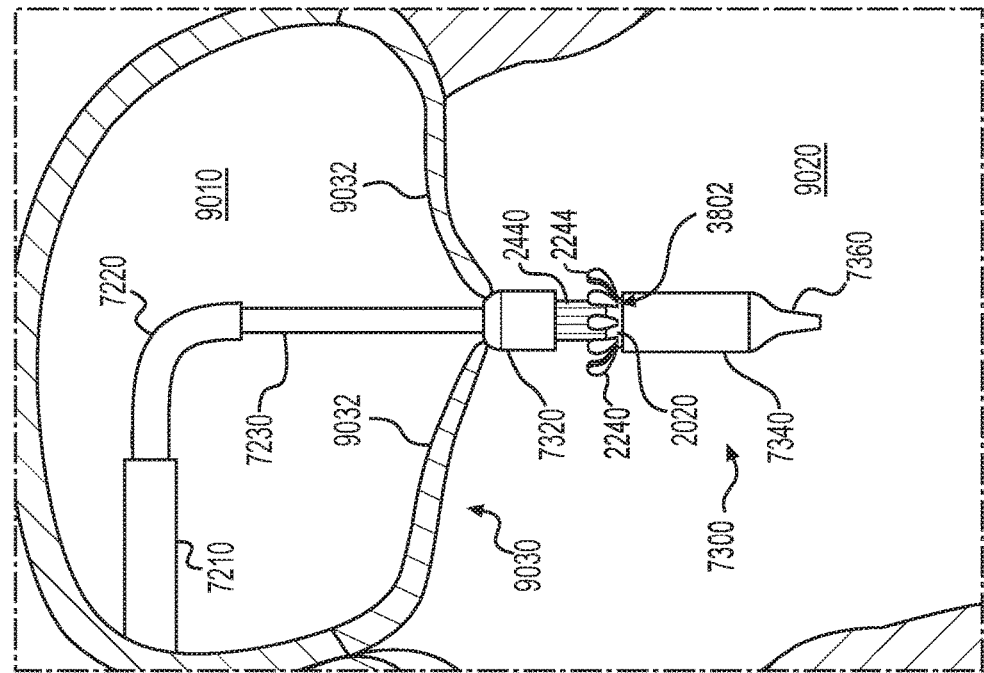
Figure 10C:
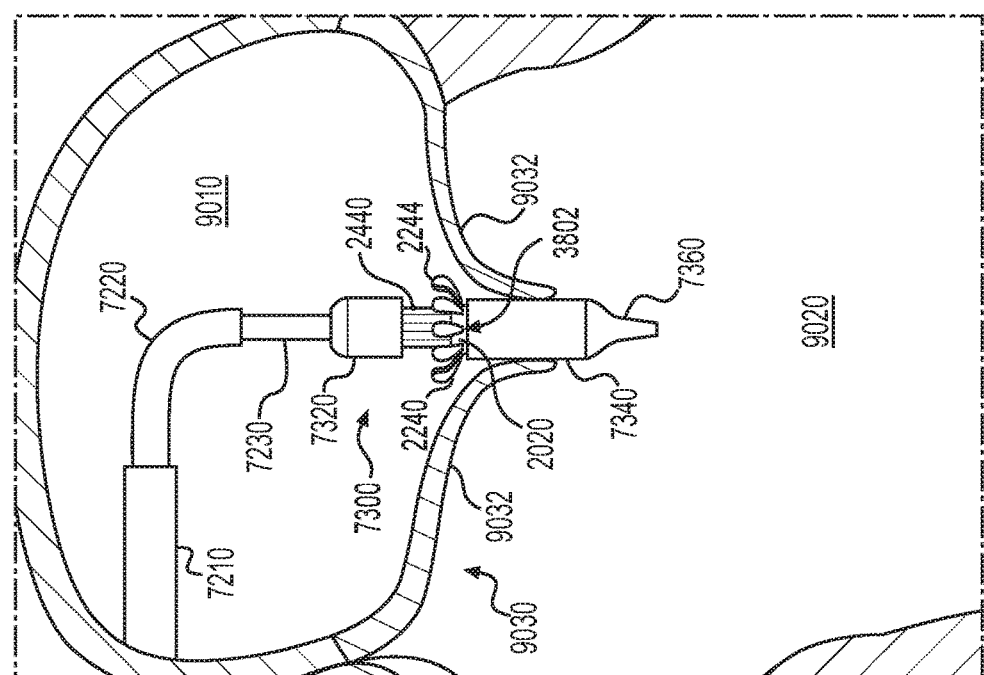

FIGS. 10A-10H depict an exemplary implantation method of prosthetic valve 6000 within a mitral valve 9030 including leaflets 9032. In FIG. 10A, the delivery capsule 7300 may be coaxially aligned with the mitral valve 9030. In some embodiments, the prosthetic valve 6000 may be held within the delivery capsule 7300 while the prosthetic valve is arranged in the configuration of FIG. 5A. In FIG. 10B, the delivery capsule 7300 may be distally advanced into the mitral valve 9030. In FIG. 10C, the distal capsule portion 7340 may be distally advanced relative to the rest of the delivery capsule 7300. This may release the ventricular anchoring legs 2240 from the distal capsule portion 7340, while the atrial anchoring arms 2440 and annular valve body 2020 remain constrained within the delivery capsule. In the example shown in FIG. 10C, the ventricular anchoring legs 2240 may be released from the delivery capsule 7300 within the atrium 9010. In some embodiments, the prosthetic valve 6000 may assume the configuration of FIG. 5B when the ventricular anchoring legs 2240 are released in the step depicted in FIG. 10C.

Figure 10F:
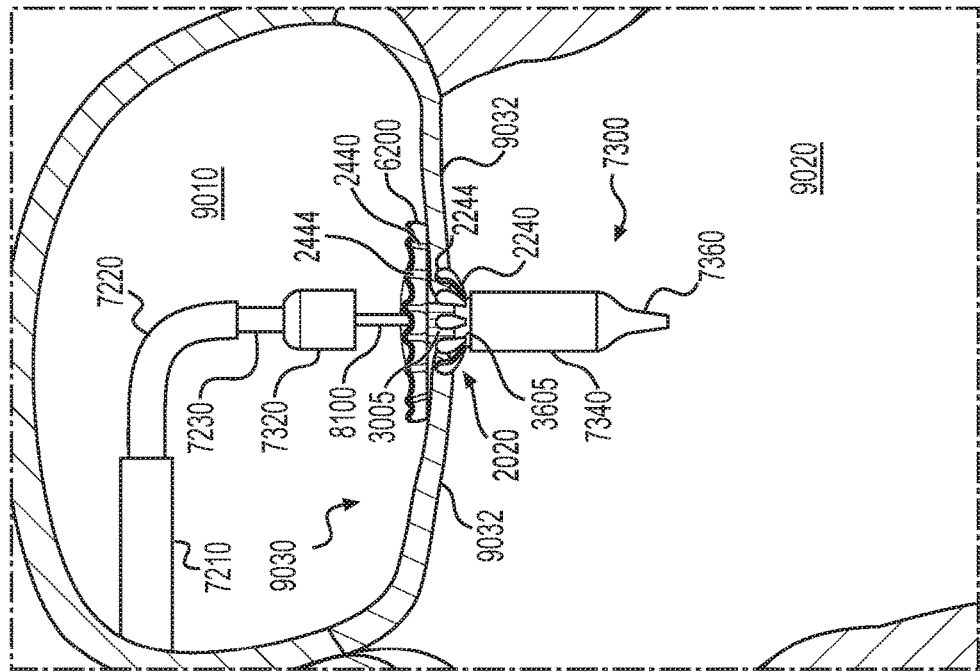
Figure 10E:
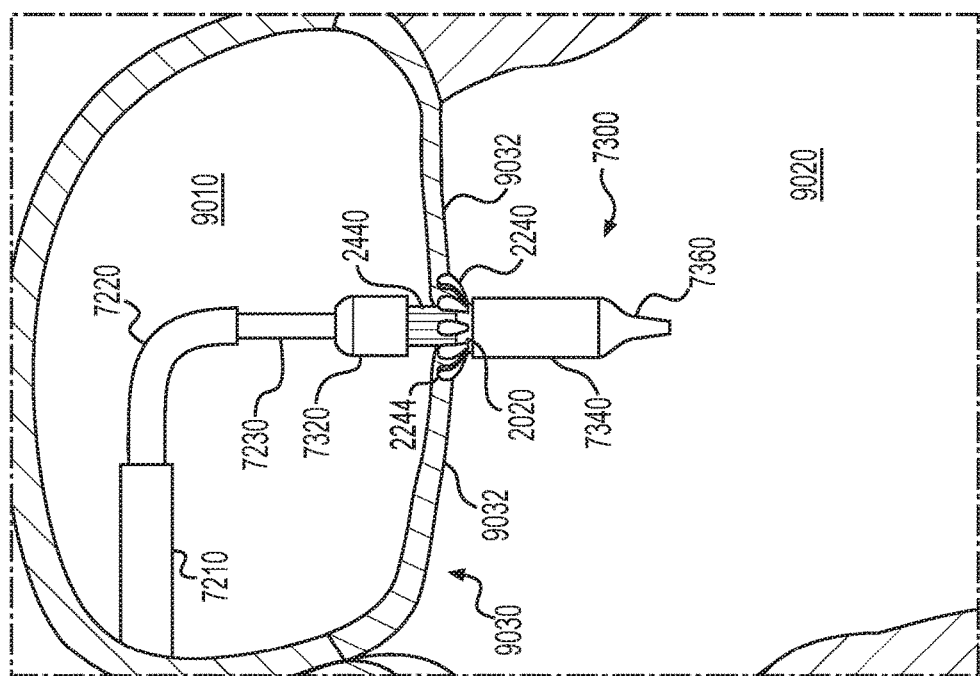

In FIG. 10D, the released ventricular anchoring legs 2240 may be passed through the mitral valve 9030 and into the left ventricle 9020. In FIG. 10E, the released legs 2240 may be proximally retracted until the ventricular anchoring legs come into contact with the ventricular tissue of the mitral valve 9030. In FIG. 10F, the proximal capsule portion 7320 may be retracted proximally, thus releasing the atrial anchoring arms 2440 within atrium 9010 while the annular valve body 2020 remains radially constrained within the distal capsule portion 7340. In some embodiments, the prosthetic valve 6000 may assume the configuration of FIG. 5D when the atrial anchoring arms 2440 are released in the step of FIG. 10F.

Figure 10H:
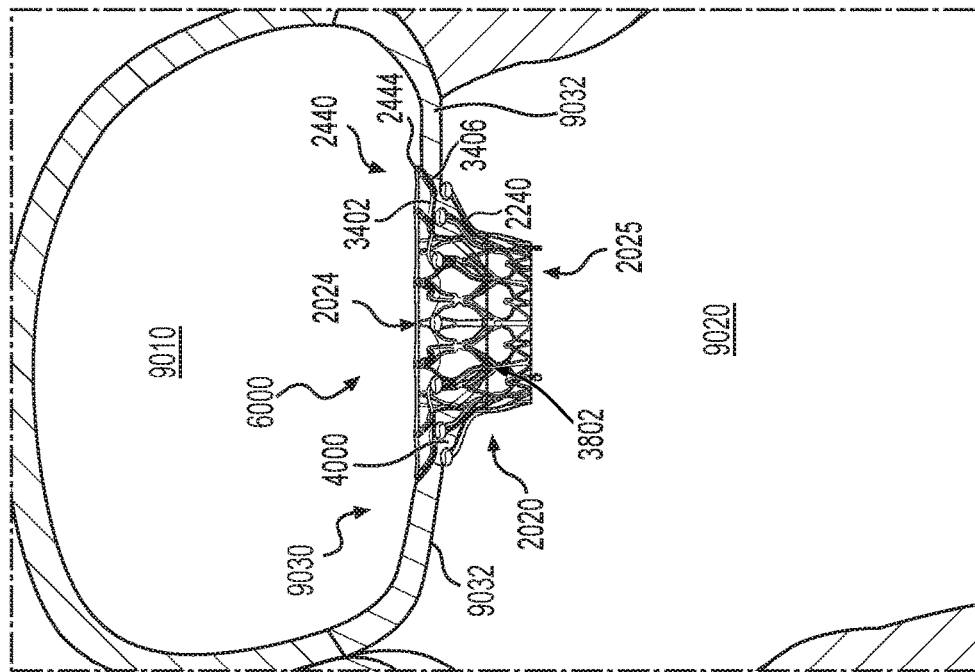
Figure 10G:
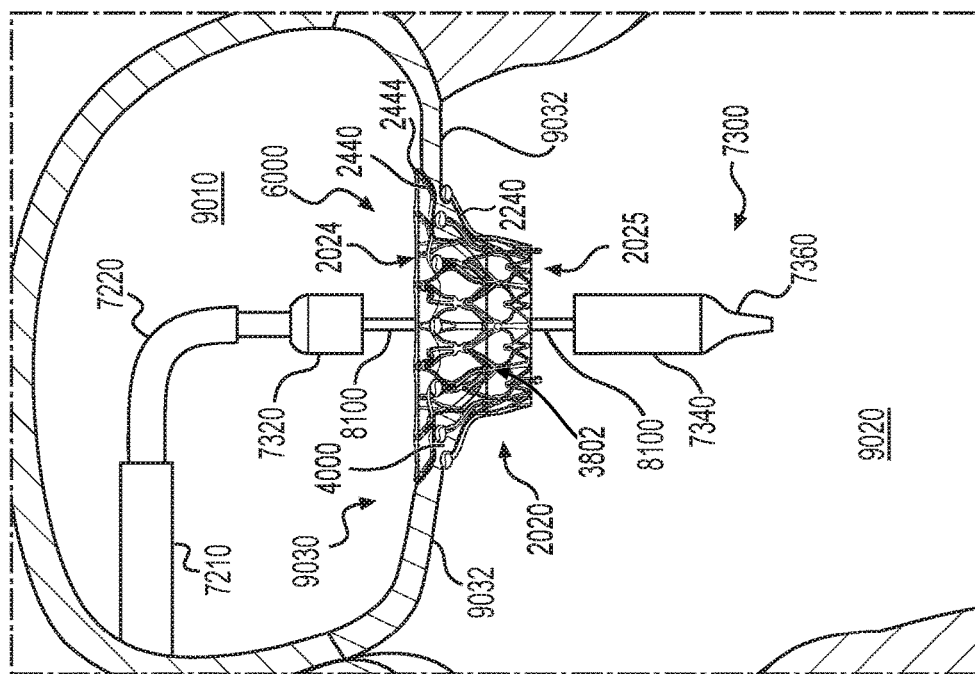

In FIG. 10G, the distal capsule portion 7340 may be advanced further until the annular valve body 2020 is released from the capsule and allowed to radially expand. Radial expansion of the annular valve body 2020 may allow the prosthetic valve to assume the fully-expanded configuration illustrated in FIG. 5E. At this stage, prosthetic valve 6000 may be securely implanted within mitral valve 9030. In FIG. 10H, the delivery system 7000, including capsule 7300, may be removed.

Various embodiments of the present disclosure relate to prosthetic valves, including prosthetic heart valves. While the present disclosure provides examples of prosthetic heart valves, and in particular prosthetic mitral valves, it should be noted that aspects of the disclosure in their broadest sense are not limited to a prosthetic heart valve. Rather, the foregoing principles may be applied to other prosthetic valves as well. Prosthetic heart valve 6000, illustrated in FIGS. 6A-6E, is one example of a prosthetic heart valve in accordance with the present disclosure.

In some embodiments, an exemplary prosthetic valve may be configured for implantation within a native atrioventricular valve and may regulate blood flow between the atrium and ventricle. For example, prosthetic heart valve 6000 illustrated in FIGS. 6A-6C may include a fluid-impervious cuff 6200 configured to extend from an inner lumen 2022 of the prosthetic valve to terminal arm ends 2444 of a plurality of atrial anchoring arms 2440. Because cuff 6200 is constructed of a fluid-impervious material, cuff 6200 may be configured to minimize or block flow of blood and other fluids through any portion of the prosthetic valve 6000 except for lumen 2022. In addition, atrial anchoring arms 2440 of the prosthetic valve (including terminal arm ends 2444) may be configured to contact and, in some embodiments, press against atrial tissue of a native heart valve. This is illustrated in FIGS. 10G-10H, which depict atrial anchoring arms 2440 of prosthetic valve 6000 arranged in contact with, and exerting aventricularly-directed force (that is, a force directed downwards toward ventricle 9020) upon atrial tissue of native mitral valve 9030. As a result, cuff 6200 of prosthetic valve 6000 may also be configured to minimize or block passage of blood and other fluids between the prosthetic valve 6000 (including terminal arm ends 2444) and native valve tissue, a condition known as perivalvular leakage. As a result, prosthetic valve 6000 may be configured to prohibit passage of blood and other fluids between atrium 9010 and ventricle 9020, except by passage through inner lumen 2022, in which leaflets 6602, 6604, and 6606 may be situated.

In some embodiments, an exemplary prosthetic heart valve may include an expandable annular outer frame and an expandable inner frame configured at least partially within the expandable annular outer frame. In some embodiments, the inner frame may be situated at least partially within the outer frame. Alternatively, the inner frame may be situated entirely within the outer frame. One or both of the inner frame and the outer frame may be annular or ring-shaped and may thus have at least one opening therein. In some embodiments, the inner frame may be positioned within an opening of the outer frame. For example, FIG. 2A depicts an exemplary prosthetic valve frame 2000 having an outer frame 2200 and an inner frame 2400. As illustrated in FIG. 2B, inner frame 2400 and outer frame 2200 may both be annular, with inner frame 2400 situated at least partially within outer frame 2200. Because outer frame 2200 and inner frame 2400 are both annular, axial lumen 2022 may extend longitudinally along the entire respective lengths of the outer frame 2200 and inner frame 2400. The inner and outer frames may be constructed of various materials, such as polymeric or metal materials. For example, the inner and outer frames may be constructed of a material that is biocompatible and/or has shape-memory properties. In some embodiments, the inner and outer frames may be constructed, at least partially, of a shape-memory material, such as Nitinol. Additionally, or alternatively, the inner and outer frames may be constructed, at least partially, of stainless steel, chromium alloys, and/or other suitable materials.

In some embodiments, the inner and outer frames may be expandable, such as between respective radially-contracted configurations (e.g., crimped states) and radially-expanded configurations. For example, the inner and outer frames may be configured to transition between the radially-contracted and radially-expanded configurations together due, at least in part, to one or more connections between the frames. For example, FIG. 5A illustrates an inner frame 2400 and outer frame 2200 in respective radially-contracted configurations, while FIG. 5E illustrates inner frame 2400 and outer frame 2200 in respective radially-expanded configurations. The respective diameters of the inner and outer frames may be reduced when the inner and outer frames are arranged in their respective radially-contracted configurations. For example, the inner and outer frames may be arranged in the radially-contracted configurations when the exemplary prosthetic heart valve is delivered to the implantation site. Conversely, the respective diameters of the inner and outer frames may be increased when the inner and outer frames assume their respective radially-expanded configurations. In some embodiments, the inner frame and outer frame may be fully radially-expanded when the inner frame and outer frame are arranged in their radially-expanded configurations.

In some embodiments, the inner frame and outer frame may be configured for self-expansion to their respective radially-expanded configurations; that is, the inner and outer frames may be biased to assume their respective radially-expanded configurations due to, at least in part, the design and/or material composition of the inner and outer frames. The self-expanding frames may be constructed of a shape memory material such as nickel titanium alloy (Nitinol), which may permit the inner and outer frames to expand to pre-determined diameters upon removal of a constraining force and/or application of heat or energy. For example, the inner frame and outer frame may be contracted and held in their respective radially-contracted configurations by a constraining device, such as a sheath, catheter, stent, or delivery capsule. An example of such a constraining device is illustrated in FIG. 8C, which illustrates an inner frame 2400 and outer frame 2200 of an exemplary prosthetic heart valve held in their respective radially-contracted configurations within a delivery capsule 7300. When the inner frame and outer frame are positioned at or near the implantation site (e.g., at the native mitral valve 9030 of FIG. 9), the constraining force (e.g., as applied by delivery capsule 7300) may be removed and the inner frame and outer frame allowed to self-expand to their respective radially-expanded configurations. Additionally, or alternatively, exemplary inner and outer frames may be configured to expand due to application of radially expansive forces thereupon. For example, the inner frame and outer frame may be placed, in their radially-contracted configurations, upon an expansion device such as a balloon catheter. Upon positioning at the implantation site, the expansion device may exert an outwardly-directed force upon the inner and outer frames, causing them to expand to their fully-expanded configurations.

The exemplary inner frame may be configured to receive or otherwise support a flow control device, such as one or more leaflets, for regulating flow of blood or other bodily fluids through the prosthetic heart valve. For example, the flow control device (e.g., leaflets) may be secured directly to the inner frame and/or to an intermediate structure (e.g., a liner) that is in turn secured to the inner frame. For example, FIG. 6C illustrates an embodiment in which leaflets 6602 and 6604 (as well as 6606, which is not depicted in FIG. 6C) are arranged within inner frame 2400. As a result, when the prosthetic heart valve is implanted within a native valve, the flow control device (e.g., leaflets) may regulate fluid passage through the native valve, thus restoring and/or replacing the functionality of the native valve. In the example of a prosthetic mitral valve, the flow control device situated within the inner frame may be configured to permit flow of blood and other fluids in one direction (e.g., from the left atrium to the left ventricle) and to prevent flow of blood and other fluids in a second, opposite direction (e.g., from the left ventricle to the left atrium).

In some embodiments, the annular outer frame may include a tubular portion. The tubular portion may have a circular, oval-shaped, elliptical, or D-shaped cross-section and may have at least one opening therein. In some embodiments, the tubular portion may be symmetrical about at least one axis of the tubular portion. For example, the exemplary outer frame 2200 illustrated in FIG. 3C may include an outer frame tubular portion 3605. Outer frame tubular portion 3605 may have a substantially circular cross-sectional shape with a central opening and may be symmetrical about the longitudinal axis of the prosthetic heart valve. In some embodiments, at least a portion of the tubular portion may be cylindrical, with a substantially constant diameter along the entire length of the tubular portion. Alternatively, the tubular portion may have a variable diameter at different portions of the tubular portion (e.g., at different longitudinal portions thereof). Advantageously, such a configuration may improve the seating of the tubular portion within the heart valve orifice, providing an improved pressure fit therebetween.

In some embodiments, the annular outer frame may include at least one tissue anchor portion configured to extend from the outer frame tubular portion. The at least one tissue anchor portion may include one or more tissue anchors extending from the outer frame tubular portion and configured to engage tissue of a native heart valve to anchor the prosthetic heart valve within or near the native heart valve. In some embodiments, the at least one tissue anchor portion may be configured to abut or clamp tissue of the native heart valve, such as atrial tissue and/or ventricular tissue, to anchor the prosthetic heart valve within the native heart valve. Accordingly, the at least one tissue anchor portion may include one or more atrial tissue anchors, one or more ventricular tissue anchors, or both one or more atrial tissue anchors and one or more ventricular tissue anchors. In the example illustrated in FIG. 2A, the exemplary prosthetic heart valve may include an outer frame tubular portion 3605 including a plurality of ventricular anchoring legs 2240 extending therefrom. Accordingly, the plurality of ventricular anchoring legs 2240, considered together, may constitute the at least one tissue anchor portion in some embodiments.

In some embodiments, the at least one tissue anchor portion may be physically connected to the outer frame tubular portion, such as by welding or adhesive. In some alternative embodiments, the at least one tissue anchor portion may be integrally formed with the outer frame tubular portion. In some embodiments, the at least one tissue anchor portion may be constructed from the same material as the outer frame tubular portion. Such material may include a shape-memory material such as Nitinol, stainless steel, chromium alloys and/or other suitable materials.

In some embodiments, the at least one tissue anchor portion may have a plurality of attachment locations; that is, the at least one tissue anchor portion may be connected to, or otherwise extend from, multiple locations of the outer frame tubular portion. According to embodiments in which the at least one tissue anchor portion includes a plurality of tissue anchors, each tissue anchor may be connected to, or otherwise extend from, a different portion of the outer frame tubular portion. In the example illustrated in FIG. 3C, the plurality of ventricular anchoring legs 2240 (i.e., the exemplary at least one tissue anchor portion) may be connected to a plurality of leg attachment junctions 3802 of the outer frame tubular portion 3605. Accordingly, the plurality of leg attachment junctions 3802 may constitute the plurality of attachment locations in some embodiments.

According to various embodiments, the expandable inner frame of the prosthetic heart valve may be connected to the expandable annular outer frame such that they may be delivered to the implantation site together and may be configured to radially expand and contract together. In some embodiments, the expandable inner frame may be configured to have an outer diameter substantially equal to the inner diameter of the annular outer frame, when the inner and outer frames are radially-expanded. Alternatively, the expandable inner frame may be configured to have an outer diameter larger than the inner diameter of the annular outer frame, when the inner and outer frames are radially-expanded. This arrangement may provide a close friction fit between the expandable inner frame and the expandable annular outer frame, thus further securing the frames together. In some embodiments, the inner and outer frames may be connected by pins, screws, welding, soldering, adhesive, magnets, and/or any other suitable mechanism. The inner and outer frames may be secured together at multiple points of the inner frame and outer frame. For example, FIG. 2A depicts inner frame 2400 and outer frame 2200 connected by a plurality of connector pins 2040, each situated at a different circumferential position of the valve frame 2000 and each configured to extend between the inner 2400 and outer 2200 frames to secure them together. In the example of FIG. 2A, inner frame 2400 and outer frame 2200 may be connected together by twelve connector pins 2040. Alternatively, any suitable number of connector pins may be utilized to secure the inner and outer frames together.

In some embodiments, the expandable inner frame may be connected to the expandable angular outer frame solely at one or more of the plurality of attachment locations of the at least one tissue anchor portion. That is, all of the connections between the inner frame and outer frame may be positioned within, or may extend through, one or more of the attachment locations (i.e., the exemplary portions of the outer frame where the at least one tissue anchor portion connects to, or extends from, the outer frame tubular portion). In some embodiments, the expandable inner frame may be connected to the expandable annular outer frame at all of the attachment locations of the at least one tissue anchor portion. For example, FIG. 2A illustrates the plurality of ventricular anchoring legs 2240 (i.e., the exemplary at least one tissue anchor portion) extending from the outer frame tubular portion 3605 at leg attachment junctions 3802. Inner frame 2200 and outer frame 2400 may be connected by connector pins 2040, which may also be situated within leg attachment junctions 3802. In the example of FIG. 2A, the inner frame 2400 and outer frame 2200 may not be connected by any means other than the connector pins 2040; in addition, the leg attachment junctions 3802 may be the sole portion of the outer frame 2200 at which the connector pins 2040 are located. In some embodiments, the exemplary heart valve frame 2000 illustrated in FIG. 2A may include equal numbers of leg attachment junctions 3802 and connector pins 2040, with one pin 2040 positioned at each leg attachment junction 3802. Alternatively, one or more leg attachment junctions 3802 may not include a connector pin 2040.

In various embodiments, the at least one tissue anchor portion may extend from the outer frame tubular portion at one or more of the plurality of attachment locations. That is, the plurality of attachment locations may constitute the portion of the outer frame tubular portion from which the at least one tissue anchor portion extends. For example, as illustrated in FIGS. 2A and 3C, the plurality of ventricular anchoring legs 2240 (i.e., the exemplary at least one tissue anchor portion) may extend from the outer frame tubular portion 3605 at the leg attachment junctions 3802 (i.e., the exemplary plurality of attachment locations). In some embodiments, the leg attachment junctions 3802 may be the sole portions of the outer frame 2200 from which the plurality of ventricular anchoring legs 2240 extend.

In some embodiments, the plurality of attachment locations may be substantially aligned in a common lateral plane. That is, the plurality of attachment locations may be arranged at the same axial position along the longitudinal axis of the prosthetic heart valve. For example, in FIG. 2A, the leg attachment junctions 3802 (i.e., the exemplary plurality of attachment locations) may be arranged along a plane perpendicular to longitudinal axis 2800. That is, the leg attachment junctions 3802 may be situated at the same axial position along longitudinal axis 2800. Additionally, or alternatively, the leg attachment locations 3802 may be arranged at a regular interval (that is, may be evenly spaced apart) about a circumference of the outer frame tubular portion 3605.

In various embodiments, the expandable inner frame and expandable annular outer frame may be connected by at least one connector configured to extend radially outward beyond the plurality of attachment locations. For example, the inner frame and outer frame may be secured together by a mechanical fastener, such as a pin, which may be configured to extend between the inner and outer frames so as to secure the frames together. For example, the mechanical fastener may extend through openings or apertures in the inner and outer frames, so as to connect the frames together. In some embodiments, the mechanical fastener may be configured to extend radially outward beyond the attachment locations where the at least one tissue anchor portion connects to and extends from the outer frame tubular portion. For example, FIG. 2A illustrates inner frame 2400 and outer frame 2200 secured together at the leg attachment junctions 3802 (i.e., the exemplary plurality of attachment locations) by connector pins 2040. As FIG. 2A also illustrates, connector pins 2040 may extend radially outwards beyond outer surfaces of the leg attachment junctions 3802.

In various embodiments, the at least one tissue anchor portion may include one or more ventricular anchoring legs configured to extend radially outward from the expandable annular outer frame. For example, FIGS. 2A and 3C illustrate an exemplary outer frame 2200 having a plurality of ventricular anchoring legs 2240 extending radially outward therefrom. In some embodiments, the ventricular anchoring legs may be configured to be positioned at least partially within a ventricle upon implantation of the prosthetic heart valve, and to engage ventricular tissue of a native heart valve. For example, FIGS. 10E-10H depict ventricular anchoring legs 2240 of an exemplary prosthetic heart valve 6000. Ventricular anchoring legs 2240 are situated within ventricle 9020 and may engage the ventricular side of native mitral valve 9030 to secure prosthetic heart valve 6000 within the mitral valve.

In some embodiments, the ventricular anchoring legs may be configured to minimize or prevent migration of the prosthetic heart valve into a surrounding heart chamber after the prosthetic, heart valve is implanted. In some embodiments, the ventricular anchoring legs may be configured to have a sufficient length such that they may have a larger diameter than the native heart valve; thus, the ventricular anchoring legs may prevent the prosthetic valve from migrating into the atrium. Additionally, or alternatively, the ventricular anchoring legs may be configured to grasp or clamp tissue of the native heart valve to further anchor the prosthetic heart valve in place. For example, in the embodiment of FIGS. 10G and 10H, ventricular anchoring legs 2240 may clamp tissue by exerting an atrially-directed force (that is, a force directed towards atrium 9010) on the tissue. Additionally, or alternatively, atrial anchoring arms 2440 may clamp the tissue by exerting a ventricularly-directed force (that is, a force directed towards ventricle 9020) on the tissue. These opposing forces may clamp or "sandwich" the native heart tissue between the arms and legs, thus firmly anchoring prosthetic heart valve 6000 within the native heart valve.

The prosthetic heart valve may include two ventricular anchoring legs, three ventricular anchoring legs, four ventricular anchoring legs, five ventricular anchoring legs, six ventricular anchoring legs, seven ventricular anchoring legs, eight ventricular anchoring legs, nine ventricular anchoring legs, ten ventricular anchoring legs, eleven ventricular anchoring legs, twelve ventricular anchoring legs, thirteen ventricular anchoring legs, fourteen ventricular anchoring legs, fifteen ventricular anchoring legs, sixteen ventricular anchoring legs, seventeen ventricular anchoring legs, eighteen ventricular anchoring legs, nineteen ventricular anchoring legs, twenty ventricular anchoring legs, or any other suitable number of ventricular anchoring legs. For example, exemplary prosthetic heart valve 6000 depicted in FIG. 2B may include twelve ventricular anchoring legs 2240.

In some embodiments, the ventricular anchoring legs may be configured to extend radially outward from the outer frame. In some embodiments, the term "radially outward" may refer to a direction extending away from the center of the outer frame (for example, away from the longitudinal axis of the exemplary prosthetic heart valve). For example, FIGS. 5D and 5E illustrate an exemplary ventricular anchoring leg 2240 connected at a proximal leg end 3622 to leg attachment junction 3802 of the outer frame 2200. The ventricular anchoring legs 2240 may extend away from the outer frame 2200 in a radially outward direction to their respective terminal leg ends 2244. In various embodiments, the term "proximal" may refer to a portion of a ventricular anchoring leg in closest proximity to the outer frame and may, in some embodiments, include a point of connection between the ventricular anchoring leg and the outer frame tubular portion. The term "terminal" may refer to a portion of the ventricular anchoring leg furthest from the point of connection between the ventricular anchoring leg and the outer frame tubular portion.

In some embodiments, the locations of connection between the ventricular anchoring legs and the expandable annular outer frame may be spaced at a regular interval about a circumference of the expandable annular outer frame. For example, in FIG. 2A, the ventricular anchoring legs 2240 may extend from the outer frame 2200 at leg attachment junctions 3802. Leg attachment junctions 3802 may be spaced at a regular interval about the circumference of outer frame 2200. Additionally, or alternatively, the locations of connection between the ventricular anchoring legs and the expandable annular outer frame may be arranged along a plane perpendicular to the longitudinal axis of the prosthetic valve. For example, in FIG. 2A, the leg attachment junctions 3802 may be arranged along a plane perpendicular to longitudinal axis 2800. That is, the leg attachment junctions 3802 may be situated at the same axial position along longitudinal axis 2800.

In some embodiments, the prosthetic heart valve may include equal numbers of ventricular anchoring legs and connectors configured to extend the inner frame and outer frame. For example, the prosthetic heart valve frame 2000 illustrated in FIG. 2A may include equal numbers of ventricular anchoring legs 2240 and connector pins 2040. Accordingly, in some embodiments, the prosthetic heart valve may include a connector between the inner frame and outer frame at each point of connection between the ventricular anchoring arms and the outer frame tubular portion.

In exemplary embodiments of the current disclosure, the exemplary prosthetic heart valve may include no connections between the one or more ventricular anchoring legs at a location radially external to the plurality of attachment locations. That is, the ventricular anchoring legs may be free of interconnections at locations radially outward from the locations where the ventricular anchoring legs are connected to the outer frame tubular portion. In some embodiments, the exemplary prosthetic heart valve may include no connections between the one or more ventricular anchoring legs at a location radially external to the plurality of attachment locations when the one or more ventricular anchoring legs are in a radially-expanded configuration. For example, as illustrated in FIGS. 5B, 5D, and 5E, when ventricular anchoring legs 2240 extend radially outward from outer frame tubular portion 3605, the legs 2240 may be free of connections to any of the other legs at locations radially outward from leg attachment junctions 3802.

Additionally, or alternatively, the exemplary prosthetic heart valve may include no connections between the one or more ventricular anchoring legs at a location radially external to the plurality of attachment locations when the inner frame tubular portion is in a radially-contracted configuration. For example, FIGS. 5B and 5D illustrate embodiments in which ventricular anchoring legs 2240 extend radially outward from outer frame tubular portion 3605, which may be radially-constrained. In the embodiments of FIGS. 5B and 5D, each ventricular leg 2240 may be free of connections to any other ventricular leg 2240 at locations radially outward from leg attachment junctions 3802.

Additionally, or alternatively, the exemplary prosthetic heart valve may include no connections between the one or more ventricular anchoring legs at a location radially external to the plurality of attachment locations when the inner frame tubular portion is in a radially-expanded configuration. For example, FIG. 5E illustrates an embodiment in which ventricular anchoring legs 2240 extend radially outward from outer frame tubular portion 3605, which may be in a radially-expanded configuration. In the embodiment illustrated in FIG. 5E, the each ventricular leg 2240 may be free of connections to any other ventricular leg 2240 at locations radially outward from leg attachment junctions 3802.

Advantageously, the ventricular anchoring legs free of interconnections may be configured in a smaller diameter when the ventricular anchoring legs are radially-contracted, as compared to ventricular anchoring legs having interconnections. For example, FIG. 5A illustrates an embodiment in which ventricular anchoring legs 2240 are arranged in a radially-contracted configuration and are free of interconnections beyond leg attachment junctions 3802. In this configuration, the ventricular anchoring legs 2240 may be positioned adjacent to, or may optionally be in contact with, the inner frame tubular portion 3005. As a result, the exemplary prosthetic heart valve illustrated in FIG. 5A may be configured to assume a small diameter when radially-contracted, allowing for the prosthetic heart valve to be contained within a delivery device with a small diameter. In comparison, ventricular anchoring legs having interconnections beyond the attachment locations may be unable to assume the small diameter illustrated in FIG. 5A, because the interconnections between the ventricular anchoring legs may prevent the ventricular anchoring legs from being situated as close together as the ventricular legs are situated in the configuration of FIG. 5A. As a result, the diameter of the radially-contracted ventricular anchoring legs, and thus, the diameter of the delivery device, would be increased as a result of interconnections between the ventricular anchoring legs.

In some embodiments, each of the one or more ventricular anchoring legs may be associated with a single attachment location. For example, each ventricular anchoring leg may be connected to, or may otherwise extend from, a single portion of the outer frame tubular portion. For example, in FIGS. 2A and 3C, each ventricular anchoring leg 2240 may be connected to the outer frame tubular portion 3605 at a single leg attachment junction 3802. Additionally, or alternatively, each of the attachment locations may be associated with a single ventricular anchoring leg. For example, no two ventricular anchoring legs may connect to the same portion of the outer frame tubular portion. For example, in FIGS. 2A and 3C, each single leg attachment junction 3802 may be connected to a single ventricular anchoring leg 2240. As a result, the exemplary prosthetic heart valve may include equal numbers of ventricular anchoring legs and attachment locations. For example, in FIG. 3C, outer frame 2200 may include equal numbers of ventricular anchoring legs 2240 and leg attachment junctions 3802.

In some embodiments, the tubular portion of the expandable annular outer frame may include an atrial end and a ventricular end. In some embodiments, the atrial end may refer to the portion of the outer frame tubular portion configured to be situated closest to the atrium or, if the outer frame tubular portion extends into the atrium, furthest from the ventricle, when the exemplary prosthetic heart valve is implanted in a native atrioventricular valve. For example, as depicted in FIG. 3C, atrial end outer frame junctions 3602 may constitute the atrial end of the outer frame tubular portion 3605, because the atrial end outer frame junctions 3602 are the portions of the outer frame tubular portion 2020 that are situated in closest proximity to atrium 9010 (as shown in FIG. 10H). Similarly, in some embodiments, the ventricular end of the outer frame tubular portion may refer to the portion of the outer frame tubular portion configured to be situated at a location within the ventricle that is furthest from the adjacent atrium, when the exemplary prosthetic heart valve is implanted in a native atrioventricular valve. For example, and as illustrated in FIG. 3C, the ventricular end outer frame junctions 3604 may form the ventricular end of the outer frame tubular portion 3605, because the ventricular end outer frame junctions 3604 are the portions of the outer frame tubular portion 2020 that are situated within ventricle 9020 at a location furthest from atrium 9010 (as shown in FIG. 10H).

In some embodiments, the attachment locations may be positioned away from the atrial and ventricular ends of the outer frame tubular portion. That is, the portions of the outer frame tubular portion to which the at least one tissue anchor portion is connected may be separate from, and spaced apart from, the atrial and ventricular ends of the outer frame tubular portion. Instead, the attachment locations may be positioned in an intermediate portion of the outer frame tubular portion, which may encompass the parts of the outer frame tubular portion between the atrial and ventricular ends outer frame tubular portion. For example, FIG. 3C illustrates the plurality of ventricular anchoring legs 2240 (i.e., the exemplary at least one tissue anchor portion) connected to, or otherwise extending from, the plurality of leg attachment junctions 3802 (i.e., the exemplary attachment locations). As also illustrated in FIG. 3C, leg attachment junctions are positioned away from the atrial end outer frame junctions 3602 (which may form the atrial end of the outer frame tubular portion 3605) and also away from the ventricular end outer frame junctions 3604 (which may form the ventricular end of the outer frame tubular portion 3605).

In various embodiments, the outer frame tubular portion may be formed at least partially of a plurality of supporting members or struts. In some embodiments, the struts may intersect at junctions to form a wire mesh, stent-like, or cage-like structure of the outer frame tubular portion. In some embodiments, the struts of the outer frame tubular portion may be made of one or more metals or alloys, such as Nitinol. In some embodiments, the struts of the outer frame tubular portion may meet or intersect at junctions of the outer frame tubular portion. For example, as illustrated in FIG. 3C, outer frame tubular portion 3605 may include outer frame atrial circumferential struts 3608a, outer frame leg base struts 3608b, and outer frame ventricular circumferential struts 3608c intersecting at atrial end outer frame junctions 3602, leg attachment junctions 3802, outer frame junctions 3804, and ventricular end outer frame junctions 3604. A junction may be formed at a location at which at least two struts terminate; that is, exemplary struts may extend to and terminate at a junction at which they intersect with one or more other struts. In some embodiments, the struts may intersect at junctions to form a lattice or overlapping pattern. In some embodiments, two struts, three struts, four struts, five struts, or any other suitable number of struts may intersect at junctions of the outer frame tubular portion.

In some embodiments, the outer frame tubular portion may include an atrial end formed by one or more junctions of the outer frame. That is, two or more struts of the outer frame may intersect at a junction that forms the atrial end of the outer frame tubular portion. For example, as illustrated in FIG. 3C, outer frame atrial circumferential struts 3608a may intersect at atrial end outer frame junctions 3602, which may form the atrial end of the outer frame tubular portion 3605. Additionally, or alternatively, the outer frame tubular portion may include a ventricular end formed by one or more junctions of the outer frame tubular portion. That is, two or more struts of the outer frame tubular portion may intersect at a junction that forms the ventricular end of the outer frame tubular portion. For example, as illustrated in FIG. 3C, outer frame ventricular circumferential struts 3608c may intersect at ventricular end outer frame junctions 3604, which may form the ventricular end of the outer frame tubular portion 3605. Additionally, or alternatively, the outer frame tubular portion may include one or more intermediate junctions positioned between the atrial junctions and ventricular junctions. For example, as illustrated in FIG. 3C, outer frame tubular portion 3605 may include leg attachment junctions 3802 and outer frame junctions 3804, which may be positioned between the atrial end outer frame junctions 3602 and ventricular end outer frame junctions 3604.

In some embodiments, one or more of the attachment locations may be situated within at least one intermediate junction of the outer frame tubular portion. For example, the at least one tissue anchor portion may connect to, or otherwise extend from, one or more intermediate junctions of the outer frame tubular portion. For example, as illustrated in FIG. 3C, the plurality of ventricular anchoring legs 2240 (i.e., the exemplary at least one tissue anchor portion) may extend from leg attachment junctions 3802 (i.e., the exemplary attachment locations), which may be intermediate junctions of outer frame tubular portion 3605.

In various embodiments, each attachment location may be situated within a junction at which at least three struts intersect. For example, the at least one tissue anchor portion may connect to, or otherwise extend from, junctions of the outer frame tubular portion at which three or more struts intersect. For example, as illustrated in FIG. 3C, the plurality of ventricular anchoring legs 2240 (i.e., the exemplary at least one tissue anchor portion) may extend from leg attachment junctions 3802 (i.e., the exemplary attachment locations), at which two outer frame atrial circumferential struts 3608a and one outer frame leg base strut 3608b intersect.

In various embodiments, at least one of the at least three struts intersecting at the attachment location may extend between the attachment location and a ventricular junction of the outer frame tubular portion. For example, as illustrated in FIG. 3C, outer frame leg base struts 3608b may extend between leg attachment junctions 3802 (i.e., the exemplary attachment locations) and ventricular end outer frame junction 3604, which may constitute the ventricular end of outer frame tubular portion 3605.

In some embodiments, one or more of the attachment locations may be angularly offset from the plurality of atrial junctions of the outer frame tubular portion. That is, the attachment locations and atrial junctions of the outer frame tubular portion may be situated at different positions about the circumference of the outer frame. For example, as illustrated in FIG. 3C, leg attachment junctions 3802 (i.e., the exemplary attachment locations) may be angularly offset from the atrial end outer frame junctions 3602. In some embodiments, the attachment locations may alternate with the atrial junctions of the outer frame tubular portion, about the circumference of the outer frame, Additionally, or alternatively, the attachment locations may be angularly offset at a regular interval from the plurality of atrial junctions of the outer frame tubular portion.

In some embodiments, the expandable inner frame may be formed at least partially of struts intersecting at junctions. In some embodiments, struts of the inner frame may intersect at junctions to form a wire mesh, stent-like, or cage-like inner frame tubular portion. For example, as illustrated in FIG. 3A, inner frame 2400 may include inner frame atrial struts 3008a, inner frame intermediate struts 3008b, and inner frame ventricular struts 3008c intersecting at atrial end inner frame junctions 3002, arm attachment junctions 3202, inner frame strut junctions 3204, and ventricular end inner frame junctions 3004 to form inner frame tubular portion 3005.

In some embodiments, the expandable inner frame may be connected to the outer frame at one or more junctions of the expandable inner frame. For example, a mechanical fastener may extend between the attachment locations on the outer frame tubular portion and junctions of the inner frame to connect the inner frame and outer frame together. For example, as illustrated in FIG. 2A, connector pins 2040 may extend between leg attachment junctions 3802 of outer frame 2200 (i.e., the exemplary attachment locations) and inner frame strut junctions 3204 to connect inner frame 2400 and outer frame 2200. In some embodiments, at least four struts of the inner frame may intersect at the one or more junctions of the inner frame at which the inner frame is secured to the outer frame. For example, as illustrated in FIG. 3A, two inner frame intermediate struts 3008b and two inner frame ventricular struts 3008c may intersect at inner frame strut junctions 3204.

In various embodiments, the exemplary prosthetic heart valve may include a plurality of atrial anchoring arms configured to extend from the expandable inner frame. For example, FIGS. 2A and 3A illustrate an exemplary inner frame 2400 having a plurality of atrial anchoring arms 2440 extending radially outward therefrom. In some embodiments, the atrial anchoring arms may be physically connected to the inner frame, such as by welding or adhesive. In some alternative embodiments, the atrial anchoring arms may be integrally formed with the inner frame. In some embodiments, the atrial anchoring arms may be configured to be positioned at least partially within an atrium upon implantation of the prosthetic heart valve, and to engage atrial tissue of a native heart valve. For example, FIGS. 10F-10H depict atrial anchoring arms 2440 of an exemplary prosthetic heart valve 6000. Atrial anchoring arms 2440 are situated within atrium 9010 and may engage the atrial side of native mitral valve 9030 to secure prosthetic heart valve 6000 within the mitral valve.

In some embodiments, the atrial anchoring arms may be configured to minimize or prevent migration of the prosthetic heart valve into a surrounding heart chamber after the prosthetic heart valve is implanted. In some embodiments, the atrial anchoring arms may be configured to have a sufficient length such that they may have a larger diameter than the native heart valve; thus, the atrial anchoring arms may prevent the prosthetic heart valve from migrating into the ventricle. Additionally, or alternatively, the atrial anchoring arms may be configured to grasp or clamp tissue of the native heart valve to further anchor the prosthetic heart valve in place. For example, in the embodiment of FIGS. 10G and 10H, atrial anchoring arms 2440 may clamp tissue by exerting a ventricularly-directed force (that is, a force directed towards ventricle 9020) on the tissue. Additionally, or alternatively, ventricular anchoring legs 2240 may clamp the tissue by exerting an atrially-directed force (that is, a force directed towards atrium 9010) on the tissue. These opposing forces may clamp or "sandwich" the native heart tissue between the arms and legs, thus firmly anchoring prosthetic heart valve 6000 within the native heart valve.

The prosthetic heart valve may include two atrial anchoring arms, three atrial anchoring arms, four atrial anchoring arms, five atrial anchoring arms, six atrial anchoring arms, seven atrial anchoring arms, eight atrial anchoring arms, nine atrial anchoring arms, ten atrial anchoring arms, eleven atrial anchoring arms, twelve atrial anchoring arms, thirteen atrial anchoring arms, fourteen atrial anchoring arms, fifteen atrial anchoring arms, sixteen atrial anchoring arms, seventeen atrial anchoring arms, eighteen atrial anchoring arms, nineteen atrial anchoring arms, twenty atrial anchoring arms, or any other suitable number of atrial anchoring arms. For example, exemplary prosthetic heart valve 6000 depicted in FIG. 2B may include twelve atrial anchoring arms 2440.

In some embodiments, the atrial, anchoring arms may be configured to extend radially outward from the inner frame. In some embodiments, the term "radially outward" may refer to a direction extending away from the center of the inner frame (for example, away from the longitudinal axis of the exemplary prosthetic heart valve). For example, FIGS. 5D and 5E illustrate an exemplary atrial anchoring arm 2440 connected at a proximal arm end 3020 to arm attachment junction 3202 of the inner frame 2400. The atrial anchoring arms 2440 may extend away from the inner frame 2400 in a radially outward direction to their respective terminal arm ends 2444. In various embodiments, the term "proximal" may refer to a portion of an atrial anchoring arm in closest proximity to the inner frame and may, in some embodiments, include a point of connection between the atrial anchoring arm and the inner frame tubular portion. The term "terminal" may refer to a portion of the atrial anchoring arm furthest from the point of connection between the atrial anchoring arm and the inner frame tubular portion.

In some embodiments, the locations of connection between the atrial anchoring arms and the inner frame may be spaced at a regular interval about a circumference of the inner frame. For example, in FIG. 3A, the atrial anchoring arms 2440 may extend from the inner frame 2400 at arm attachment junctions 3202. Arm attachment junctions 3202 may be spaced at a regular interval about the circumference of inner frame 2400. Additionally, or alternatively, the locations of connection between the atrial anchoring arms and the inner frame may be arranged along a plane perpendicular to the longitudinal axis of the prosthetic valve. For example, in FIG. 2A, the arm attachment junctions 3202 may be arranged along a plane perpendicular to longitudinal axis 2800. That is, the arm attachment junctions 3202 may be situated at the same axial position along longitudinal axis 2800.

In some embodiments, one or more of the attachment locations of the at least one tissue anchor portion to the outer frame tubular portion may be angularly offset from the atrial anchoring arms. That is, the attachment locations and atrial anchoring arms may be situated at different positions about the circumference of the prosthetic heart valve. For example, as illustrated in FIG. 2A, leg attachment junctions 3802 (i.e., the exemplary attachment locations) may be angularly offset from the atrial anchoring arms 2440. In some embodiments, the attachment locations may alternate with the atrial anchoring arms about the circumference of the prosthetic heart valve. Additionally, or alternatively, the attachment locations may be angularly offset at a regular interval from the atrial anchoring arms.

In some embodiments, the expandable inner frame may have a greater axial length than the expandable annular outer frame, relative to the longitudinal axis of the exemplary prosthetic heart valve. In some embodiments, the inner frame, including the inner frame tubular portion and the plurality of atrial anchoring arms, may have a greater axial length than the outer frame, including the outer frame tubular portion and the plurality of ventricular anchoring legs. For example, in the embodiment depicted in FIG. 2D, device height 2560 may represent the axial length of inner frame 2400, including inner frame tubular portion 3005 and atrial anchoring arms 2440. Similarly, outer frame height 2550 may represent the axial length of outer frame 2200, including outer frame tubular portion 3605 and ventricular anchoring legs 2240. As illustrated in FIG. 2D, device height 2560 may be greater than outer frame height 2550.

Additionally, or alternatively, the inner frame tubular portion may have a greater axial length than the outer frame tubular portion, relative to the longitudinal axis of the exemplary prosthetic heart valve. For example, in the embodiment depicted in FIG. 2D, inner frame tubular portion height 2530 may represent the axial length of inner frame tubular portion 3005. Inner frame tubular portion height 2530 may extend axially between atrial end inner frame junctions 3002 and ventricular end inner frame junctions 3004. Similarly, outer frame tubular portion height 2570 may represent the axial length of outer frame tubular portion 3605. Outer frame tubular portion height 2570 may extend axially between atrial end outer frame junctions 3602 and ventricular end outer frame junctions 3604. As illustrated in FIG. 2D, inner frame tubular portion height 2530 may be greater than outer frame tubular portion height 2570. In some embodiments, the ventricular ends of the inner frame and outer frame may be substantially aligned in a common lateral plane; that is, the ventricular ends of the inner frame and outer frame may be arranged along a plane perpendicular to the longitudinal axis of the prosthetic heart valve. For example, in FIG. 2D, ventricular end inner frame junctions 3004 may be substantially aligned in a common lateral plane with ventricular end outer frame junctions 3604. Further, the atrial end of the inner frame may extend in an atrial direction beyond the atrial end of the outer frame (that is, the atrial end of the inner frame may be positioned above the atrial end of the outer frame in FIG. 2D). For example, in FIG. 2D, the atrial end inner frame junctions 3002 may be positioned in an atrial direction from the atrial end outer frame junctions 3602.

In some embodiments, the exemplary prosthetic heart valve may include at least one delivery post extending from a ventricular end of the expandable inner frame. The prosthetic heart valve may include one delivery post, two delivery posts, three delivery posts, four delivery posts, five delivery posts, or any other suitable number of delivery posts extending from the ventricular end of the expandable inner frame. In some embodiments, a plurality of delivery post may be evenly spaced along the circumference of the ventricular end of the expandable inner frame. The at least one delivery post may be configured to removably engage a delivery tool, such that the delivery tool may be configured to manipulate and position the prosthetic heart valve at a desired implantation site in the body. For example, exemplary heart valve frame 2000 illustrated in FIG. 2A may include three ventricular end delivery posts 2028, which may be situated at the ventricular end of inner frame 2400. For example, in some embodiments the delivery posts 2028 may extend from at least one ventricular end inner frame junction 3004 (as illustrated in FIG. 3A). Ventricular end delivery posts 2028 may be configured to removably engage a delivery tool of prosthetic heart valve 6000. For example, FIG. 8C illustrates prosthetic heart valve 6000 positioned within delivery capsule 7300. As depicted in FIG. 8C, ventricular end delivery posts 2028 may engage valve anchor 8200 to secure prosthetic heart valve 6000 against axial movement. However, upon expansion of annular valve body 2025, ventricular end delivery posts 2028 may disengage from valve anchor 8200.

In some embodiments, the at least one delivery post may be angularly offset from one or more of the attachment locations of the at least one tissue anchor portion to the outer frame tubular portion. That is, the at least one delivery post and the attachment locations may be situated at different positions about the circumference of the prosthetic heart valve. For example, as illustrated in FIG. 2A, ventricular end delivery posts 2028 may be angularly offset from the leg attachment junctions 3802 (i.e., the exemplary attachment locations). In some embodiments, the exemplary prosthetic heart valve may include a greater number of attachment locations than delivery posts. Alternatively, the exemplary prosthetic heart valve may include an equal number of attachment locations and delivery posts. In some embodiments, the at least one delivery post may be situated in a location equidistant from two adjacent attachment locations. For example, as illustrated in FIG. 2A, each ventricular end delivery post 2028 may be positioned between two adjacent leg attachment junctions 3802, such that the ventricular end delivery post 2028 may be equidistant from the two adjacent leg attachment junctions 3802.

In various embodiments, the prosthetic heart valve may be configured for expansion from a radially-contracted configuration to a radially-expanded configuration. For example, FIG. 5A illustrates an exemplary radially-contracted configuration of an exemplary prosthetic heart valve. In the configuration illustrated in FIG. 5A, the inner frame tubular portion 3005, outer frame tubular portion 3605, the plurality of atrial anchoring arms 2440, and the plurality of ventricular anchoring legs 2240 may be radially-contracted, such at their respective diameters may be reduced. FIG. 5E illustrates an exemplary radially-expanded configuration of the exemplary prosthetic heart valve. In the configuration illustrated in FIG. 5E, the inner frame tubular portion 3005, outer frame tubular portion 3605, the plurality of atrial anchoring arms 2440, and the plurality of ventricular anchoring legs 2240 may be radially-expanded, such that the ventricular anchoring legs 2240 may expand and/or deflect radially outwards from their respective radially-contracted configurations.

In some embodiments, a distance between a given attachment location and the ventricular end of the annular outer frame may remain constant between the radially-contracted configuration and the radially-expanded configuration of the prosthetic heart valve. That is, radial expansion or contraction of the prosthetic heart valve may not cause variation in the axial distance between the attachment location and the ventricular end of the annular outer frame. For example, the axial distance between leg attachment junctions 3802 (i.e., the exemplary attachment locations) and the ventricular end outer frame junctions 3604 (i.e., the exemplary ventricular end of outer frame 2200) may remain constant between the configuration of FIG. 5A and the configuration of FIG. 5E.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and, accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A prosthetic heart valve, comprising:
an expandable annular outer frame having a tubular portion and a plurality of tissue anchor portions extending from the tubular portion, the tubular portion being formed at least partially of struts intersecting at junctions, including a plurality of atrial junctions at an atrial end of the tubular portion, a plurality of ventricular junctions at a ventricular end of the tubular portion, and a plurality of intermediate junctions between the atrial junctions and ventricular junctions, each of the tissue anchor portions having:
a proximal end connected to an attachment location on the tubular portion, and
a terminal end opposite from the proximal end, wherein at least one tissue anchor portion is configured to extend radially outward from the tubular portion between the proximal end of the at least one tissue anchor portion and the terminal end of the at least one tissue anchor portion; and
an expandable inner frame situated at least partially within the expandable annular outer frame, wherein
the expandable annular outer frame is connected to the expandable inner frame solely at one or more of the attachment locations situated within at least one intermediate junction of the tubular portion, and wherein
no connection is made between the plurality of tissue anchor portions between the proximal end of the at least one tissue anchor portion and the terminal end of the at least one tissue anchor portion.

2. The prosthetic heart valve of claim 1, wherein the attachment locations are aligned in a common lateral plane.

3. The prosthetic heart valve of claim 1, wherein the expandable inner frame and expandable annular outer frame are connected by at least one connector configured to extend radially outward beyond an outer surface of the expandable annular outer frame.

4. The prosthetic heart valve of claim 1, wherein the at least one tissue anchor portion is configured to engage ventricular tissue of a native heart valve so as to anchor the prosthetic heart valve within the native heart valve.

5. The prosthetic heart valve of claim 4, further comprising:
a plurality of atrial anchoring arms configured to extend from the expandable inner frame, wherein the atrial anchoring arms are configured to engage atrial tissue of the native heart valve so as to anchor the prosthetic heart valve within the native heart valve.

6. The prosthetic heart valve of claim 5, wherein one or more of the attachment locations is angularly offset from the atrial anchoring arms.

7. The prosthetic heart valve of claim 1, wherein each of the tissue anchor portions is connected to the tubular portion at a single attachment location.

8. The prosthetic heart valve of claim 1,
wherein the tubular portion of the expandable annular outer frame includes an atrial end and a ventricular end, and
wherein the attachment locations are positioned between the atrial end and ventricular end of the tubular portion.

9. The prosthetic heart valve of claim 1, wherein each attachment location is situated within a junction at which at least three struts intersect.

10. The prosthetic heart valve of claim 9, wherein at least one of the at least three struts extends between the attachment location and a ventricular junction.

11. The prosthetic heart valve of claim 1, wherein one or more of the attachment locations is angularly offset from the plurality of atrial junctions of the tubular portion of the expandable annular outer frame.

12. The prosthetic heart valve of claim 1,
wherein the expandable inner frame is formed at least partially of struts intersecting at junctions; and
wherein the expandable inner frame is connected to the expandable annular outer frame at one or more junctions of the expandable inner frame.

13. The prosthetic heart valve of claim 12, wherein at least four struts intersect at the one or more junctions of the expandable inner frame.

14. The prosthetic heart valve of claim 1, wherein the expandable inner frame has a greater axial length than the expandable annular outer frame.

15. The prosthetic heart valve of claim 1, wherein the expandable inner frame further comprises:
at least one delivery post extending from a ventricular end of the expandable inner frame.

16. The prosthetic heart valve of claim 15, wherein the at least one delivery post is angularly offset from one or more of the attachment locations.

17. The prosthetic heart valve of claim 1,
wherein the prosthetic heart valve is configured for expansion from a radially-contracted configuration to a radially-expanded configuration, and
wherein a distance between a particular attachment location and a ventricular end of the annular outer frame is constant between the radially-contracted configuration and the radially-expanded configuration.

* * * * *